US012674174B2

(12) United States Patent
Shalitin et al.

(10) Patent No.: US 12,674,174 B2
(45) Date of Patent: Jul. 7, 2026

(54) PROTOPORPHYRINOGEN OXIDASE (PPO) RESISTANCE PLANT

(71) Applicant: PLANTARC BIO LTD., Raanana (IL)

(72) Inventors: Dror Shalitin, Raanana (IL); Noam Grimberg, Kibutz Lehavot Haviva (IL); Daniel Bechar, Kibbutz Givat Haim Meuhad (IL); Tal Cohen, Herzelyia (IL); Aviva Katz, Kfar Saba (IL); Martin Mandelbaum, Tel Aviv (IL)

(73) Assignee: PLANTARC BIO LTD., Raanana (IL)

( * ) Notice: Subject to any disclaimer, the term of this patent is extended or adjusted under 35 U.S.C. 154(b) by 0 days.

(21) Appl. No.: 19/034,521

(22) Filed: Jan. 22, 2025

(65) Prior Publication Data

US 2025/0163448 A1      May 22, 2025

Related U.S. Application Data

(63) Continuation of application No. PCT/IL2023/050776, filed on Jul. 26, 2023.

(60) Provisional application No. 63/423,001, filed on Nov. 6, 2022, provisional application No. 63/393,933, filed on Jul. 31, 2022.

(51) Int. Cl.
*C12N 15/82* (2006.01)
*C12N 9/02* (2006.01)
(52) U.S. Cl.
CPC ......... *C12N 15/8274* (2013.01); *C12N 9/001* (2013.01); *C12Y 103/03004* (2013.01)
(58) Field of Classification Search
None
See application file for complete search history.

(56) References Cited

U.S. PATENT DOCUMENTS

2014/0259212 A1      9/2014   Plesch et al.

FOREIGN PATENT DOCUMENTS

WO      2019118726 A2      6/2019

OTHER PUBLICATIONS

Hao et al, Chemistry in China (2011) 65:961-969.*
UniProt Accession No. A0A318YKB3_ASPNB, submitted on Oct. 10, 2018.*
Li X, Nicholl D. Development of PPO inhibitor-resistant cultures and crops. Pest Manag Sci. Mar. 2005;61(3):277-85. doi: 10.1002/ps.1011. PMID: 15660355.
Hazel R. Corradi, Anne V. Corrigall, Ester Boix, C.Gopi Mohan, Edward D. Sturrock, Peter N. Meissner, K.Ravi Acharya. Crystal Structure of Protoporphyrinogen Oxidase from Myxococcus xanthus and Its Complex with the Inhibitor Acifluorfen. Journal of Biological Chemistry, vol. 281, Issue 50, 2006, pp. 38625-38633, https://doi.org/10.1074/jbc.M606640200.
PCT International Search Report for International Application No. PCT/IL2023/050776, mailed Oct. 19, 2023, 5pp.
PCT Written Opinion for International Application No. PCT/IL2023/050776, mailed Oct. 19, 2023, 6pp.

* cited by examiner

Primary Examiner — Mykola V. Kovalenko
(74) Attorney, Agent, or Firm — The Roy Gross Law Firm, LLC; Roy Gross

(57) ABSTRACT

Disclosed are transgenic plant expressing a fungal protoporphyrinogen oxidase (PPO) enzyme and methods for conferring Herbicide Tolerance (HT) to PPO-type inhibitor herbicides, and controlling weeds, by selectively protecting the transgenic crop expressing the fungal PPO enzyme.

13 Claims, 10 Drawing Sheets
(10 of 10 Drawing Sheet(s) Filed in Color)

Specification includes a Sequence Listing.

Strike conc.          0%          0.0003%          0.000015%

| Trail # | 1 | | | 2 | | | | | | |
|---|---|---|---|---|---|---|---|---|---|---|
| Herbicide | Strike | | | Strike | | | | Aurora | | |
| Consentration [%v/v] | 0.01 | 0.1 | 0.5 | 0.01 | 0.1 | 0.5 | 1 | 0.01 | 0.1 | 0.5 |
| Gene | | | | | | | | | | |
| SEQ ID NO: 1 | 5 | 5 | 5 | 4 | 5 | 4 | 3 | 5 | 3 | 3 |
| SEQ ID NO: 8 | 5 | 5 | 5 | 5 | 4 | 4 | 4 | 5 | 4 | 4 |
| SEQ ID NO: 2 | 4 | 4 | 4 | 4 | 3 | 3 | 3 | 4 | 3 | 3 |
| SEQ ID NO: 9 | 5 | 5 | 5 | 5 | 5 | 5 | 4 | 5 | 4 | 3 |
| SEQ ID NO: 3 | 3 | 2 | 1 | | | | | | | |
| SEQ ID NO: 10 | 5 | 5 | 4 | 4 | 4 | 3 | 3 | 3 | 3 | 1 |
| SEQ ID NO: 11 | | | | 3 | 3 | 2 | 2 | 2 | 1 | 1 |
| SEQ ID NO: 12 | 5 | 5 | 5 | 4 | 4 | 3 | 2 | 3 | 0 | 0 |
| SEQ ID NO: 6 | 5 | 5 | 5 | 5 | 5 | 3 | 3 | 5 | 3 | 3 |
| SEQ ID NO: 14 | | | | 2 | 0 | 0 | 0 | 4 | 4 | 4 |

FIG. 3A

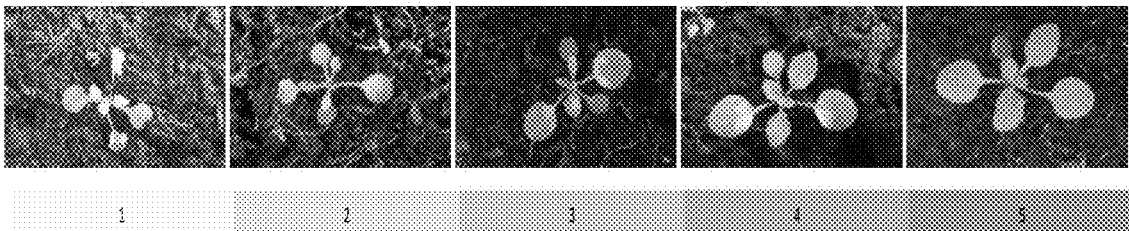

FIG. 3B

| Respective SEQ ID NO without cTP | SEQ ID (with the cTP) | Strike 2.5 kg/hectar | Genus |
|---|---|---|---|
| | transformed to plants | tolerance score | |
| | "empty" vector control | 1 | |
| SEQ ID NO: 1 | SEQ ID NO: 8 | 5 | Aspergillus |
| SEQ ID NO: 2 | SEQ ID NO: 9 | 5 | Aspergillus |
| SEQ ID NO: 3 | SEQ ID NO: 10 | 5 | Fusarium |
| SEQ ID NO: 4 | SEQ ID NO: 11 | 4 | Fusarium |
| SEQ ID NO: 5 | SEQ ID NO: 12 | 5 | Fusarium |
| SEQ ID NO: 6 | SEQ ID NO: 13 | 2 | Rhizopus |
| SEQ ID NO: 7 | SEQ ID NO: 14 | 4 | Penicillium |
| SEQ ID NO: 86 | SEQ ID NO: 104 | 2 | Trichoderma |
| SEQ ID NO: 87 | SEQ ID NO: 105 | 1 | Aspergillus |
| SEQ ID NO: 88 | SEQ ID NO: 106 | 2 | Aspergillus |
| SEQ ID NO: 89 | SEQ ID NO: 107 | 2 | Fusarium |
| SEQ ID NO: 90 | SEQ ID NO: 108 | 1 | Fusarium |
| SEQ ID NO: 91 | SEQ ID NO: 109 | 3 | Rhizopus |
| SEQ ID NO: 92 | SEQ ID NO: 110 | 3 | Rhizopus |
| SEQ ID NO: 93 | SEQ ID NO: 111 | 3 | Rhizopus |
| SEQ ID NO: 94 | SEQ ID NO: 112 | 2 | Penicillium |
| SEQ ID NO: 95 | SEQ ID NO: 113 | 2 | Penicillium |
| SEQ ID NO: 96 | SEQ ID NO: 114 | 5 | Trichoderma |
| SEQ ID NO: 97 | SEQ ID NO: 115 | 5 | Rhodotorula |
| SEQ ID NO: 98 | SEQ ID NO: 116 | 2 | Hesseltinella |
| SEQ ID NO: 99 | SEQ ID NO: 117 | 2 | Spizellomyces |
| SEQ ID NO: 100 | SEQ ID NO: 118 | 1 | Rhizophagus |

FIG. 3C

| SEQ ID | SEQ ID (with the cTP) Transformed to plants | cTP | Tolerance score | | | |
|---|---|---|---|---|---|---|
| | | | Aurora 1 kg/hectare | Goal 1.15 kg/hectare | Star 1.25 kg/hectare | Strike 2.5 kg/hectare |
| | "empty" vector control | | 1 | 1 | 1 | 1 |
| SEQ ID NO: 98 | SEQ ID NO: 116 | v | 3 | 5 | 5 | 2 |
| SEQ ID NO: 94 | SEQ ID NO: 112 | v | 5 | 5 | 5 | 2 |
| SEQ ID NO: 96 | SEQ ID NO: 114 | v | 3 | 5 | 5 | 5 |
| SEQ ID NO: 97 | SEQ ID NO: 115 | v | 4 | 5 | 5 | 4 |
| SEQ ID NO: 2 | SEQ ID NO: 9 | v | 5 | 5 | 5 | 5 |

FIG. 6A

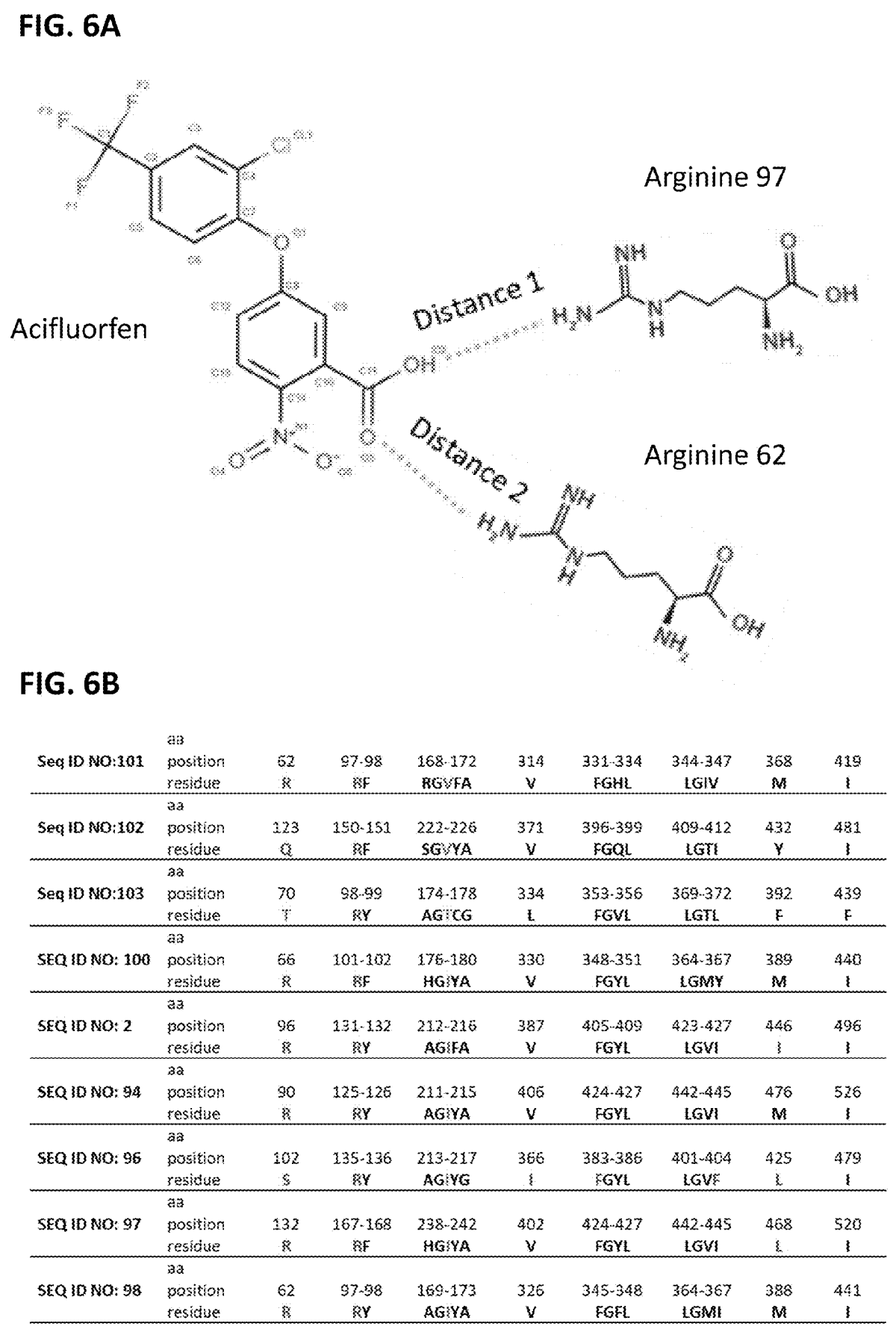

Acifluorfen

Arginine 97

Distance 1

Arginine 62

Distance 2

FIG. 6B

| | aa | | | | | | | | |
|---|---|---|---|---|---|---|---|---|---|
| Seq ID NO:101 | position | 62 | 97-98 | 168-172 | 314 | 331-334 | 344-347 | 368 | 419 |
| | residue | R | RF | RGVFA | V | FGHL | LGIV | M | I |
| Seq ID NO:102 | aa position | 123 | 150-151 | 222-226 | 371 | 396-399 | 409-412 | 432 | 481 |
| | residue | Q | RF | SGVYA | V | FGQL | LGTI | Y | I |
| Seq ID NO:103 | aa position | 70 | 98-99 | 174-178 | 334 | 353-356 | 369-372 | 392 | 439 |
| | residue | T | RY | AGTCG | L | FGVL | LGTL | F | F |
| SEQ ID NO: 100 | aa position | 66 | 101-102 | 176-180 | 330 | 348-351 | 364-367 | 389 | 440 |
| | residue | R | RF | HGIYA | V | FGYL | LGMY | M | I |
| SEQ ID NO: 2 | aa position | 96 | 131-132 | 212-216 | 387 | 405-409 | 423-427 | 446 | 496 |
| | residue | R | RY | AGIFA | V | FGYL | LGVI | I | I |
| SEQ ID NO: 94 | aa position | 90 | 125-126 | 211-215 | 406 | 424-427 | 442-445 | 476 | 526 |
| | residue | R | RY | AGIYA | V | FGYL | LGVI | M | I |
| SEQ ID NO: 96 | aa position | 102 | 135-136 | 213-217 | 366 | 383-386 | 401-404 | 425 | 479 |
| | residue | S | RY | AGIYG | I | FGYL | LGVF | L | I |
| SEQ ID NO: 97 | aa position | 132 | 167-168 | 238-242 | 402 | 424-427 | 442-445 | 468 | 520 |
| | residue | R | RF | HGIYA | V | FGYL | LGVI | L | I |
| SEQ ID NO: 98 | aa position | 62 | 97-98 | 169-173 | 326 | 345-348 | 364-367 | 388 | 441 |
| | residue | R | RY | AGIYA | V | FGFL | LGMI | M | I |

SEQUENCE LISTING

```
Sequence total quantity: 121
SEQ ID NO: 1           moltype = AA  length = 597
FEATURE                Location/Qualifiers
source                 1..597
                       mol_type = protein
                       organism = Aspergillus sp.
SEQUENCE: 1
MRLPCASSRV FRQVRAPLAL LSRGQRHAVH TKQFDAAVIG GGITGLTAAY QLSRDPSCSK   60
VTLYEKSPHL GGWLSSEQIP VPGGHVVFEY GPRTLRTSSP SCLPMMDLIM NLDLLDDVLI  120
CDKKSPAAQN RYIYYPDHLV RLPFPPTEGL LKTAWTLLME PLFETFLYSA IFEKPKRAEN  180
THILSRDESV ADFVSRRFSP KISENLASAV MAGIFAGDVN RLSAEMAIGY VRELEKRYGS  240
IVDGMMTQRA SEMRAMPMDE LLALESVAVP SHSDDRYWKS LRAVVSDASV LTLKNGLGQL  300
TDAMAAQLRS SRNVEVVTGT EVTSLSQNPK TQDLTIGFGK NESKTHNRVI ATHAPSSLAR  360
QIQNTKVGVV PSDTIRDLGQ NNYAVTVMVV NLYYEDPDLV PVEGFGYLLP SSVPFEQNPE  420
```

-continued

```
RALGVIFGSQ SSEGQDTAPG TKLTVMMGGH LWDGWSESDY PDPDKAIEMA QALLHRHLGI   480
KTAPSVARAR LLRDAIPQYT VGHLSRMKEL SHSVRSDFHK RLTLAGAWYG TVGIGVVDCI   540
RQGYLASSYG VGSKKLGPGN SRRPWTKHDF HNWELEGGIA TSPVRLDNVH VTERQHY      597

SEQ ID NO: 2            moltype = AA  length = 597
FEATURE                 Location/Qualifiers
source                  1..597
                        mol_type = protein
                        organism = Aspergillus sp.
SEQUENCE: 2
MRLPCASSRA FRQVRAPLAL LHRGQRHAVH TKQFDAAVIG GGITGLTAAY QLSRDPSCSK   60
VTLYEKSSHL GGWLSSEQIP VPGGHVVFEY GPRTLRTSSP SCLPMMDLIM NLDLLDDVLI   120
CDKKSPAAQN RYIYYPDHLV RLPFPPTEGL LKTAWTLLME PLFETFLYSA IFEKPKRAEN   180
THILSRDESV ADFVSRRFSP KISENLASAV MAGIFAGDVN RLSAEMAIGY VRELEKRYGS   240
IVDGMMTQRA SEMRAMPMDE LLALESVAVP SHSDDRYWKS LRAVVTDASV LTLKNGLGQL   300
TDAMAAQLRS SRNVEVVTGT EVTSLSQNPK TQDLTIGFGK NESRTHNRVI ATHAPSSLAR   360
QIQNTKVGVV PSDTIRDLGQ NNYAVTVMVV NLYYEDPDLV PVEGFGYLLP SSVPFEQNPE   420
RALGVIFGSQ SSEGQDTAPG TKLTVIMGGH LWDGWSESDY PDPDKAIEMA QALLHRHLGI   480
KTAPSVARAR LLRDAIPQYT VGHLSRMKEL SHSVRSDFHK RLTLAGAWYG TVGIGVVDCI   540
RQGYLASSYG VGSKKLGPGN SRRPWTKHDF HNWELEGGIA TSPVRFDNVH VTERQHY      597

SEQ ID NO: 3            moltype = AA  length = 595
FEATURE                 Location/Qualifiers
source                  1..595
                        mol_type = protein
                        organism = Fusarium sp.
SEQUENCE: 3
MSRRRAESTA VALLSSPAKS HLQPPLRRLD GIRSLSTSSA LARRRPIVAC NYTQSFNNGR   60
TFVSQAKDAN IAVLGGGLTG LTAAYYLAKK LPSTAKITLY ESSDRLGGWI KTDRVPVDIE   120
GKSGTLSFER GARSLSSLVG NTFRFDDLVL YDLALDLGLA INSPSQQPRY IYYPDHLVPT   180
PPNISIFDML REPLYLEIIG ASLGLGINSL RKRTLPSKDY SVSEWLYAVS NSRKGIGNLA   240
SAMMHGIYGG DIHKLSARCV LDRLYWGWYL PNPGLSVRPM PVAEQALLET LGQDKQIQKM   300
ALEPRSALVD FGDKGMESLP QALSAALREQ PNITIKTGEA VQDVVYNKAN QQVHITSSNA   360
KDNSKHNSKV YDKVISTLSA QDIALLAGNK LPSLSTAHSV SVMTVNIWFP QENLKPPGFG   420
YLIPNSVAPE LNPEHALGVF FDSDVQTRSK DEPAGTKLFV LMGGHYYDRP DVTPPTEEEA   480
IIQARNLLER HLGIPRDAPA YATANFAREC IPQHYVGHQD RLKAAHTELT RNFGGRLAVA   540
GGSFTRIGAV ASLRAGYDAA TAAKKGLEAT GLEYLNDIQQ FSVVATSHIP VRHFK       595

SEQ ID NO: 4            moltype = AA  length = 595
FEATURE                 Location/Qualifiers
source                  1..595
                        mol_type = protein
                        organism = Fusarium sp.
SEQUENCE: 4
MSRRRAESTA VALLSSPAKS HLQPPLRRLD GIRSLSTSSA LARRRPIVAC NYTQSFNNGR   60
TFVSQAKDAN IAVLGGGLTG LTAAYYLAKK LPSTAKITLY ESSDRLGGWI KTDRVPVDIE   120
GKSGTLSFER GARSLSSLVG NTFRFDDLVL YDLALDLGLA INSPSQQPRY IYYPDHLVPT   180
PPNISIFDML REPLYLEIIG ASLGLGINSL RKRTLPSKDY SVSEWLYAVS NSRKGIGNLA   240
SAMMHGIYGG DIHKLSARCV LDRLYWGWYL PNPGLSVRPM PVAEQALLET LGQDKQIQKM   300
ALEPRSALVD FGDKGMESLP QALSAALREQ PNITIKTGEA VQDVVYNKAN QQVHITSSNA   360
KDNSKHNSKV YDKVISTLSA QDIALLAGNK LPSLSTAHSV SVMTVNIWFP QENLKPPGFG   420
YLIPNSVAPE LNPEHALGVF FDSDVQTRSK DEPAGTKLFV LMGGHYYDRP DVTPPTEEEA   480
IIQARNLPER HLGIPRDAPA YATANFAREC IPQHYVGHQD RLKAAHTELT RNFGGRLAVA   540
GGSFTRIGAV ASLRAGYDAA TAAKKGLEAT GLEYLNDIQQ FSVVATSHIP VRHFK       595

SEQ ID NO: 5            moltype = AA  length = 595
FEATURE                 Location/Qualifiers
source                  1..595
                        mol_type = protein
                        organism = Fusarium sp.
SEQUENCE: 5
MSRRRAESTA VALLSSPAKS HLQPPLRRLD GIRSLSTSSA LARRRPIVAC NYTQSFNNGR   60
TFVSQAKDAN IAVLGGGLTG LTAAYYLAKK LPSTAKITLY ESSDRLGGWI KTDRVPVDIE   120
GKSGTLSFER GARSLSSLVG NTFRFDDLVL YDLALDLGLA INSPSQQPRY IYYPDHLVPT   180
PPNISIFDML REPLYLEIIG ASLGLGINSR RKRTLPSKDY SVSEWLYAVS NSRKGIGNLA   240
SAMMHGIYGG DIHKLSARCV LDRLYWGWYL PNPGLSVRPM PVAEQALLET LGQDKQIQKM   300
ALEPRSALVD FGDKGMESLP QALSAALREQ PNITIKTGEA VQDVVYNKAN QQVHITSSNA   360
KDNSKHNSKV YDKVISTLSA QDIALLAGNK LPSLSTAHSV SVMTVNIWFP QENLKPPGFG   420
YLIPNSVAPE LNPEHALGVF FDSDVQTRSK DEPAGTKLFV LMGGHYYDRP DVTPPTEEEA   480
IIQARNLLER HLGIPRDAPA YATANFAREC IPQHYVGHQD RLKAAHTELT RNFGGRLAVA   540
GGSFTRIGAV ASLRAGYDAA TAAKKGLEAT GLEYLNDIQQ FSVVATSQIP VRHFK       595

SEQ ID NO: 6            moltype = AA  length = 560
FEATURE                 Location/Qualifiers
source                  1..560
                        mol_type = protein
                        organism = Rhizopus sp.
SEQUENCE: 6
MSSVAILGGG ISGLSAAYYL ARMAPPTTKI TLIEGKKRLG GWIESRRVTP GHYDNIHQLP   60
```

```
KNNSKENTIL FEAGPRTLRP EGSNGAILLE MIRHLELNNE NLMSVSKSHP SARHRYIYYK  120
DKINTLPSDL QSFLLNKPPV LKSVPLAALL EPLKPSRFDK DGIAKDGIQD ESIYSFMTRR  180
FNEHTAIHLM GAVIHGIYAG DIKSLSLQST LRSLYEAERI YGSAVLGMMK GASQVTTSVR  240
ERGMAARSRK EDPEWFGRME KMSVIGFKSG MDTLPHQITS WLEQCPNVEV ITDDPAEHIE  300
IAHENKIKTQ KGKTVHADHI ISTLPSPVLE RLVQHQPVLP HLSYNPSADV AVVNLAYSPD  360
EMKLQYDGFG FLTPHRDTPY GNPLPGTLGV VFDSNALPIE SERAVKLTAM IGGSDWKDAF  420
GNVPIDELEP KVALDYTRKA VGTFLDIHAE PRYSMVNLQK QCIPQYLVGH QDRMLSLHHA  480
IKKNYGHALS VSGASYLGVS VPDCIKNSRM LVEELLVSGA LGSRQKVVTG LGKLEEQPTV  540
DEMRDNARLS RGNTSVIMKS                                             560

SEQ ID NO: 7          moltype = AA  length = 624
FEATURE               Location/Qualifiers
source                1..624
                      mol_type = protein
                      organism = Penicillium sp.
SEQUENCE: 7
MRLLTASKGL RSPQKPLISA IRCQHRAYNA AVIGGGITGL TAAWQLIQDR ECSSVTIYEK  60
SRRLGGWLQS ETIPVEGGEV VFEYGPRTLR SAMPASLPLL YLVSNLGLFD ELITTSKRSP  120
AALNRYIYYP DHLVRLPSPD PDLSLMENAR NIFRTITTEP LFEGFITGLL SEPNKPARPQ  180
EEWAIDESLA EFITRRFNRK IADNLVSAVM HGIYAGNIDE MSAQAIMGPL RNLEDGGILF  240
GLLIKSIMGK KTRSMDDFLA VDAVYKTPET MQRLDEINRV VKTASTFTFK RGTQQLVEGL  300
TRALRTSEKV RLVMDADILA LDPPANRGHK LKIYTGIRGE ESFDHVISAI SAPAMARILD  360
PQGQVKIDCD PEDEYRALWN SKKARHPKPN IGTVSGLHFF RHATTVMVVN LYYKTPNLLP  420
VDGFGYLIPR SIPYEQNPEC GLGVIFASAS SSGESPVAPY PKVSQDSAPG TKITIMFGGH  480
YWDGWKKQDY PDHKTAVRMA KDMLERHLGI TEPPALVRTR LQENAIPKYT PLHIHQIYAL  540
SRWAKEEYHN RLVLVGNSFS GVGVGDCVRQ GIMAATHGVG RHKLTATPRL KSKDWCPWKE  600
YNYQHWDLKG GVTTAPVRLF ESDI                                        624

SEQ ID NO: 8          moltype = AA  length = 636
FEATURE               Location/Qualifiers
source                1..636
                      mol_type = protein
                      organism = synthetic construct
SEQUENCE: 8
MELSLLRPTT QSLLPSFSKP NLRLNVYKPL RLRCSVAGGM RLPCASSRVF RQVRAPLALL  60
SRGQRHAVHT KQFDAAVIGG GITGLTAAYQ LSRDPSCSKV TLYEKSPHLG GWLSSEQIPV  120
PGGHVVFEYG PRTLRTSSPS CLPMMDLIMN LDLLDDVLIC DKKSPAAQNR YIYYPDHLVR  180
LPFPPTEGLL KTAWTLLMEP LFETFLYSAI FEKPKRAENT HILSRDESVA DFVSRRFSPK  240
ISENLASAVM AGIFAGDVNR LSAEMAIGYV RELEKRYGSI VDGMMTQRAS EMRAMPMDEL  300
LALESVAVPS HSDDRYWKSL RAVVSDASVL TLKNGLGQLT DAMAAQLRSS RNVEVVTGTE  360
VTSLSQNPKT QDLTIGFGKN ESKTHNRVIA THAPSSLARQ IQNTKVGVVP SDTIRDLGQN  420
NYAVTVMVVN LYYEDPDLVP VEGFGYLLPS SVPFEQNPER ALGVIFGSQS SEGQDTAPGT  480
KLTVMMGGHL WDGWSESDYP DPDKAIEMAQ ALLHRHLGIK TAPSVARARL LRDAIPQYTV  540
GHLSRMKELS HSVRSDFHKR LTLAGAWYGT VGIGVVDCIR QGYLASSYGV GSKKLGPGNS  600
RRPWTKHDFH NWELEGGIAT SPVRLDNVHV TERQHY                           636

SEQ ID NO: 9          moltype = AA  length = 636
FEATURE               Location/Qualifiers
source                1..636
                      mol_type = protein
                      organism = synthetic construct
SEQUENCE: 9
MELSLLRPTT QSLLPSFSKP NLRLNVYKPL RLRCSVAGGM RLPCASSRAF RQVRAPLALL  60
HRGQRHAVHT KQFDAAVIGG GITGLTAAYQ LSRDPSCSKV TLYEKSSHLG GWLSSEQIPV  120
PGGHVVFEYG PRTLRTSSPS CLPMMDLIMN LDLLDDVLIC DKKSPAAQNR YIYYPDHLVR  180
LPFPPTEGLL KTAWTLLMEP LFETFLYSAI FEKPKRAENT HILSRDESVA DFVSRRFSPK  240
ISENLASAVM AGIFAGDVNR LSAEMAIGYV RELEKRYGSI VDGMMTQRAS EMRAMPMDEL  300
LALESVAVPS HSDDRYWKSL RAVVTDASVL TLKNGLGQLT DAMAAQLRSS RNVEVVTGTE  360
VTSLSQNPKT QDLTIGFGKN ESRTHNRVIA THAPSSLARQ IQNTKVGVVP SDTIRDLGQN  420
NYAVTVMVVN LYYEDPDLVP VEGFGYLLPS SVPFEQNPER ALGVIFGSQS SEGQDTAPGT  480
KLTVIMGGHL WDGWSESDYP DPDKAIEMAQ ALLHRHLGIK TAPSVARARL LRDAIPQYTV  540
GHLSRMKELS HSVRSDFHKR LTLAGAWYGT VGIGVVDCIR QGYLASSYGV GSKKLGPGNS  600
RRPWTKHDFH NWELEGGIAT SPVRFDNVHV TERQHY                           636

SEQ ID NO: 10         moltype = AA  length = 634
FEATURE               Location/Qualifiers
source                1..634
                      mol_type = protein
                      organism = synthetic construct
SEQUENCE: 10
MELSLLRPTT QSLLPSFSKP NLRLNVYKPL RLRCSVAGGM SRRRAESTAV ALLSSPAKSH  60
LQPPLRRLDG IRSLSTSSAL ARRRPIVACN YTQSFNNGRT FVSQAKDANI AVLGGGLTGL  120
TAAYLAKKL PSTAKITLYE SSDRLGGWIK TDRVPVDIEG KSGTLSFERG ARSLSSLVGN  180
TFRFDDLVLY DLALDLGLAI NSPSQQPRYI YYPDHLVPTP PNISIFDMLR EPLYLEIIGA  240
SLGLGINSLR KRTLPSKDYS VSEWLYAVSN SRKGIGNLAS AMMHGIYGGD IHKLSARCVL  300
DRLYWGWYLP NPGLSVRPMP VAEQALLETL GQDKQIQKMA LEPRSALVDF GDKGMESLPQ  360
ALSAALREQP NITIKTGEAV QDVVYNKANQ QVHITSSNAK DNSKHNSKVY DKVISTLSAQ  420
DIALLAGNKL PSLSTAHSVS VMTVNIWFPQ ENLKPPGFGY LIPNSVAPEL NPEHALGVFF  480
DSDVQTRSKD EPAGTKLFVL MGGHYYDRPD VTPPTEEEAI IQARNLLERH LGIPRDAPAY  540
```

-continued

```
ATANFARECI PQHYVGHQDR LKAAHTELTR NFGGRLAVAG GSFTRIGAVA SLRAGYDAAT    600
AAKKGLEATG LEYLNDIQQF SVVATSHIPV RHFK                                634

SEQ ID NO: 11          moltype = AA   length = 634
FEATURE                Location/Qualifiers
source                 1..634
                       mol_type = protein
                       organism = synthetic construct
SEQUENCE: 11
MELSLLRPTT QSLLPSFSKP NLRLNVYKPL RLRCSVAGGM SRRRAESTAV ALLSSPAKSH    60
LQPPLRRLDG IRSLSTSSAL ARRRPIVACN YTQSFNNGRT FVSQAKDANI AVLGGGLTGL    120
TAAYYLAKKL PSTAKITLYE SSDRLGGWIK TDRVPVDIEG KSGTLSFERG ARSLSSLVGN    180
TFRFDDLVLY DLALDLGLAI NSPSQQPRYI YYPDHLVPTP PNISIFDMLR EPLYLEIIGA    240
SLGLGINSLR KRTLPSKDYS VSEWLYAVSN SRKGIGNLAS AMMHGIYGGD IHKLSARCVL    300
DRLYWGWYLP NPGLSVRPMP VAEQALLETL GQDKQIQKMA LEPRSALVDF GDKGMESLPQ    360
ALSAALREQP NITIKTGEAV QDVVYNKANQ QVHITSSNAK DNSKHNSKVY DKVISTLSAQ    420
DIALLAGNKL PSLSTAHSVS VMTVNIWFPQ ENLKPPGFGY LIPNSVAPEL NPEHALGVFF    480
DSDVQTRSKD EPAGTKLFVL MGGHYYDRPD VTPPTEEEAI IQARNLPERH LGIPRDAPAY    540
ATANFARECI PQHYVGHQDR LKAAHTELTR NFGGRLAVAG GSFTRIGAVA SLRAGYDAAT    600
AAKKGLEATG LEYLNDIQQF SVVATSHIPV RHFK                                634

SEQ ID NO: 12          moltype = AA   length = 634
FEATURE                Location/Qualifiers
source                 1..634
                       mol_type = protein
                       organism = synthetic construct
SEQUENCE: 12
MELSLLRPTT QSLLPSFSKP NLRLNVYKPL RLRCSVAGGM SRRRAESTAV ALLSSPAKSH    60
LQPPLRRLDG IRSLSTSSAL ARRRPIVACN YTQSFNNGRT FVSQAKDANI AVLGGGLTGL    120
TAAYYLAKKL PSTAKITLYE SSDRLGGWIK TDRVPVDIEG KSGTLSFERG ARSLSSLVGN    180
TFRFDDLVLY DLALDLGLAI NSPSQQPRYI YYPDHLVPTP PNISIFDMLR EPLYLEIIGA    240
SLGLGINSVR KRTLPSKDYS VSEWLYAVSN SRKGIGNLAS AMMHGIYGGD IHKLSARCVL    300
DRLYWGWYLP NPGLSVRPMP VAEQALLETL GQDKQIQKMA LEPRSALVDF GDKGMESLPQ    360
ALSAALREQP NITIKTGEAV QDVVYNKANQ QVHITSSNAK DNSKHNSKVY DKVISTLSAQ    420
DIALLAGNKL PSLSTAHSVS VMTVNIWFPQ ENLKPPGFGY LIPNSVAPEL NPEHALGVFF    480
DSDVQTRSKD EPAGTKLFVL MGGHYYDRPD VTPPTEEEAI IQARNLLERH LGIPRDAPAY    540
ATANFARECI PQHYVGHQDR LKAAHTELTR NFGGRLAVAG GSFTRIGAVA SLRAGYDAAT    600
AAKKGLEATG LEYLNDIQQF SVVATSQIPV RHFK                                634

SEQ ID NO: 13          moltype = AA   length = 599
FEATURE                Location/Qualifiers
source                 1..599
                       mol_type = protein
                       organism = synthetic construct
SEQUENCE: 13
MELSLLRPTT QSLLPSFSKP NLRLNVYKPL RLRCSVAGGM SSVAILGGGI SGLSAAYYLA    60
RMAPPTTKIT LIEGKKRLGG WIESRRVTPG HYDNIHQLPK NNSKENTILF EAGPRTLRPE    120
GSNGAILLEM IRHLELNNEN LMSVSKSHPS ARHRYIYYKD KINTLPSDLQ SFLLNKPPVL    180
KSVPLAALLE PLKPSRFDKD GIAKDGIQDE SIYSFMTRRF NEHTAIHLMG AVIHGIYAGD    240
IKSLSLQSTL RSLYEAERIY GSAVLGMMKG ASQVTTSVRE RGMAARSRKE DPEWFGRMEK    300
MSVIGFKSGM DTLPHQITSW LEQCPNVEVI TDDPAEHIEI AHENKIKTQK GKTVHADHII    360
STLPSPVLER LVQHQPVLPH LSYNPSADVA VVNLAYSPDE MKLQYDGFGF LTPHRDTPYG    420
NPLPGTLGVV FDSNALPIES ERAVKLTAMI GGSDWKDAFG NVPIDELEPK VALDYTRKAV    480
GTFLDIHAEP RYSMVNLQKQ CIPQYLVGHQ DRMLSLHHAI KKNYGHALSV SGASYLGVSV    540
PDCIKNSRML VEELLVSGAL GSRQKVVTGL GKLEEQPTVD EMRDNARLSR GNTSVIMKS     599

SEQ ID NO: 14          moltype = AA   length = 663
FEATURE                Location/Qualifiers
source                 1..663
                       mol_type = protein
                       organism = synthetic construct
SEQUENCE: 14
MELSLLRPTT QSLLPSFSKP NLRLNVYKPL RLRCSVAGGM RLLTASKGLR SPQKPLISAI    60
RCQHRAYNAA VIGGGITGLT AAWQLIQDRE CSSVTIYEKS RRLGGWLQSE TIPVEGGEVV    120
FEYGPRTLRS AMPASLPLLY LVSNLGLFDE LITTSKRSPA ALNRYIYYPD HLVRLPSPDP    180
DLSLMENARN IFRTITTEPL FEGFITGLLS EPNKPARPQE EWAIDESLAE FITRRFNRKI    240
ADNLVSAVMH GIYAGNIDEM SAQAIMGPLR NLEDGGILFG LLIKSIMGKK TRSMDDFLAV    300
DAVYKTPETM QRLDEINRVV KTASTFTFKR GTQQLVEGLT RALRTSEKVR LVMDADILAL    360
DPPANRGHKL KIYTGIRGEE SFDHVISAIS APAMARILDP QGQVKIDCDP EDEYRALWNS    420
KKARHPKPNI GTVSGLHFFR HATTVMVVNL YYKTPNLLPV DGFGYLIPRS IPYEQNPECG    480
LGVIFASASS SGESPVAPYP KVSQDSAPGT KITIMFGGHY WDGWKKQDYP DHKTAVRMAK    540
DMLERHLGIT EPPALVRTRL QENAIPKYTP LHIHQIYALS RWAKEEYHNR LVLVGNSFSG    600
VGVGDCVRQG IMAATHGVGR HKLTATPRLK SKDWCPWKEY NYQHWDLKGG VPTAPVRLFE    660
SDI                                                                 663

SEQ ID NO: 15          moltype = AA   length = 39
FEATURE                Location/Qualifiers
source                 1..39
                       mol_type = protein
```

```
                              organism = Arabidopsis thaliana
SEQUENCE: 15
MELSLLRPTT QSLLPSFSKP NLRLNVYKPL RLRCSVAGG                                    39

SEQ ID NO: 16            moltype = AA  length = 22
FEATURE                  Location/Qualifiers
source                   1..22
                         mol_type = protein
                         organism = Aspergillus sp.
SEQUENCE: 16
AYQLSRDPSC SKVTLYEKSP HL                                                      22

SEQ ID NO: 17            moltype = AA  length = 22
FEATURE                  Location/Qualifiers
source                   1..22
                         mol_type = protein
                         organism = Aspergillus sp.
SEQUENCE: 17
AYQLSRDPSC SKVTLYEKSS HL                                                      22

SEQ ID NO: 18            moltype = AA  length = 23
FEATURE                  Location/Qualifiers
source                   1..23
                         mol_type = protein
                         organism = Fusarium sp.
SEQUENCE: 18
AYYLAKKLPS TAKITLYESS DRL                                                     23

SEQ ID NO: 19            moltype = AA  length = 23
FEATURE                  Location/Qualifiers
source                   1..23
                         mol_type = protein
                         organism = Fusarium sp.
SEQUENCE: 19
AYYLAKKLPS TAKITLYESS DRL                                                     23

SEQ ID NO: 20            moltype = AA  length = 23
FEATURE                  Location/Qualifiers
source                   1..23
                         mol_type = protein
                         organism = Rhizopus sp.
SEQUENCE: 20
AYYLARMAPP TTKITLIEGK KRL                                                     23

SEQ ID NO: 21            moltype = AA  length = 22
FEATURE                  Location/Qualifiers
source                   1..22
                         mol_type = protein
                         organism = Penicillium sp.
SEQUENCE: 21
AWQLIQDREC SSVTIYEKSR RL                                                      22

SEQ ID NO: 22            moltype = AA  length = 23
FEATURE                  Location/Qualifiers
source                   1..23
                         mol_type = protein
                         organism = Fusarium sp.
SEQUENCE: 22
AYYLAKKLPS TAKITLYESS DRL                                                     23

SEQ ID NO: 23            moltype = AA  length = 18
FEATURE                  Location/Qualifiers
source                   1..18
                         mol_type = protein
                         organism = Aspergillus sp.
SEQUENCE: 23
GWLSSEQIPV PGGHVVFE                                                           18

SEQ ID NO: 24            moltype = AA  length = 18
FEATURE                  Location/Qualifiers
source                   1..18
                         mol_type = protein
                         organism = Aspergillus sp.
SEQUENCE: 24
GWLSSEQIPV PGGHVVFE                                                           18

SEQ ID NO: 25            moltype = AA  length = 22
FEATURE                  Location/Qualifiers
source                   1..22
```

-continued

```
                          mol_type = protein
                          organism = Fusarium sp.
SEQUENCE: 25
GWIKTDRVPV DIEGKSGTLS FE                                      22

SEQ ID NO: 26            moltype = AA   length = 22
FEATURE                  Location/Qualifiers
source                   1..22
                         mol_type = protein
                         organism = Fusarium sp.
SEQUENCE: 26
GWIKTDRVPV DIEGKSGTLS FE                                      22

SEQ ID NO: 27            moltype = AA   length = 32
FEATURE                  Location/Qualifiers
source                   1..32
                         mol_type = protein
                         organism = Rhizopus sp.
SEQUENCE: 27
GWIESRRVTP GHYDNIHQLP KNNSKENTIL FE                           32

SEQ ID NO: 28            moltype = AA   length = 18
FEATURE                  Location/Qualifiers
source                   1..18
                         mol_type = protein
                         organism = Penicillium sp.
SEQUENCE: 28
GWLQSETIPV EGGEVVFE                                           18

SEQ ID NO: 29            moltype = AA   length = 22
FEATURE                  Location/Qualifiers
source                   1..22
                         mol_type = protein
                         organism = Fusarium sp.
SEQUENCE: 29
GWIKTDRVPV DIEGKSGTLS FE                                      22

SEQ ID NO: 30            moltype = AA   length = 16
FEATURE                  Location/Qualifiers
source                   1..16
                         mol_type = protein
                         organism = Aspergillus sp.
SEQUENCE: 30
QNRYIYYPDH LVRLPF                                             16

SEQ ID NO: 31            moltype = AA   length = 16
FEATURE                  Location/Qualifiers
source                   1..16
                         mol_type = protein
                         organism = Aspergillus sp.
SEQUENCE: 31
QNRYIYYPDH LVRLPF                                             16

SEQ ID NO: 32            moltype = AA   length = 16
FEATURE                  Location/Qualifiers
source                   1..16
                         mol_type = protein
                         organism = Fusarium sp.
SEQUENCE: 32
QPRYIYYPDH LVPTPP                                             16

SEQ ID NO: 33            moltype = AA   length = 16
FEATURE                  Location/Qualifiers
source                   1..16
                         mol_type = protein
                         organism = Fusarium sp.
SEQUENCE: 33
QPRYIYYPDH LVPTPP                                             16

SEQ ID NO: 34            moltype = AA   length = 16
FEATURE                  Location/Qualifiers
source                   1..16
                         mol_type = protein
                         organism = Rhizopus sp.
SEQUENCE: 34
RHRYIYYKDK INTLPS                                             16

SEQ ID NO: 35            moltype = AA   length = 16
FEATURE                  Location/Qualifiers
```

-continued

```
source                    1..16
                          mol_type = protein
                          organism = Penicillium sp.
SEQUENCE: 35
LNRYIYYPDH LVRLPS                                            16

SEQ ID NO: 36             moltype = AA   length = 16
FEATURE                   Location/Qualifiers
source                    1..16
                          mol_type = protein
                          organism = Fusarium sp.
SEQUENCE: 36
QPRYIYYPDH LVPTPP                                            16

SEQ ID NO: 37             moltype = AA   length = 15
FEATURE                   Location/Qualifiers
source                    1..15
                          mol_type = protein
                          organism = Aspergillus sp.
SEQUENCE: 37
PKISENLASA VMAGI                                             15

SEQ ID NO: 38             moltype = AA   length = 15
FEATURE                   Location/Qualifiers
source                    1..15
                          mol_type = protein
                          organism = Aspergillus sp.
SEQUENCE: 38
PKISENLASA VMAGI                                             15

SEQ ID NO: 39             moltype = AA   length = 15
FEATURE                   Location/Qualifiers
source                    1..15
                          mol_type = protein
                          organism = Fusarium sp.
SEQUENCE: 39
RKGIGNLASA MMHGI                                             15

SEQ ID NO: 40             moltype = AA   length = 15
FEATURE                   Location/Qualifiers
source                    1..15
                          mol_type = protein
                          organism = Fusarium sp.
SEQUENCE: 40
RKGIGNLASA MMHGI                                             15

SEQ ID NO: 41             moltype = AA   length = 15
FEATURE                   Location/Qualifiers
source                    1..15
                          mol_type = protein
                          organism = Rhizopus sp.
SEQUENCE: 41
EHTAIHLMGA VIHGI                                             15

SEQ ID NO: 42             moltype = AA   length = 15
FEATURE                   Location/Qualifiers
source                    1..15
                          mol_type = protein
                          organism = Penicillium sp.
SEQUENCE: 42
RKIADNLVSA VMHGI                                             15

SEQ ID NO: 43             moltype = AA   length = 15
FEATURE                   Location/Qualifiers
source                    1..15
                          mol_type = protein
                          organism = Fusarium sp.
SEQUENCE: 43
RKGIGNLASA MMHGI                                             15

SEQ ID NO: 44             moltype = AA   length = 19
FEATURE                   Location/Qualifiers
source                    1..19
                          mol_type = protein
                          organism = Aspergillus sp.
SEQUENCE: 44
GDVNRLSAEM AIGYVRELE                                         19

SEQ ID NO: 45             moltype = AA   length = 19
```

-continued

| FEATURE | Location/Qualifiers | |
|---|---|---|
| source | 1..19 | |
| | mol_type = protein | |
| | organism = Aspergillus sp. | |
| SEQUENCE: 45 | | |
| GDVNRLSAEM AIGYVRELE | | 19 |

| SEQ ID NO: 46 | moltype = AA  length = 19 | |
|---|---|---|
| FEATURE | Location/Qualifiers | |
| source | 1..19 | |
| | mol_type = protein | |
| | organism = Fusarium sp. | |
| SEQUENCE: 46 | | |
| GDIHKLSARC VLDRLYWGW | | 19 |

| SEQ ID NO: 47 | moltype = AA  length = 19 | |
|---|---|---|
| FEATURE | Location/Qualifiers | |
| source | 1..19 | |
| | mol_type = protein | |
| | organism = Fusarium sp. | |
| SEQUENCE: 47 | | |
| GDIHKLSARC VLDRLYWGW | | 19 |

| SEQ ID NO: 48 | moltype = AA  length = 19 | |
|---|---|---|
| FEATURE | Location/Qualifiers | |
| source | 1..19 | |
| | mol_type = protein | |
| | organism = Rhizopus sp. | |
| SEQUENCE: 48 | | |
| GDIKSLSLQS TLRSLYEAE | | 19 |

| SEQ ID NO: 49 | moltype = AA  length = 19 | |
|---|---|---|
| FEATURE | Location/Qualifiers | |
| source | 1..19 | |
| | mol_type = protein | |
| | organism = Penicillium sp. | |
| SEQUENCE: 49 | | |
| GNIDEMSAQA IMGPLRNLE | | 19 |

| SEQ ID NO: 50 | moltype = AA  length = 19 | |
|---|---|---|
| FEATURE | Location/Qualifiers | |
| source | 1..19 | |
| | mol_type = protein | |
| | organism = Fusarium sp. | |
| SEQUENCE: 50 | | |
| GDIHKLSARC VLDRLYWGW | | 19 |

| SEQ ID NO: 51 | moltype = AA  length = 14 | |
|---|---|---|
| FEATURE | Location/Qualifiers | |
| source | 1..14 | |
| | mol_type = protein | |
| | organism = Aspergillus sp. | |
| SEQUENCE: 51 | | |
| GLGQLTDAMA AQLR | | 14 |

| SEQ ID NO: 52 | moltype = AA  length = 14 | |
|---|---|---|
| FEATURE | Location/Qualifiers | |
| source | 1..14 | |
| | mol_type = protein | |
| | organism = Aspergillus sp. | |
| SEQUENCE: 52 | | |
| GLGQLTDAMA AQLR | | 14 |

| SEQ ID NO: 53 | moltype = AA  length = 14 | |
|---|---|---|
| FEATURE | Location/Qualifiers | |
| source | 1..14 | |
| | mol_type = protein | |
| | organism = Fusarium sp. | |
| SEQUENCE: 53 | | |
| GMESLPQALS AALR | | 14 |

| SEQ ID NO: 54 | moltype = AA  length = 14 | |
|---|---|---|
| FEATURE | Location/Qualifiers | |
| source | 1..14 | |
| | mol_type = protein | |
| | organism = Fusarium sp. | |
| SEQUENCE: 54 | | |
| GMESLPQALS AALR | | 14 |

-continued

```
SEQ ID NO: 55            moltype = AA  length = 14
FEATURE                  Location/Qualifiers
source                   1..14
                         mol_type = protein
                         organism = Rhizopus sp.
SEQUENCE: 55
GMDTLPHQIT SWLE                                                    14

SEQ ID NO: 56            moltype = AA  length = 14
FEATURE                  Location/Qualifiers
source                   1..14
                         mol_type = protein
                         organism = Penicillium sp.
SEQUENCE: 56
GTQQLVEGLT RALR                                                    14

SEQ ID NO: 57            moltype = AA  length = 14
FEATURE                  Location/Qualifiers
source                   1..14
                         mol_type = protein
                         organism = Fusarium sp.
SEQUENCE: 57
GMESLPQALS AALR                                                    14

SEQ ID NO: 58            moltype = AA  length = 26
FEATURE                  Location/Qualifiers
source                   1..26
                         mol_type = protein
                         organism = Aspergillus sp.
SEQUENCE: 58
GQNNYAVTVM VVNLYYEDPD LVPVEG                                       26

SEQ ID NO: 59            moltype = AA  length = 26
FEATURE                  Location/Qualifiers
source                   1..26
                         mol_type = protein
                         organism = Aspergillus sp.
SEQUENCE: 59
GQNNYAVTVM VVNLYYEDPD LVPVEG                                       26

SEQ ID NO: 60            moltype = AA  length = 24
FEATURE                  Location/Qualifiers
source                   1..24
                         mol_type = protein
                         organism = Fusarium sp.
SEQUENCE: 60
STAHSVSVMT VNIWFPQENL KPPG                                         24

SEQ ID NO: 61            moltype = AA  length = 24
FEATURE                  Location/Qualifiers
source                   1..24
                         mol_type = protein
                         organism = Fusarium sp.
SEQUENCE: 61
STAHSVSVMT VNIWFPQENL KPPG                                         24

SEQ ID NO: 62            moltype = AA  length = 26
FEATURE                  Location/Qualifiers
source                   1..26
                         mol_type = protein
                         organism = Rhizopus sp.
SEQUENCE: 62
SYNPSADVAV VNLAYSPDEM KLQYDG                                       26

SEQ ID NO: 63            moltype = AA  length = 26
FEATURE                  Location/Qualifiers
source                   1..26
                         mol_type = protein
                         organism = Penicillium sp.
SEQUENCE: 63
HFFRHATTVM VVNLYYKTPN LLPVDG                                       26

SEQ ID NO: 64            moltype = AA  length = 24
FEATURE                  Location/Qualifiers
source                   1..24
                         mol_type = protein
                         organism = Fusarium sp.
SEQUENCE: 64
STAHSVSVMT VNIWFPQENL KPPG                                         24
```

-continued

```
SEQ ID NO: 65          moltype = AA  length = 21
FEATURE                Location/Qualifiers
source                 1..21
                       mol_type = protein
                       organism = Aspergillus sp.
SEQUENCE: 65
GVIFGSQSSE GQDTAPGTKL T                                                   21

SEQ ID NO: 66          moltype = AA  length = 21
FEATURE                Location/Qualifiers
source                 1..21
                       mol_type = protein
                       organism = Aspergillus sp.
SEQUENCE: 66
GVIFGSQSSE GQDTAPGTKL T                                                   21

SEQ ID NO: 67          moltype = AA  length = 22
FEATURE                Location/Qualifiers
source                 1..22
                       mol_type = protein
                       organism = Fusarium sp.
SEQUENCE: 67
GVFFDSDVQT RSKDEPAGTK LF                                                  22

SEQ ID NO: 68          moltype = AA  length = 22
FEATURE                Location/Qualifiers
source                 1..22
                       mol_type = protein
                       organism = Fusarium sp.
SEQUENCE: 68
GVFFDSDVQT RSKDEPAGTK LF                                                  22

SEQ ID NO: 69          moltype = AA  length = 20
FEATURE                Location/Qualifiers
source                 1..20
                       mol_type = protein
                       organism = Rhizopus sp.
SEQUENCE: 69
GVVFDSNALP IESERAVKLT                                                     20

SEQ ID NO: 70          moltype = AA  length = 32
FEATURE                Location/Qualifiers
source                 1..32
                       mol_type = protein
                       organism = Penicillium sp.
SEQUENCE: 70
GVIFASASSS GESPVAPYPK VSQDSAPGTK IT                                       32

SEQ ID NO: 71          moltype = AA  length = 22
FEATURE                Location/Qualifiers
source                 1..22
                       mol_type = protein
                       organism = Fusarium sp.
SEQUENCE: 71
GVFFDSDVQT RSKDEPAGTK LF                                                  22

SEQ ID NO: 72          moltype = AA  length = 22
FEATURE                Location/Qualifiers
source                 1..22
                       mol_type = protein
                       organism = Aspergillus sp.
SEQUENCE: 72
YPDPDKAIEM AQALLHRHLG IK                                                  22

SEQ ID NO: 73          moltype = AA  length = 22
FEATURE                Location/Qualifiers
source                 1..22
                       mol_type = protein
                       organism = Aspergillus sp.
SEQUENCE: 73
YPDPDKAIEM AQALLHRHLG IK                                                  22

SEQ ID NO: 74          moltype = AA  length = 23
FEATURE                Location/Qualifiers
source                 1..23
                       mol_type = protein
                       organism = Fusarium sp.
SEQUENCE: 74
```

-continued

```
TPPTEEEAII QARNLLERHL GIP                                        23

SEQ ID NO: 75          moltype = AA   length = 23
FEATURE                Location/Qualifiers
source                 1..23
                       mol_type = protein
                       organism = Fusarium sp.
SEQUENCE: 75
TPPTEEEAII QARNLPERHL GIP                                        23

SEQ ID NO: 76          moltype = AA   length = 23
FEATURE                Location/Qualifiers
source                 1..23
                       mol_type = protein
                       organism = Rhizopus sp.
SEQUENCE: 76
DELEPKVALD YTRKAVGTFL DIH                                        23

SEQ ID NO: 77          moltype = AA   length = 22
FEATURE                Location/Qualifiers
source                 1..22
                       mol_type = protein
                       organism = Penicillium sp.
SEQUENCE: 77
YPDHKTAVRM AKDMLERHLG IT                                         22

SEQ ID NO: 78          moltype = AA   length = 23
FEATURE                Location/Qualifiers
source                 1..23
                       mol_type = protein
                       organism = Fusarium sp.
SEQUENCE: 78
TPPTEEEAII QARNLLERHL GIP                                        23

SEQ ID NO: 79          moltype = AA   length = 17
FEATURE                Location/Qualifiers
source                 1..17
                       mol_type = protein
                       organism = Aspergillus sp.
SEQUENCE: 79
RMKELSHSVR SDFHKRL                                               17

SEQ ID NO: 80          moltype = AA   length = 17
FEATURE                Location/Qualifiers
source                 1..17
                       mol_type = protein
                       organism = Aspergillus sp.
SEQUENCE: 80
RMKELSHSVR SDFHKRL                                               17

SEQ ID NO: 81          moltype = AA   length = 17
FEATURE                Location/Qualifiers
source                 1..17
                       mol_type = protein
                       organism = Fusarium sp.
SEQUENCE: 81
RLKAAHTELT RNFGGRL                                               17

SEQ ID NO: 82          moltype = AA   length = 17
FEATURE                Location/Qualifiers
source                 1..17
                       mol_type = protein
                       organism = Fusarium sp.
SEQUENCE: 82
RLKAAHTELT RNFGGRL                                               17

SEQ ID NO: 83          moltype = AA   length = 17
FEATURE                Location/Qualifiers
source                 1..17
                       mol_type = protein
                       organism = Rhizopus sp.
SEQUENCE: 83
RMLSLHHAIK KNYGHAL                                               17

SEQ ID NO: 84          moltype = AA   length = 17
FEATURE                Location/Qualifiers
source                 1..17
                       mol_type = protein
                       organism = Penicillium sp.
```

```
SEQUENCE: 84
QIYALSRWAK EEYHNRL                                                       17

SEQ ID NO: 85          moltype = AA  length = 17
FEATURE                Location/Qualifiers
source                 1..17
                       mol_type = protein
                       organism = Fusarium sp.
SEQUENCE: 85
RLKAAHTELT RNFGGRL                                                       17

SEQ ID NO: 86          moltype = AA  length = 596
FEATURE                Location/Qualifiers
source                 1..596
                       mol_type = protein
                       organism = Trichoderma sp.
SEQUENCE: 86
MRLPCASSRV FRQVRAPLAL LRRGQRHALH TKQFDAAVIG GGITGLTAAY QLSRDPSCSK        60
VTLYEKSSHL GGWLSSEQIP VRGGHVVFEY GPRTLRTSAP SCLPMMDLIM NLDLLDDVLI        120
CDKKSPAAQN RYIYYPDHLV RLPFPPTEGL LKTAWTLLME PLFETFLQSA LFEKPKRAVD        180
GDVLSRDESV ADFVSRRFSP KMSENLASAV MAGIFAGDVN RLSADMAIGY VRELEKRYGS        240
IVDGMMTQRA SELRAMPMDE FLALESVAVP SHKDDRYWKS LRAVVSDASV LTLKNGLGQL        300
TDAMAAQLRS SNNVEVVSGT EVTSLSQNPE TRDLTIGFGK NESKTHNRVI ATHAPSSLAR        360
QLENTKVGVA PSDTLRALGQ NNYAVTVMVV NLYYEDPDLV PVQGFGYLLP SSIPFEENPE        420
RALGVIFGSQ SSEGQDTAPG TKLTVMMGGH LWDGWSESDY PDPDKAVEMA QALLHRHLGI        480
KTAPSVARAR LLRDAIPQYT VGHLSRMKEL SQSVRGDPHK RLTLAGAWYG TVGIGVVDCI        540
RQGYIASSFG VGSKKLGPGG GRRPWTKHDF HNWELEGGIC TSPVRFDNVH ITERQH          596

SEQ ID NO: 87          moltype = AA  length = 597
FEATURE                Location/Qualifiers
source                 1..597
                       mol_type = protein
                       organism = Aspergillus sp.
SEQUENCE: 87
MRLPCVPSCA LRGVRTPLAF ARIGQRYSST YDAAVIGGGI TGLTAAYRLS QDPNCSKITL        60
YEKAPRVGGW LLSEKIPVEG GNVVFEYGPR TLRTAVPSCL PLLDLLVELG LHDDVLLTSS        120
SSPAARNRYI YYPDHLVRMP APDPNAGPIE NITNPLFAML REPVFEGLIA SALLEPVRAP        180
PDHKTFNSDE SVADFVSRRL CPEVADNLVS ALFHGIYADI ISRLSAQTLL GTFRDLENDD        240
RRVIGGYINS LMSDVKLMAM DDLLALESVA HEKPGMYWKS LRTLVNKTSV LTLKDGLSQL        300
SDALVDALKK SKKVDVLANT DVKSITQNPM TDDLIVGSGQ DRSRIHNRVI ATIPAPELAN        360
KLATTTVKDQ KVPQSTIRNL QEHNYAVTVM VVNLYFPNPD LLPVSGFGYL IPRSIPYEQN        420
PERALGVIFG SDSSVGQDTA PGTKLTVMMG GHWWDGWKES DYPDHDTAVA MSRALLHRHL        480
GITDAPTLTS SRLQRNAIPQ YTVGHLSRMR ELSRSTRHEL NNRLTLAGSW YNGVGVTDCI        540
RQGYLAASFG VGARKLGPGD GDRPWRRFDY EKWELEGGIV TSPVRWAEVY RTERKHF        597

SEQ ID NO: 88          moltype = AA  length = 596
FEATURE                Location/Qualifiers
source                 1..596
                       mol_type = protein
                       organism = Aspergillus sp.
SEQUENCE: 88
MRLPHASSHA LKGSRLSLAL ARNGQRRSLH TPTYDAAVVG GGITGLTTAY RLSRDPKCSK        60
ITLYEKSKNV GGWLQSEKIP FKDGHVVFEY GPRTLRTALP SCLPLLDLLE ELDLLGEVLV        120
TSKTSAAALN RYIYYPDHLA RVPAPDPARG ALGNALSLMW SLFREPVFKS IFLGIYNDIQ        180
SPAPQKLKAD ESVGDFISRR LSPELADNLV SSVFHGIYAG DIYQLSAEAL LGQHREPEGG        240
VPSIMLRLIN EARMNHTPEL LDDQLAMELI LEEKSRSYLN ALAVLVRQAS VLTLRNGLGQ        300
LTDALLAALA KSKKVDILPE AEVTAISRNQ NSSNITISHG QDEHRMHNRV VSTIPAPHLA        360
KALRQGGGED KKLPHNTIQA LEEHNYAVTV MVVNLFYEKE DLLPVKGFGY LIPRSIPFEQ        420
NPERGLGVIF GSETSAGQDT VPGTKLTVML GGHLWDGWTE SDYPDHDTAV KMARTLLERH        480
LGITDAPAIS RSRLHRNAIP QYTVGHPARM DRISESARAD FSNRLSLAGS WYGGIGVVDC        540
IRHAYLTAAY GVSAQKLRSG GQDRPWKLFN YTQWELEGGI VKSPVRLVWR RPDSKN          596

SEQ ID NO: 89          moltype = AA  length = 601
FEATURE                Location/Qualifiers
source                 1..601
                       mol_type = protein
                       organism = Fusarium sp.
SEQUENCE: 89
MSHSRAESTA VALLSSAAHS TTKPHLRVPL CRLNGFRNLS TCSASALTRR RPIIACKHTQ        60
SSRDGRRYVS QAKDANIAVI GGGLTGLSAA YYLAKKLPST TKITLYEAND RLGGWIKTDR        120
VPVDIEGKKG IVSFERGSRS LTSLVGNTFR FDDLVLYDLT LDLGLSLNFP PARPRYVYYP        180
DHLVATPPNI SIFDILREPL YLESFGAGLG LMINQLRKRQ LPAEDESVAD WLYKVTNSRK        240
GIGNLASAMM HGIYGGDINK LSARSVLDRI YWGWYMPNPG LHARPMPLPE QLILETLGQD        300
RQIQKLALEP KSTLIDFGDK GMESLPQAIG AALRDQPNVT IMTGEAVNDI QYDEAKKQVQ        360
INSFNTQNEE KSNSQAYDKI VSTLSAQHIA RLAGDKVQSL SAAHSVSVMT VNIWFPQENL        420
KPPGFGYLIP DSVEPELNPE HALGVFFDSD VGTRSKDEPA GTKLFVLMGG HYYDRPGVTP        480
PTEDEAIVQA RNLLERHLGI PRDAPAYATA NFAKECIPQH NVGHQDLLRN AHAELKQNFG        540
GRLAVAGGSF HRIGTIASLR SGYDAAVATK NGLEATGLEY LETITEFAVV PTDMIPVRLF        600
K                                                                       601
```

-continued

```
SEQ ID NO: 90            moltype = AA  length = 595
FEATURE                  Location/Qualifiers
source                   1..595
                         mol_type = protein
                         organism = Fusarium sp.
SEQUENCE: 90
MSRRRAESTA VALLGSPAKP HLPLPLRRLD AIRSLSTSSA LTRRRPIVAR NYTQFFNNGR   60
TFVSQAKDAN IAVLGGGLTG LTAAYYLAKK LPSTAKITLY ESSDRLGGWI KTDRVPVDVE  120
GKSGTVSFER GARSLSSLAG NTFRFDDLVL YDLALDLGLV VNSPRQQPRY IYYPDHLVPM  180
PPNVSIFDIF REPLYLESIG ASLGLGINSL RKRTLPSKDY SVSEWLYAVS NSRKGVGTLA  240
SAMMHGIYGG DIDKLSARSV LDRVYWGWYL PNPGLSARPM PVAEQTLLET LGQDKQIQKM  300
ALEPRSALVD FGDKGMESLP QALSTALREQ PNVTIKTGEA VQDVVHNKTN QQVHVTSSNA  360
KNKSEHNSKV YDKVISTLSA QDIARLTGDK LPSLSTAHSV SVMTVNIWFP RENLKPPGFG  420
YLIPNSVAPE LNPEHALGVF FDSDVQTRSK DEPAGTKLFV LMGGHYYDRP DVTPPTEEEA  480
ILQARNLLER HLGIPRDAPA YATANFAREC IPQHYVGHQD RLRAAHTELT HNFGGRLAVA  540
GGSFTRIGAI ASLRAGYDAA TAAKEGLEAT GLEYLNDIQQ FSVVATSHIP VRHFK       595

SEQ ID NO: 91            moltype = AA  length = 560
FEATURE                  Location/Qualifiers
source                   1..560
                         mol_type = protein
                         organism = Rhizopus sp.
SEQUENCE: 91
MSSVAILGGG ISGLSAAYYL ARMAPPTTKI TLIEGKKRLG GWIESRRVTP GHYDNIHQLP   60
KNNSKENTIL FEAGPRTLRP EGSNGAILLE MIRHLELNNE NLMSVSKSHP SARHRYIYYK  120
DKINTLPSDL QSFLLNKPPV LKSVPLAALL EPLKPSRFDK DGIAKDGIED ESIYSFMTRR  180
FNEHTAIHLM GAVIHGIYAG DIKSLSLQST LRSLYEAERI YGSAVLGMMK GASQVTTSVR  240
ERGMAARSRK EDPEWFGRME KMSVIGFKSG MDTLPHQITS WLEQCPNVEV ITDDPAEHIE  300
IAHENKIKTQ KGKTVHADHI ISTLPSPVLE RLVQHQPVLP HLSYNPSADV AVVNLAYSPD  360
EMKLQYDGFG FLTPHRDTPY GNPLPGTLGV VFDSNALPIE SERAVKLTAM IGGSDWKDAF  420
GNVPIDELEP KVALDYTRKA VGTFLDIHAE PRYSMVNLQK QCIPQYLVGH QDRMLSLHHA  480
IKKNYGHALS VSGASYLGVS VPDCIKNSRM LVEELLVSGA LGSRQKVVTG LGKLEEQPTV  540
DEMRDNARLS RGNTSVIMKS                                             560

SEQ ID NO: 92            moltype = AA  length = 559
FEATURE                  Location/Qualifiers
source                   1..559
                         mol_type = protein
                         organism = Rhizopus sp.
SEQUENCE: 92
MSSIAVLGGG ISGLSAAYYL ARLAPASTKI VLIEGKDRLG GWIHSRRVAP GKYSRDKAPQ   60
LSNEKDSILF EAGPRSLRPE GPNGAILLEM IQNLDLNNEG LLSVPKTDPS VKNRYIYYDG  120
EINTLPSGPI SMLLKKPPVF KSVILAGALE PLRSSRFKNG KPKDGIEDES MYNFMKRRFN  180
EHTAINLMGA VAHGVYAGDV KQLSIQSTLR MLYEAEKNYG SVIVGMMRGA ANTSTMRERG  240
MAVRSRDKDP EWFGRMEKMS VLGFKDGMET LPDRLCSWLE QRPNVEIIRN DPVESIEPLE  300
NGKESKIKTK SNEFFADHVL STIPSFTLEK LIKPNSLPNL SHNPASDVAV VNFAYSPEVK  360
LGYDGFGFLT PHRDTKYRVP VPGTLGVIFD SNAMPGQETE QPEVVKVTAM MGGADWKDAF  420
GKATIDELDP EVAYKYARKG MSVFLNLHDE PTHAMVNLQK QCIPQYVVGH EGRMRELHHA  480
LKQNYGHLMS LTGASYMGVS VPDCIKNSRM LVEELLVSGA LGSRDKVVTG LGRTVESNSK  540
ELQDGARISK GTVDVIMKS                                              559

SEQ ID NO: 93            moltype = AA  length = 550
FEATURE                  Location/Qualifiers
source                   1..550
                         mol_type = protein
                         organism = Rhizopus sp.
SEQUENCE: 93
MSAVILGGGI SGLSAAYYLA RMAPSTTKIT LIEGKNRLGG WIESRRVTAG HYDNIHCLPK   60
ENQQNTVLFE AGPRTLRPEG TNGAILLEMI RHLDLNNDDL LSIPKSHPSA KNRYIYYQDK  120
INKLPSDFGS FLRQRPPVLK SVPLAGLLEP LRTSRFENGL PKNGEEDESI YSFISRRFNE  180
HTATHLMGAV IHGIYAGDVR ALSLQSTLNS LYEAERTYGS AVLGMLKGVS QATQTMRERG  240
MAARSRKDDP DWFGRMEKMS VIGFKTGMDS LPDKITAWLK QRPNVEIITH DSVQHIGEGK  300
IKTEHREIEA DHIISTLPSS VLHSLLSRPL PHLMHNPAVD VAVVNLAYPS DIKLDYDGFG  360
FLTPHRDSKY PNPVPGTLGV VFDSNSLPID SEHATKLTVM MGGSDWKDAF GDVSLDQLDP  420
QVALQRARQA VSTFLGIHAE PHASMVHLQK QCIPQYLVGH RQRMRSLHHA IKQDYGHSLS  480
VSGASYLGVS VPDCIKNSRM LVEELLVSGA LGSRQKIVTG LGRLEQEMTV EEMRDNARVS  540
KSNTSVIIKS                                                       550

SEQ ID NO: 94            moltype = AA  length = 624
FEATURE                  Location/Qualifiers
source                   1..624
                         mol_type = protein
                         organism = Penicillium sp.
SEQUENCE: 94
MRLLTASKGL RSPQKPLISA IRCQHRSYNA AVIGGGITGL TAAWQLIQDR ECSSVTIYEK   60
SRRLGGWLQS ETIPVEGGEV VFEYGPRTLR SAMPASLPLL YLVSNLGLFD ELITTSKRSP  120
AALNRYIYYP DHLVRLPTPD PDLSMENAR NIFRTITTEP LFEGFITGLL SEPNKPARPQ  180
EEWAIDESLA EFITRRFNRK IADNLVSAVM HGIYADNIDE MSAQAIMGPL RNLEDGGILF  240
```

-continued

```
GLLIKSIMGK KTRSMDDFLA VDAVYKTPET MQRLDEINRV VKTASTFTFK RGTQQLVEGL  300
TRALRASEKV RLVMDADILA LDPPANRGHK LKIYTGIRGE ESFDHVISAI SAPAMARILD  360
PQGQVKIDCD PEDEYRALWN SKKARHPKPN IGTVSGLHFF RHATTVMVVN LYYKTPNLLP  420
VDGFGYLIPR SIPYEQNPEC GLGVIFASAS SSGESPVAPY PKVSQDSAPG TKITIMFGGH  480
YWDGWKKQDY PDHKTAVRMA KDMLERHLGI TEPPALVRTR LQENAIPKYK PPHIHQIYAL  540
SRWAKEEYHN RLVLVGNSFS GVGVGDCVRQ GIMAATHGVG RHKLTATPRL ESKDWCPWKE  600
YNYQHWDLKG GVPTAPVRLF ESDI                                        624

SEQ ID NO: 95          moltype = AA  length = 614
FEATURE                Location/Qualifiers
source                 1..614
                       mol_type = protein
                       organism = Penicillium sp.
SEQUENCE: 95
MRLPCVSRAL RPRPRQLTHL LNGQKCTYSA VVLGGGITGL TAAWQLAQDP ICKSITLFEK  60
TDRLGGWIDS ETVPVDGGNV VFEYGPRTLR SSLPGSLPLL YLATNLGLYK DLIVTPNTSP  120
AAQNRYIYYP DRLVRMPAPK PELSFAENFD SFVNTMMEPL FNKFLSGIVK DVFTPPRHPT  180
EWAEDESVAD FIGRRFGPKV ADNIVSAVYH GIYAGDIDQL SAQTLLGSVR NLEGGIGGIG  240
GLVSGGVTAS LISRSLSKTK TRNMEDFMAI DAISAGPELV RRQHDLEVLA AGASTFTFKR  300
GVGQLTEALV ASLKASGKVR FQMNKEITGL RALARAPAIA MEFWSDRHSQ VKTFEYDYVI  360
STIPPVALAK TMRKTEQLEA KLYPVGLTPL LLRRQDYAVT VLVVNLYYPN PNLLPVEDGF  420
GYLIPRSIPY EQNPECGLGV IFASSSVGN GTDPSSSEVN QDSAPGTKIT VMLGGHYWDG  480
FEEYPDHDTA VKMARDMLKR HMNITDTPTV TRSRLQKDAI PQYTVGHLDR MYKLSDTVRK  540
DYQKRLILAG NWYNGVSVGD CVKQGILSAT YGIGRNRLNY EPSPWRPWTS FDYKRWKLEG  600
GIVMSPVRLV DSKI                                                   614

SEQ ID NO: 96          moltype = AA  length = 566
FEATURE                Location/Qualifiers
source                 1..566
                       mol_type = protein
                       organism = Trichoderma sp.
SEQUENCE: 96
MSLKRADGAA MAFLRLSSAV CGRRRIPAGG LPADANVAVL GGGLTGLTTA YYLAKWLPPT  60
AKITLLEASD RLGGWIKTDR VPVKVGGVEG VVSFERGPRS LSSLNKSTWR FDDLVLWDLA  120
LDLGLRVVSP PDKPRYIYYP DHLVPLPPHT SLAAFASEPL VLESLWAGFG YVLRRLFSRK  180
AGVPVQDLSI ADWIQHITGS RAVAENLASA MVHGIYGGDI YTLSARSVLD RFYWVHYLPA  240
LGPDVRHMAL SEQVFMEAMG QDPLIRKLAQ QPRGALLNFG EAGMETLPIA LADALNGQAN  300
VEVKLGAKVT GLEYESETEM MKITTTGQDD SPAEKYHKVI STLPSQHLAR ITDTLPSLAS  360
SHAVSIMTVN IWYPQTNLKP PGFGYLIPLS VPAEQNPERA LGVFFDSDVG VRGPDEPAGT  420
KLFVLMGGHY YDKKQPGASV RVPSEEEAIE QAKRVLERHL GIPQSTPCFA MARLASECIP  480
QYVCGHQDTM AAADEDLRDS FDGRLAVAGG SYTKIGAMGA LRNGYDIANT VVREDWLTTG  540
LEQLEFPTQF CGVPTERIPV RRFSRR                                      566

SEQ ID NO: 97          moltype = AA  length = 606
FEATURE                Location/Qualifiers
source                 1..606
                       mol_type = protein
                       organism = Rhodotorula sp.
SEQUENCE: 97
MQSYSGNALA RQSVPIKPIR RRTPRLNLIR SLPSPRFFVT SPSSSQRHDH PYHTLAILGG  60
GLSGLSTAHY FLRTLSPSLR DQTRIVVLEK EERVGGWCRA VRIQNGRRLG ENEKPEGTED  120
LLVFETGPRS VRPVGLLGWL TIEMAHELGL TPSIVTVPKS APSARNRFIY TGHRSSTSIS  180
PILKAALPTI PSALLEPFRP RSPLHDDPSG LADESVDSFI ARRFGRRLAD ELASAGIHGI  240
YAGDTRRLSV RAVLPALWEL EKEWGSVVIG ALFGSFARRR GWKKNSPWRM RQQAETEEME  300
RVKERIRAKG GEALVEDMEK ASVWGVKGGL QVVTETLREL LEAEGVEFWM GEKGKVEHVE  360
KVDGGWQIRT SSGALDASQL VTTIPQLLPS SLAPPALPAT TVSVVNLAFE KPAPGSPPLH  420
PAGFGYLIPR TVPSSLNPHR ALGVIFDSDV MPDVDSSSSL GLTKLSLLLG GSYWLDRHPP  480
PQPSHDDLVN AALETLRLHF PDRPIPKPVH AFTHTHVNCI PQVPPGFMPS FRAFGDRLRE  540
AGNVAVVGGG FAAVGVNGCV KAAWEVGSAM AQAVNAQAGG KEGEGEEKVR EAVARTVKTG  600
TEMWEL                                                            606

SEQ ID NO: 98          moltype = AA  length = 520
FEATURE                Location/Qualifiers
source                 1..520
                       mol_type = protein
                       organism = Hesseltinella sp.
SEQUENCE: 98
MPRSIVVLGG GISGLSAAYY LSRLVPQAHI RLIESNKRAG GFIKTQQVND HLIFEAGPRT  60
LRPHGTSGTV LLDMIKDLDL SPLLVNIPKS HPSAQHRYIE YHGQINQLPS GLADMLLHSP  120
PIMDSVITAG MREPFLARAS TTKDESLYNF MERRFNEHTA LNLMGAMAHG IYAGDAKQLS  180
VHSTFPILAA CEQEYGSVVL GMLSGKLSVE SPRERQLADA CRAKDPEWFK QMQQSSVLGF  240
LPGLGALPSR LTQFLSSQPN VSMQLGETVS RLDGQSSHQI EITTSQGQIY HADHIVSTLP  300
SHALARISMP TTTSLPHLTH NPSADVALVN LAYEKCKVKP GLDGFGFLTP HADTMPPSQF  360
PGLLGMIFDS NSLGVQDQDS NMVRFTAMIG GADWNLAFGS LHDNDAISSK ALTMATAALS  420
KYLEIHESPA HYHCRILRQC IPQYLVGHRQ RMNELHAALQ HSFGHTMSVT GASYLGVSVP  480
DCIKHSRMLI EDLVDTGALG SKQAVITGLE KVTLPMYYKL                       520

SEQ ID NO: 99          moltype = AA  length = 507
FEATURE                Location/Qualifiers
```

-continued

```
source                   1..507
                         mol_type = protein
                         organism = Spizellomyces sp.
SEQUENCE: 99
MSSPSHFAVL GGGVSGLSTA WYLSKLAPKT ARITVVEKNA RVGGWVHTNM QDGQLYELGP   60
RTIRPVGVAG RAVLDMVYRL NLVEEVLTTP KNSPAAINRY IYQNSRLHHL PTSPLDLLMP  120
WKAKSPLLKG LLFSVLREPF VKPTNASDES IHGFVERRFG RALADNLVSA VIHGIYAGDS  180
TQLSVRSAMP FLWECEKKHG SVGRGVLAPP AVAPIGDERA PLSVESNDAK KFISDIQRNS  240
SIFSFKNGMQ TLTDALKRDL DKEENVSFIR GNIESLSFKE GVEIAHTASS QPLKADHVIS  300
AIPAVDLSRI LPPSSHALSS LLSSIKSVDV AVVNISFGGH FSKILPVNGF GYLVPATEDT  360
PILGTVFDSC AMPKQDSGDQ TRVTVMMGGH KFHKYFGDPD VVSKEKLLET AMTAVRTHLG  420
VNAEPIASSV VIHKQCIPQY VVGHRDRLHA IHEEVKSQHI QLSLVGASYL GVAVNDCVKG  480
ARDLVSNLLV ETQAKQRRIT GLERIET                                     507

SEQ ID NO: 100         moltype = AA  length = 514
FEATURE                Location/Qualifiers
source                 1..514
                       mol_type = protein
                       organism = Rhizophagus sp.
SEQUENCE: 100
MSSPNNFVIL GGGISGLSAA WYLSRYAPST TKILVLEGSN RFGGWIKSKR VGQHKILFEQ   60
GPRTLRPNGI GGSVVLDMVN RLNLIPSLHA VTKDDDAAKD RFIYYPDKIV KLPGTSLLSS  120
MKSVFTNNFL LKSIPSILFE PFIKPARNYH DETIHEFISR RFSKSISDIL ISALIHGIYA  180
GDINKLSIRS TFTRLYNLEQ KYGSVIKGLL MSNKEEFLSQ QDKYLLKIIN DENKDFLSIF  240
KNVSLYSFKD GIEQLSSAIV NDLKNKENVQ LKTNNQVTKL EFGENVKIFT NEAVYEADHV  300
ISALPSRALY NILPEKDVLP HLNYNPSVSV ATINLAYAHP KILPVKGFGY LIPQSTPHNP  360
YHVLGVVFDS NAMPLQDEPS RTYTKLTIMM GGHYFNSISE KDDFPKKEIL LQQSIEILEK  420
HLGIYSTPLY YLVDIQKNCI PQYYVGHYSR LKELHYAIKN HYANRLSVTG ASYWGISIND  480
CVLNSAKLVL NILSNSPNVV TGLEEVEIQN EHYL                             514

SEQ ID NO: 101         moltype = AA  length = 477
FEATURE                Location/Qualifiers
source                 1..477
                       mol_type = protein
                       organism = Homo sapiens
SEQUENCE: 101
MGRTVVVLGG GISGLAASYH LSRAPCPPKV VLVESSERLG GWIRSVRGPN GAIFELGPQG   60
IRPAGALGAR TLLLVSELGL DSEVLPVRGD HPAAQNRFLY VGGALHALPT GLRGLLRPSP  120
PFSKPLFWAG LRELTKPRGK EPDETVHSFA QRRLGPEVAS LAMDSLCRGV FAGNSRELSI  180
RSCFPSLFQA EQTHRSILLG LLLGAGRTPQ PDSALIRQAL AERWSQWSLR GGLEMLPQAL  240
ETHLTSRGVS VLRGQPVCGL SLQAEGRWKV SLRDSSLEAD HVISAIPASV LSELLPAEAA  300
PLARALSAIT AVSVAVVNLQ YQGAHLPVQG FGHLVPSSED PGVLGIVYDS VAFPEQDGSP  360
PGLRVTVMLG GSWLQTLEAS GCVLSQELFQ QRAQEAAATQ LGLKEMPSHC LVHLHKNCIP  420
QYTLGHWQKL ESARQFLTAH RLPLTLAGAS YEGVAVNDCI ESGRQAAVSV LGTEPNS     477

SEQ ID NO: 102         moltype = AA  length = 543
FEATURE                Location/Qualifiers
source                 1..543
                       mol_type = protein
                       organism = Glycine max
SEQUENCE: 102
MVSVFNEILF PPNQTLLRPS LHSPTSFFTS PTRKFPRSRP NPILRCSIAE ESTASPPKTR   60
DSAPVDCVVV GGGVSGLCIA QALATKHANA NVVVTEARDR VGGNITTMER DGYLWEEGPN  120
SFQPSDPMLT MVVDSGLKDE LVLGDPDAPR FVLWNRKLRP VPGKLTDLPF FDLMSIGGKI  180
RAGFGALGIR PPPPGHEESV EEFVRRNLGD EVFERLIEPF CSGVYAGDPS KLSMKAAFGK  240
VWKLEKNGGS IIGGTFKAIQ ERNGASKPPR DPRLPKPKGQ TVGSFRKGLT MLPDAISARL  300
GNKVKLSWKL SSISKLDSGE YSLTYETPEG VVSLQCKTVV LTIPSYVAST LLRPLSAAAA  360
DALSKFYYPP VAAVSISYPK EAIRSECLID GELKGFGQLH PRSQGVETLG TIYSSSLFPN  420
RAPPGRVLLL NYIGGATNTG ILSKTDSELV ETVDRDLRKI LINPNAQDPF VVGVRLWPQA  480
IPQFLVGHLD LLDVAKASIR NTGFEGLFLG GNYVSGVALG RCVEGAYEVA AEVNDFLTNR  540
VYK                                                              543

SEQ ID NO: 103         moltype = AA  length = 504
FEATURE                Location/Qualifiers
source                 1..504
                       mol_type = protein
                       organism = Nicotiana tabacum
SEQUENCE: 103
MAPSAGEDKH SSAKRVAVIG AGVSGLAAAY KLKIHGLNVT VFEAEGKAGG KLRSVSQDGL   60
IWDEGANTMT ESEGDVTFLI DSLGLREKQQ FPLSQNKRYI ARNGTPVLLP SNPIDLIKSN  120
FLSTGSKLQM LLEPILWKNK KLSQVSDSHE SVSGFFQRHF GKEVVDYLID PFVAGTCGGD  180
PDSLSMHHSF PELWNLEKRF GSVILGAIRS KLSPKNEKKQ GPPKTSANKK RQRGSFSFLG  240
GMQTLTDAIC KDLREDELRL NSRVLELSCS CTEDSAIDSW SIISASPHKR QSEEESFDAV  300
IMTAPLCDVK SMKIAKRGNP FLLNFIPEVD YVPLSVVITT FKRENVKYPL EGFGVLVPSK  360
EQQHGLKTLG TLFSSMMFPD RAPNNVYLYT TFVGGSRNRE LAKASRTELK EIVTSDLKQL  420
LGAEGEPTYV NHLYWSKAFP LYGHNYDSVL DAIDKMEKNL PGLFYAGNHR GGLSVGKALS  480
SGCNAADLVI SYLESVSTDS KRHC                                        504

SEQ ID NO: 104         moltype = AA  length = 635
```

```
FEATURE            Location/Qualifiers
source             1..635
                   mol_type = protein
                   organism = Trichoderma sp.
SEQUENCE: 104
MELSLLRPTT QSLLPSFSKP NLRLNVYKPL RLRCSVAGGM RLPCASSRVF RQVRAPLALL  60
RRGQRHALHT KQFDAAVIGG GITGLTAAYQ LSRDPSCSKV TLYEKSSHLG GWLSSEQIPV  120
RGGHVVFEYG PRTLRTSAPS CLPMMDLIMN LDLLDDVLIC DKKSPAAQNR YIYYPDHLVR  180
LPFPPTEGLL KTAWTLLMEP LFETFLQSAL FEKPKRAVDG DVLSRDESVA DFVSRRFSPK  240
MSENLASAVM AGIFAGDVNR LSADMAIGYV RELEKRYGSI VDGMMTQRAS ELRAMPMDEF  300
LALESVAVPS HKDDRYWKSL RAVVSDASVL TLKNGLGQLT DAMAAQLRSS NNVEVVSGTE  360
VTSLSQNPET RDLTIGFGKN ESKTHNRVIA THAPSSLARQ LENTKVGVAP SDTLRALGQN  420
NYAVTVMVVN LYYEDPDLVP VQGFGYLLPS SIPFEENPER ALGVIFGSQS SEGQDTAPGT  480
KLTVMMGGHL WDGWSESDYP DPDKAVEMAQ ALLHRHLGIK TAPSVARARL LRDAIPQYTV  540
GHLSRMKELS QSVRGDFHKR LTLAGAWYGT VGIGVVDCIR QGYIASSFGV GSKKLGPGGG  600
RRPWTKHDFH NWELEGGICT SPVRFDNVHI TERQH                            635

SEQ ID NO: 105     moltype = AA  length = 636
FEATURE            Location/Qualifiers
source             1..636
                   mol_type = protein
                   organism = Aspergillus sp.
SEQUENCE: 105
MELSLLRPTT QSLLPSFSKP NLRLNVYKPL RLRCSVAGGM RLPCVPSCAL RGVRTPLAFA  60
RIGQRYSSTY DAAVIGGGIT GLTAAYRLSQ DPNCSKITLY EKAPRVGGWL LSEKIPVEGG  120
NVVFEYGPRT LRTAVPSCLP LLDLLLVELG LHDDVLLTSSS SPAARNRYIY YPDHLVRMPA  180
PDPNAGPIEN ITNPLFAMLR EPVFEGLIAS ALLEPVRAPP DHKTFNSDES VADFVSRRLC  240
PEVADNLVSA LFHGIYAGDI SRLSAQTLLG TFRDLENDDR RVIGGYINSL MSDVKLMAMD  300
DLLALESVAH EKPGMYWKSL RTLVNKTSVL TLKDGLSQLS DALVDALKKS KKVDVLANTD  360
VKSITQNPMT DDLIVGSGQD RSRIHNRVIA TIPAPELANK LATTTVKDQK VPQSTIRNLQ  420
EHNYAVTVMV VNLYFPNPDL LPVSGFGYLI PRSIPYEQNP ERALGVIFGS DSSVGQDTAP  480
GTKLTVMMGG HWWDGWKESD YPDHDTAVAM SRALLHRHLG ITDAPTLTSS RLQRNAIPQY  540
TVGHLSRMRE LSRSTRHELN NRLTLAGSWY NGVGVTDCIR QGYLAASFGV GARKLGPGDG  600
DRPWRRFDYE KWELEGGIVT SPVRWAEVYR TERKHF                           636

SEQ ID NO: 106     moltype = AA  length = 635
FEATURE            Location/Qualifiers
source             1..635
                   mol_type = protein
                   organism = Aspergillus sp.
SEQUENCE: 106
MELSLLRPTT QSLLPSFSKP NLRLNVYKPL RLRCSVAGGM RLPHASSHAL KGSRLSLALA  60
RNGQRRSLHT PTYDAAVVGG GITGLTTAYR LSRDPKCSKI TLYEKSKNVG GWLQSEKIPF  120
KDGHVVFEYG PRTLRTALPS CLPLLDLLEE LDLLGEVLVT SKTSAAALNR YIYYPDHLAR  180
VPAPDPARGA LGNALSLMWS LFREPVFKSI FLGIYNDIQS PAPQKLKADE SVGDFISRRL  240
SPELADNLVS SVFHGIYAGD IYQLSAEALL GQHREPEGGV PSIMLRLINE ARMNHTPELL  300
DDQLAMELIL EEKSRSYLNA LAVLVRQASV LTLRNGLGQL TDALLAALAK SKKVDILPEA  360
EVTAISRNQN SSNITISHGQ DEHRMHNRVV STIPAPHLAK ALRQGGGEDK KLPHNTIQAL  420
EEHNYAVTVM VVNLFYEKED LLPVKGFGYL IPRSIPFEQN PERGLGVIFG SETSAGQDTV  480
PGTKLTVMLG GHLWDGWTES DYPDHDTAVK MARTLLERHL GITDAPAISR SRLHRNAIPQ  540
YTVGHPARMD RISESARADF SNRLSLAGSW YGGIGVVDCI RHAYLTAAYG VSAQKLRSGG  600
QDRPWKLFNY TQWELEGGIV KSPVRLVWRR PDSKN                            635

SEQ ID NO: 107     moltype = AA  length = 640
FEATURE            Location/Qualifiers
source             1..640
                   mol_type = protein
                   organism = Fusarium sp.
SEQUENCE: 107
MELSLLRPTT QSLLPSFSKP NLRLNVYKPL RLRCSVAGGM SHSRAESTAV ALLSSAAHST  60
TKPHLRVPLC RLNGFRNLST CSASALTRRR PIIACKHTQS SRDGRRYVSQ AKDANIAVIG  120
GGLTGLSAAY YLAKKLPSTT KITLYEANDR LGGWIKTDRV PVDIEGKKGI VSFERGSRSL  180
TSLVGNTFRF DDLVLYDLTL DLGLSLNFPP ARPRYVYYPD HLVATPPNIS IFDILREPLY  240
LESFGAGLGL MINQLRKRQL PAEDESVADW LYKVTNSRKG IGNLASAMMH GIYGGDINKL  300
SARSVLDRIY WGWYMPNPGL HARPMPLPEQ LILELTGQDR QIQKLALEPK STLIDFGDKG  360
MESLPQAIGA ALRDQPNVTI MTGEAVNDIQ YDEAKKQVQI NSFNTQNEEK SNSQAYDKIV  420
STLSAQHIAR LAGDKVQSLS AAHSVSVMTV NIWFPQENLK PPGFGYLIPD SVEPELNPEH  480
ALGVFFDSDV GTRSKDEPAG TKLFVLMGGH YYDRPGVTPP TEDEAIVQAR NLLERHLGIP  540
RDAPAYATAN FAKECIPQHN VGHQDLLRNA HAELKQNFGG RLAVAGGSFH RIGTIASLRS  600
GYDAAVATKN GLEATGLEYL ETITEFAVVP TDMIPVRLFK                       640

SEQ ID NO: 108     moltype = AA  length = 634
FEATURE            Location/Qualifiers
source             1..634
                   mol_type = protein
                   organism = Fusarium sp.
SEQUENCE: 108
MELSLLRPTT QSLLPSFSKP NLRLNVYKPL RLRCSVAGGM SRRRAESTAV ALLGSPAKPH  60
LPLPLRRLDA IRSLSTSSAL TRRRPIVARN YTQFFNNGRT FVSQAKDANI AVLGGGLTGL  120
```

```
TAAYYLAKKL PSTAKITLYE SSDRLGGWIK TDRVPVDVEG KSGTVSFERG ARSLSSLAGN   180
TFRFDDLVLY DLALDLGLVV NSPRQQPRYI YYPDHLVPMP PNVSIFDIFR EPLYLESIGA   240
SLGLGINSLR KRTLPSKDYS VSEWLYAVSN SRKGVGTLAS AMMHGIYGGD IDKLSARSVL   300
DRVYWGWYLP NPGLSARPMP VAEQTLLETL GQDKQIQKMA LEPRSALVDF GDKGMESLPQ   360
ALSTALREQP NVTIKTGEAV QDVVHNKTNQ QVHVTSSNAK NKSEHNSKVY DKVISTLSAQ   420
DIARLTGDKL PSLSTAHSVS VMTVNIWFPR ENLKPPGFGY LIPNSVAPEL NPEHALGVFF   480
DSDVQTRSKD EPAGTKLFVL MGGHYYDRPD VTPPTEEEAI LQARNLLERH LGIPRDAPAY   540
ATANFARECI PQHYVGHQDR LRAAHTELTH NFGGRLAVAG GSFTRIGAIA SLRAGYDAAT   600
AAKEGLEATG LEYLNDIQQF SVVATSHIPV RHFK                              634

SEQ ID NO: 109          moltype = AA  length = 599
FEATURE                 Location/Qualifiers
source                  1..599
                        mol_type = protein
                        organism = Rhizopus sp.

SEQUENCE: 109
MELSLLRPTT QSLLPSFSKP NLRLNVYKPL RLRCSVAGGM SSVAILGGGI SGLSAAYYLA   60
RMAPPTTKIT LIEGKKRLGG WIESRRVTPG HYDNIHQLPK NNSKENTILF EAGPRTLRPE   120
GSNGAILLEM IRHLELNNEN LMSVSKSHPS ARHRYIYYKD KINTLPSDLQ SFLLNKPPVL   180
KSVPLAALLE PLKPSRFDKD GIAKDGIEDE SIYSFMTRRF NEHTAIHLMG AVIHGIYAGD   240
IKSLSLQSTL RSLYEAERIY GSAVLGMMKG ASQVTTSVRE RGMAARSRKE DPEWFGRMEK   300
MSVIGFKSGM DTLPHQITSW LEQCPNVEVI TDDPAEHIEI AHENKIKTQK GKTVHADHII   360
STLPSPVLER LVQHQPVLPH LSYNPSADVA VVNLAYSPDE MKLQYDGFGF LTPHRDTPYG   420
NPLPGTLGVV FDSNALPIES ERAVKLTAMI GGSDWKDAFG NVPIDELEPK VALDYTRKAV   480
GTFLDIHAEP RYSMVNLQKQ CIPQYLVGHQ DRMLSLHHAI KKNYGHALSV SGASYLGVSV   540
PDCIKNSRML VEELLVSGAL GSRQKVVTGL GKLEEQPTVD EMRDNARLSR GNTSVIMKS    599

SEQ ID NO: 110          moltype = AA  length = 598
FEATURE                 Location/Qualifiers
source                  1..598
                        mol_type = protein
                        organism = Rhizopus sp.

SEQUENCE: 110
MELSLLRPTT QSLLPSFSKP NLRLNVYKPL RLRCSVAGGM SSIAVLGGGI SGLSAAYYLA   60
RLAPASTKIV LIEGKDRLGG WIHSRRVAPG KYSRDKAPQL SNEKDSILFE AGPRSLRPEG   120
PNGAILLEMI QNLDLNNEGL LSVPKTDPSV KNRYIYYDGE INTLPSGPIS MLLKKPPVFK   180
SVILAGALEP LRSSRFKNGK PKDGIEDESM YNFMKRRFNE HTAINLMGAV AHGVYAGDVK   240
QLSIQSTLRM LYEAEKNYGS VIVGMMRGAA NTSTMRERGM AVRSRDKDPE WFGRMEKMSV   300
LGFKDGMETL PDRLCSWLEQ RPNVEIIRND PVESIEPLEN GKESKIKTKS NEFFADHVLS   360
TIPSFTLEKL IKPNSLPNLS HNPASDVAVV NFAYSPEVKL GYDGFGFLTP HRDTKYRVPV   420
PGTLGVIFDS NAMPGQETEQ PEVVKVTAMM GGADWKDAFG KATIDELDPE VAYKYARKGM   480
SVFLNLHDEP THAMVNLQKQ CIPQYVVGHE GRMRELHHAL KQNYGHLMSL TGASYMGVSV   540
PDCIKNSRML VEELLVSGAL GSRDKVVTGL GRTVESNSKE LQDGARISKG TVDVIMKS     598

SEQ ID NO: 111          moltype = AA  length = 589
FEATURE                 Location/Qualifiers
source                  1..589
                        mol_type = protein
                        organism = Rhizopus sp.

SEQUENCE: 111
MELSLLRPTT QSLLPSFSKP NLRLNVYKPL RLRCSVAGGM SAVILGGGIS GLSAAYYLAR   60
MAPSTTKITL IEGKNRLGGW IESRRVTAGH YDNIHCLPKE NQQNTVLFEA GPRTLRPEGT   120
NGAILLEMIR HLDLNNDDLL SIPKSHPSAK NRYIYYQDKI NKLPSDFGSF LRQRPPVLKS   180
VPLAGLLEPL RTSRFENGLP KNGEEDESIY SFISRRFNEH TATHLMGAVI HGIYAGDVRA   240
LSLQSTLNSL YEAERTYGSA VLGMLKGVSQ ATQTMRERGM AARSRKDDPD WFGRMEKMSV   300
IGFKTGMDSL PDKITAWLKQ RPNVEIITHD SVQHIGEGKI KTEHREIEAD HIISTLPSSV   360
LHSLLSRPLP HLMHNPAVDV AVVNLAYPSD IKLDYDGFGF LTPHRDSKYP NPVPGTLGVV   420
FDSNSLPIDS EHATKLTVMM GGSDWKDAFG DVSLDQLDPQ VALQRARQAV STFLGIHAEP   480
HASMVHLQKQ CIPQYLVGHR QRMRSLHHAI KQDYGHSLSV SGASYLGVSV PDCIKNSRML   540
VEELLVSGAL GSRQKIVTGL GRLEQEMTVE EMRDNARVSK SNTSVIIKS               589

SEQ ID NO: 112          moltype = AA  length = 663
FEATURE                 Location/Qualifiers
source                  1..663
                        mol_type = protein
                        organism = Penicillium sp.

SEQUENCE: 112
MELSLLRPTT QSLLPSFSKP NLRLNVYKPL RLRCSVAGGM RLLTASKGLR SPQKPLISAI   60
RCQHRSYNAA VIGGGITGLT AAWQLIQDRE CSSVTIYEKS RRLGGWLQSE TIPVEGGEVV   120
FEYGPRTLRS AMPASLPLLY LVSNLGLFDE LITTSKRSPA ALNRYIYYPD HLVRLPTPDP   180
DLSLMENARN IFRTITTEPL FEGFITGLLS EPNKPARPQE EWAIDESLAE FITRRFNRKI   240
ADNLVSAVMH GIYADNIDEM SAQAIMGPLR NLEDGGILFG LLIKSIMGKK TRSMDDFLAV   300
DAVYKTPETM QRLDEINRVV KTASTFTFKR GTQQLVEGLT RALRASEKVR LVMDADILAL   360
DPPANRGHKL KIYTGIRGEE SFDHVISAIS APAMARILDP QGQVKIDCDP EDEYRALWNS   420
KKARHPKPNI GTVSGLHFFR HATTVMVVNL YYKTPNLLPV DGFGYLIPRS IPYEQNPECG   480
LGVIFASASS SGESPVAPYP KVSQDSAPGT KITIMFGGHY WDGWKKQDYP DHKTAVRMAK   540
DMLERHLGIT EPPALVRTRL QENAIPKYKP PHIHQIYALS RWAKEEYHNR LVLVGNSFSG   600
VGVGDCVRQG IMAATHGVGR HKLTATPRLE SKDWCPWKEY NYQHWDLKGG VPTAPVRLFE   660
SDI                                                               663
```

```
SEQ ID NO: 113            moltype = AA  length = 653
FEATURE                   Location/Qualifiers
source                    1..653
                          mol_type = protein
                          organism = Penicillium sp.
SEQUENCE: 113
MELSLLRPTT QSLLPSFSKP NLRLNVYKPL RLRCSVAGGM RLPCVSRALR PRPRQLTHLL   60
NGQKCTYSAV VLGGGITGLT AAWQLAQDPI CKSITLFEKT DRLGGWIDSE TVPVDGGNVV  120
FEYGPRTLRS SLPGSLPLLY LATNLGLYKD LIVTPNTSPA AQNRYIYYPD RLVRMPAPKP  180
ELSFAENFDS FVNTMMEPLF NKFLSGIVKD VFTPPRHPTE WAEDESVADF IGRRFGPKVA  240
DNIVSAVYHG IYAGDIDQLS AQTLLGSVRN LEGGIGGIGG LVSGGVTASL ISRSLSKTKT  300
RNMEDFMAID AISAGPELVR RQHDLEVLAA GASTFTFKRG VGQLTEALVA SLKASGKVRF  360
QMNKEITGLR ALARAPAIAM EFWSDRHSQV KTFEYDYVIS TIPPVALAKT MRKTEQLEAK  420
LYPVGLTPLL LRRQDYAVTV LVVNLYYPNP NLLPVEDGFG YLIPRSIPYE QNPECGLGVI  480
FASSSSVGNG TDPSSSEVNQ DSAPGTKITV MLGGHYWDGF EEYPDHDTAV KMARDMLKRH  540
MNITDTPTVT RSRLQKDAIP QYTVGHLDRM YKLSDTVRKD YQKRLILAGN WYNGVSVGDC  600
VKQGILSATY GIGRNRLNYE PSPWRPWTSF DYKRWKLEGG IVMSPVRLVD SKI         653

SEQ ID NO: 114            moltype = AA  length = 605
FEATURE                   Location/Qualifiers
source                    1..605
                          mol_type = protein
                          organism = Trichoderma sp.
SEQUENCE: 114
MELSLLRPTT QSLLPSFSKP NLRLNVYKPL RLRCSVAGGM SLKRADGAAM AFLRLSSAVC   60
GRRRIPAGGL PADANVAVLG GGLTGLTTAY YLAKWLPPTA KITLLEASDR LGGWIKTDRV  120
PVKVGGVEGV VSFERGPRSL SSLNKSTWRF DDLVLWDLAL DLGLRVVSPP DKPRYIYYPD  180
HLVPLPPPHTS LAAFASEPLV LESLWAGFGY VLRRLFSRKA GVPVQDLSIA DWIQHITGSR  240
AVAENLASAM VHGIYGGDIY TLSARSVLDR FYWVHYLPAL GPDVRHMALS EQVFMEAMGQ  300
DPLIRKLAQQ PRGALLNFGE AGMETLPIAL ADALNGQANV EVKLGAKVTG LEYESETEMM  360
KITTTGQDDS PAEKYHKVIS TLPSQHLARI TDTLPSLASS HAVSIMTVNI WYPQTNLKPP  420
GFGYLIPLSV PAEQNPERAL GVFFDSDVGV RGPDEPAGTK LFVLMGGHYY DKKQPGASVR  480
VPSEEEAIEQ AKRVLERHLG IPQSTPCFAM ARLASECIPQ YVCGHQDTMA AADEDLRDSF  540
DGRLAVAGGS YTKIGAMGAL RNGYDIANTV VREDWLTTGL EQLEFPTQFC GVPTERIPVR  600
RFSRR                                                             605

SEQ ID NO: 115            moltype = AA  length = 645
FEATURE                   Location/Qualifiers
source                    1..645
                          mol_type = protein
                          organism = Rhodotorula sp.
SEQUENCE: 115
MELSLLRPTT QSLLPSFSKP NLRLNVYKPL RLRCSVAGGM QSYSGNALAR QSVPIKPIRR   60
RTPRLNLIRS LPSPRFFVTS PSSSQRHDHP YHTLAILGGG LSGLSTAHYF LRTLSPSLRD  120
QTRIVVLEKE ERVGGWCRAV RIQNGRRLGE NEKPEGTEDL LVFETGPRSV RPVGLLGWLT  180
IEMAHELGLT PSIVTVPKSA PSARNRFIYT GHRSSTSISP ILKAALPTIP SALLEPFRPR  240
SPLHDDPSGL ADESVDSFIA RRFGRRLADE LASAGIHGIY AGDTRRLSVR AVLPALWELE  300
KEWGSVVIGA LFGSFARRRG WKKNSPWRMR QQAETEEMER VKERIRAKGG EALVEDMEKA  360
SVWGVKGGLQ VVTETLREKL EAEGVEFWMG EKGKVEHVEK VDGGWQIRTS SGALDASQLV  420
TTIPQLLPSS LAPPALPATT VSVVNLAFEK PAPGSPPLHP AGFGYLIPRT VPSSLNPHRA  480
LGVIFDSDVM PDVDSSSSLG LTKLSLLLGG SYWLDRHPPP QPSHDDLVNA ALETLRLHFP  540
DRPIPKPVHA FTHTHVNCIP QVPPGFMPSF RAFGDRLREA GNVAVVGGGF AAVGVNGCVK  600
AAWEVGSAMA QAVNAQAGGK EGEGEEKVRE AVARTVKTGT EMWEL                 645

SEQ ID NO: 116            moltype = AA  length = 559
FEATURE                   Location/Qualifiers
source                    1..559
                          mol_type = protein
                          organism = Hesseltinella sp.
SEQUENCE: 116
MELSLLRPTT QSLLPSFSKP NLRLNVYKPL RLRCSVAGGM PRSIVVLGGG ISGLSAAYYL   60
SRLVPQAHIR LIESNKRAGG FIKTQQVNDH LIFEAGPRTL RPHGTSGTVL LDMIKDLDLS  120
PLLVNIPKSH PSAQHRYIEY HGQINQLPSG LADMLLHSPP IMDSVITAGM REPFLARAST  180
TKDESLYNFM ERRFNEHTAL NLMGAMAHGI YAGDAKQLSV HSTFPILAAC EQEYGSVVLG  240
MLSGKLSVES PRERQLADAC RAKDPEWFKQ MQQSSVLGFL PGLGALPSRL TQFLSSQPNV  300
SMQLGETVSR LDGQSSHQIE ITTSQGQIYH ADHIVSTLPS HALARISMPT TTSLPHLTHN  360
PSADVALVNL AYEKCKVKPG LDGFGFLTPH ADTMPPSGHP GLLGMIFDSN SLGVQDQDSN  420
MVRFTAMIGG ADWNLAFGSL HDNDAISSKA LTMATAALSK YLEIHESPAH YHCRILRQCI  480
PQYLVGHRQR MNELHAALQH SFGHTMSVTG ASYLGVSVPD CIKHSRMLIE DLVDTGALGS  540
KQAVITGLEK VTLPMYYKL                                              559

SEQ ID NO: 117            moltype = AA  length = 546
FEATURE                   Location/Qualifiers
source                    1..546
                          mol_type = protein
                          organism = Spizellomyces sp.
SEQUENCE: 117
MELSLLRPTT QSLLPSFSKP NLRLNVYKPL RLRCSVAGGM SSPSHFAVLG GGVSGLSTAW   60
```

```
YLSKLAPKTA RITVVEKNAR VGGWVHTNMQ DGQLYELGPR TIRPVGVAGR AVLDMVYRLN   120
LVEEVLTTPK NSPAAINRYI YQNSRLHHLP TSPLDLLMPW KAKSPLLKGL LFSVLREPFV   180
KPTNASDESI HGFVERRFGR ALADNLVSAV IHGIYAGDST QLSVRSAMPF LWECEKKHGS   240
VGRGVLAPPA VAPIGDERAP LSVESNDAKK FISDIQRNSS IFSFKNGMQT LTDALKRDLD   300
KEENVSFIRG NIESLSFKEG VEIAHTASSQ PLKADHVISA IPAVDLSRIL PPSSHALSSL   360
LSSIKSVDVA VVNISFGGHF SKILPVNGFG YLVPATEDTP ILGTVFDSCA MPKQDSGDQT   420
RVTVMMGGHK FHKYFGDPDV VSKEKLLETA MTAVRTHLGV NAEPIASSVV IHKQCIPQYV   480
VGHRDRLHAI HEEVKSQHIQ LSLVGASYLG VAVNDCVKGA RDLVSNLLVE TQAKQRRITG   540
LERIET                                                             546

SEQ ID NO: 118            moltype = AA   length = 553
FEATURE                   Location/Qualifiers
source                    1..553
                          mol_type = protein
                          organism = Rhizophagus sp.
SEQUENCE: 118
MELSLLRPTT QSLLPSFSKP NLRLNVYKPL RLRCSVAGGM SSPNNFVILG GGISGLSAAW   60
YLSRYAPSTT KILVLEGSNR FGGWIKSKRV GQHKILFEQG PRTLRPNGIG GSVVLDMVNR   120
LNLIPSLHAV TKDDDAAKDR FIYYPDKIVK LPGTSLLSSM KSVFTNNFLL KSIPSILFEP   180
FIKPARNYHD ETIHEFISRR FSKSISDILI SALIHGIYAG DINKLSIRST FTRLYNLEQK   240
YGSVIKGLLM SNKEEFLSQQ DKYLLKIIND ENKDFLSIFK NVSLYSFKDG IEQLSSAIVN   300
DLKNKENVQL KTNNQVTKLE FGENVKIFTN EAVYEADHVI SALPSRALYN ILPEKDVLPH   360
LNYNPSVSVA TINLAYAHPK ILPVKGFGYL IPQSTPHNPY HVLGVVFDSN AMPLQDEPSR   420
TYTKLTIMMG GHYFNSISEK DDFPKKEILL QQSIEILEKH LGIYSTPLYY LVDIQKNCIP   480
QYYVGHYSRL KELHYAIKNH YANRLSVTGA SYWGISINDC VLNSAKLVLN ILSNSPNVVT   540
GLEEVEIQNE HYL                                                     553

SEQ ID NO: 119            moltype = AA   length = 508
FEATURE                   Location/Qualifiers
source                    1..508
                          mol_type = protein
                          organism = Arabidopsis thaliana
SEQUENCE: 119
MASGAVADHQ IEAVSGKRVA VVGAGVSGLA AAYKLKSRGL NVTVFEADGR VGGKLRSVMQ   60
NGLIWDEGAN TMTEAEPEVG SLLDDLGLRE KQQFPISQKK RYIVRNGVPV MLPTNPIELV   120
TSSVLSTQSK FQILLEPFLW KKKSSSKVSDA SAEESVSEFF QRHFGQEVVD YLIDPFVGGT   180
SAADPDSLSM KHSFPDLWNV EKSFGSIIVG AIRTKFAAKG GKSRDTKSSP GTKKGSRGSF   240
SFKGGMQILP DTLCKSLSHD EINLDSKVLS LSYNSGSRQE NWSLSCVSHN ETQRQNPHYD   300
AVIMTAPLCN VKEMKVMKGG QPFQLNFLPE INYMPLSVLI TTFTKEKVKR PLEGFGVLIP   360
SKEQKHGFKT LGTLFSSMMF PDRSPSDVHL YTTFIGGSRN QELAKASTDE LKQVVTSDLQ   420
RLLGVEGEPV SVNHYYWRKA FPLYDSSYDS VMEAIDKMEN DLPGFFYAGN HRGGLSVGKS   480
IASGCKAADL VISYLESCSN DKKPNDSL                                     508

SEQ ID NO: 120            moltype = AA   length = 548
FEATURE                   Location/Qualifiers
source                    1..548
                          mol_type = protein
                          organism = Nicotiana tabacum
SEQUENCE: 120
MTTTPIANHP NIFTHQSSSS PLAFLNRTSF IPFSSISKRN SVNCNGWRTR CSVAKDYTVP   60
SSAVDGGPAA ELDCVIVGAG ISGLCIAQVM SANYPNLMVT EARDRAGGNI TTVERDGYLW   120
EEGPNSFQPS DPMLTMAVDC GLKDDLVLGD PNAPRFVLWK GKLRPVPSKL TDLPFFDLMS   180
IPGKLRAGFG AIGLRPSPPG HEESVEQFVR RNLGGEVFER LIEPFCSGVY AGDPSKLSMK   240
AAFGKVWKLE ETGGSIIGGT FKAIKERSST PKAPRDPRLP KPKGQTVGSF RKGLRMLPDA   300
ISARLGSKLK LSWKLSSITK SEKGGYHLTY ETPEGVVSLQ SRSIVMTVPS YVASNILRPL   360
SVAAADALSN FYYPPVGAVT ISYPQEAIRD ERLVDGELKG FGQLHPRTQG VETLGTIYSS   420
SLFPNRAPKG RVLLLNYIGG AKNPEILSKT ESQLVEVVDR DLRKMLIKPK AQDPLVVGVR   480
VWPQAIPQFL VGHLDTLSTA KAAMNDNGLE GLFLGGNYVS GVALGRCVEG AYEVASEVTG   540
FLSRYAYK                                                           548

SEQ ID NO: 121            moltype = AA   length = 537
FEATURE                   Location/Qualifiers
source                    1..537
                          mol_type = protein
                          organism = Arabidopsis thaliana
SEQUENCE: 121
MELSLLRPTT QSLLPSFSKP NLRLNVYKPL RLRCSVAGGP TVGSSKIEGG GGTTITTDCV   60
IVGGGISGLC IAQALATKHP DAAPNLIVTE AKDRVGGNII TREENGFLWE EGPNSFQPSD   120
PMLTMVVDSG LKDDLVLGDP TAPRFVLWNG KLRPVPSKLT DLPFFDLMSI GGKIRAGFGA   180
LGIRPSPPGR EESVEEFVRR NLGDEVFERL IEPFCSGVYA GDPSKLSMKA AFGKVWKLEQ   240
NGGSIIGGTF KAIQERKNAP KAERDPRLPK PQGQTVGSFR KGLRMLPEAI SARLGSKVKL   300
SWKLSGITKL ESGGYNLTYE TPDGLVSVQS KSVVMTVPSH VASGLLRPLS ESAANALSKL   360
YYPVAAVSI SYPKEAIRTE CLIDGELKGF GQLHPRTQGV ETLGTIYSSS LFPNRAPPGR   420
ILLLNYIGGS TNTGILSKSE GELVEAVDRD LRKMLIKPNS TDPLKLGVRV WPQAIPQFLV   480
GHFDILDTAK SSLTSSGYEG LFLGGNYVAG VALGRCVEGA YETAIEVNNF MSRYAYK     537
```

PROTOPORPHYRINOGEN OXIDASE (PPO) RESISTANCE PLANT

CROSS REFERENCE TO RELATED APPLICATIONS

This application is a Bypass Continuation of PCT Patent Application No. PCT/IL2023/050776 having International filing date of Jul. 26, 2023, which claims the benefit of priority of U.S. Provisional Patent Application Nos. 63/393,933, filed Jul. 31, 2022, and 63/423,001, filed Nov. 6, 2022, the contents of which are all incorporated herein by reference in their entirety.

REFERENCE TO AN ELECTRONIC SEQUENCE LISTING

The contents of the electronic sequence listing (PAB_008-PCT SL.xml; Size: 134,957 bytes; and Date of Creation: Jul. 26, 2023) is herein incorporated by reference in its entirety.

FIELD OF INVENTION

The present invention relates to transgenic plants and methods for conferring Herbicide Tolerance (HT) to proto-porphyrinogen oxidase (PPO)-type inhibitor herbicides, and controlling weeds.

BACKGROUND

Weeds have been a major cause of crop yield losses since the origin of agriculture.

Worldwide, weeds compete with crops for space, nutrients, water, and light, causing damage that is estimated to sum up to a loss of about one-third of the potential yield of the crop.

Weeds also compete with pasture, degrading productive land into unusable scrub.

Moreover, weeds can be poisonous, distasteful, produce burrs, thorns, or otherwise interfere with the use and management of desirable plants by contaminating harvests or interfering with livestock.

Herbicides are the most commonly used and effective means for weed control. However, herbicide resistance is constantly growing with hundreds of weed biotypes currently identified as being resistant to one or more herbicides.

Protoporphyrinogen Oxidase inhibitors (PPO-inhibitors) are a class of herbicides that target the enzyme Protopor-phyrinogen Oxidase (PPO) which is active in chloroplast and mitochondria and participates in the catalysis of the organic compound Protoporphyrin IX—a precursor of heme and chlorophyll. The inhibition interferes with the biosynthesis of heme (WSSA Group: 14; HRAC GROUP: E), and ultimately leads to the accumulation of peroxidative agents that cause the breakdown of cell membranes. For this reason, PPO inhibitors hinder plants' growth and are also called cell membrane disruptors.

Herbicides that act by inhibiting PPO, are well known, and include the following herbicide families, Phenylpyra-zoles, Pyrimidindiones, Oxazolidinedione, Diphenylethers, Oxadiazoles, N-phenylphthalimides, Triazinone, Thiadiaz-oles, Triazolinones, and Triazolopyridinones and their commercial names are, for example, Star, Goal, Strike and Aurora. Such herbicides include the active compounds flu-mioxazin, fomesafen, fluthiacet, carfentrazone, sulfentra-zone, acifluorfen, lactofen, flumiclorac, saflufenacil or others.

PPO-inhibitors can be used during the growth of a crop, only if the crop is resistant/tolerant to the herbicide. The treatment of plants susceptible to PPO inhibition, such as, but not limited to, broad-leaf plants, is thus limited. It has been particularly difficult to achieve a resistance that provides commercial levels of tolerance to at least some desirable PPO-type inhibitor herbicides. Accordingly, new methods for conferring PPO-herbicide tolerance upon various crops and crop varieties are needed.

SUMMARY OF THE INVENTION

The present invention discloses transgenic plants and methods for conferring Herbicide Tolerance (HT) to proto-porphyrinogen oxidase (PPO)-type inhibitor herbicides and controlling weeds by selectively protecting transgenic crop expressing a fungal-derived PPO enzyme.

Advantageously, disclosed are transgenic plants, cells, and seeds that have been genetically modified with exogenous fungal-derived PPO enzyme, variants, mutants, motifs, fragments, and/or protein fusions thereof that when expressed in plants provide resistance or tolerance against PPO-type inhibitor herbicides thereby conferring the plant with a desirable trait for Herbicide Tolerance (HT).

Advantageously and surprisingly, while the structure and sequence of the residues composing the herbicide pocket exhibit a high similarity, several key structural/geometrical differences were identified, which may explain the advantageous differences in herbicide tolerance activity of the fungal PPO enzyme of the invention relative to human PPOX or plant PPO.

The invention includes amino acid sequences coding for PPO polypeptides derived or isolated from fungi and having enzymatic activity and complementing the plant's endogenous PPO enzyme.

In some embodiments, the fungal-derived PPO includes variants, mutants, motifs, fragments, and/or protein fusions thereof.

According to some aspects, there is provided a transgenic plant expressing an exogenous fungal-derived Protoporphy-rinogen Oxidase (PPO) enzyme comprises amino acid sequence having at least 80% similarity to at least one sequence as set forth in any one of SEQ ID NOs: 2, 94, 96-98, or any combination thereof, wherein the fungal-derived PPO comprises a pocket opening size of not more than 9.5 Angstrom as determined by comparing a simulated 3D structure/folding of the fungal-derived PPO with a crystal structure of human PPOX bound with acifluorfen, and wherein the simulated 3D structure/folding of the fungal-derived PPO is structurally aligned to the crystal structure of human PPO and is superimposed with acifluorfen, and wherein the fungal-derived PPO confers resistance or tolerance to at least one PPO-inhibitor herbicide.

In some embodiments, the exogenous fungal-derived PPO comprises an amino acid sequence having at least 90% similarity to at least one sequence as set forth in any one of SEQ ID NOs: 2, 94, 96-98, or any combination thereof.

In some embodiments, the pocket opening size of any one of the fungal-derived PPO comprises a difference of at least 2.1 Angstrom with respect to the pocket opening size of the human PPOX.

According to some embodiments, the exogenous fungal-derived PPO comprises a first arginine at a position structurally corresponding to arginine at position 97 in human PPOX (human Arg97) and/or a second arginine at a position structurally corresponding to arginine at position 62 in human PPOX (human Arg62), wherein the first and/or second arginine of the fungal-derived PPO have a different geometrical orientation, compared to the human Arg62 and/or human Arg97 geometrical orientation as determined by comparing a simulated 3D structure/folding of fungal-derived PPO with a crystal structure of human PPOX bound with acifluorfen, and wherein the simulated 3D structure/folding of fungal-derived PPO is structurally aligned to the crystal structure of human PPO and is superimposed with acifluorfen.

In some embodiments, the different geometrical orientation comprises a different distance of the first arginine of the fungal-derived PPO from a superimposed acifluorfen, and wherein the distance comprises a first distance (d1) between the guanidinium group of the first arginine residue of the fungal-derived PPO, and a hydroxyl of C11 of the superimposed acifluorfen, and wherein d1 is more than 5.5 Angstrom.

In some embodiments, the different geometrical orientation comprises a different distance of the second arginine of the fungal-derived PPO from a superimposed acifluorfen, and wherein the distance comprises a second distance (d2) between the guanidinium group of the second arginine residue of the fungal-derived PPO, and a carbonyl oxygen of C11 of a superimposed acifluorfen, and wherein d2 is more than 5 Angstrom.

In some embodiments, a sum of the distances of d1 and d2 is more than about 11 Angstrom.

In some embodiments, the sum of the distances of d1 and d2 of the fungal-derived PPO is different in more than about 7.3 Angstrom than a sum of distances of d1 and d2 of the human PPOX, and wherein the d1 and d2 of the human PPOX are the distances between the guanidinium group of human Arg97 and a hydroxyl of C11 of acifluorfen (d1 human PPOX) and of human Arg62 and a carbonyl of C11 of acifluorfen (d2 human PPOX), as determined by comparing a simulated 3D structure/folding of fungal-derived PPO with a crystal structure of human PPOX bound with acifluorfen, and wherein the simulated 3D structure/folding of fungal-derived PPO is structurally aligned to the crystal structure of human PPO and is superimposed with acifluorfen.

In some embodiments, the exogenous fungal-derived PPO comprises an amino acid sequence having at least 80% similarity to at least one sequence as set forth in any one of SEQ ID NOs: 2, 94, 96-98, or any combination thereof.

In some embodiments, the exogenous fungal-derived PPO comprises an amino acid sequence having at least 90% similarity to at least one sequence as set forth in any one of SEQ ID NOs: 2, 94, 96-98, or any combination thereof.

According to some embodiments, the exogenous fungal-derived PPO comprises a phenylalanine at a position 404 (F404) which structurally corresponds to valine at position 347 (V347) of human PPOX, as determined by comparing a simulated 3D structure/folding of fungal-derived PPO with a crystal structure of human PPOX bound with acifluorfen, and wherein the simulated 3D structure/folding of fungal-derived PPO is structurally aligned to the crystal structure of human PPO and is superimposed with acifluorfen.

According to some embodiments, the exogenous fungal-derived PPO comprises a phenylalanine at a position 383 (F383) which structurally corresponds to a phenylalanine at position 331 (F331) of human PPOX, as determined by comparing a simulated 3D structure/folding of fungal-derived PPO with a crystal structure of human PPOX bound with acifluorfen, and wherein the simulated 3D structure/ folding of fungal-derived PPO is structurally aligned to the crystal structure of human PPO and is superimposed with acifluorfen.

In some embodiments, the exogenous fungal-derived PPO comprises an amnio acid sequence having at least 80% similarity to a sequence as set forth in SEQ ID NO: 96.

In some embodiments, the exogenous fungal-derived PPO comprises an amnio acid sequence having at least 90% similarity to a sequence as set forth in SEQ ID NO: 96.

In some embodiments, the exogenous fungal-derived PPO confers resistance or tolerance to at least one PPO-inhibitor herbicide.

In some embodiments, the one or more PPO inhibitors is selected from the group consisting of herbicide families Phenylpyrazoles, Pyrimidindiones, Oxazolidinedione, Diphenylethers, Oxadiazoles, N-phenylphthalimides, Triazinone, Thiadiazoles, Triazolinones, and Triazolopyridinones, or any combination thereof.

In some embodiments, the fungal-derived PPO belongs to a fungal species of the clade leotiomyceta.

In some embodiments, the fungal-derived PPO belongs to a fungal species selected from *Aspergillus* sp., *Penicillium* sp., *Trichoderma* sp., *Rhodotorula* sp., *Hesseltinella* sp.

In some embodiments, the exogenous fungal-derived PPO has less than 40% similarity to an amino acid sequence of an endogenous plant PPO enzyme.

In some embodiments, the exogenous fungal-derived PPO enzyme further comprises a plant chloroplast transit peptide.

In some embodiments, the plant is selected from the group consisting of maize, wheat, rice, barley, soybean, cowpea, chickpea, cotton, sorghum, beans, rapeseed/canola, alfalfa, flax, sunflower, safflower, millet, rye, sugarcane, sugar beet, cocoa, tea, *Brassica*, coffee, sweet potato, flax, peanut, clover; lettuce, tomato, cucurbits, cassava, potato, carrot, radish, pea, lentils, cabbage, cauliflower, broccoli, brussels sprouts, peppers, pineapple, citrus, apples, pears, peaches, apricots, walnuts, avocado, banana, palm, *eucalyptus*, poplar, pine, coconut, orchids, *petunia*, carnations, roses, switchgrass, prairie grasses, indian grasses, big bluestem grass, camelina, or any combination thereof.

In some embodiments, the plant is selected from the group consisting of maize, wheat, rice, soybean, cowpea, chickpea, cotton, sorghum, rapeseed/canola, alfalfa, sunflower, sugarcane, sugar beet, camelina, or any combination thereof.

In some embodiments, the one or more PPO inhibitors is selected from the group consisting of herbicide families Phenylpyrazoles, Pyrimidindiones, Oxazolidinedione, Diphenylethers, Oxadiazoles, N-phenylphthalimides, Triazinone, Thiadiazoles, Triazolinones, and Triazolopyridinones, or any combination thereof.

In some embodiments, the plant is a broad leaf plant.

According to some embodiments, the comparing of the 3D structure/folding of fungal-derived PPO with a crystal structure of human PPO bound with acifluorfen, comprises comparing a simulated structure of the folding of fungal-derived PPO or a crystal structure showing the folding fungal-derived PPO.

According to some aspects, there is provided a transgenic plant expressing an exogenous fungal-derived Protoporphyrinogen Oxidase (PPO) enzyme conferring resistance or tolerance to at least one PPO-inhibitor herbicide, wherein the fungal-derived PPO enzyme comprises an amino acid sequence having at least 80% similarity to at least one sequence as set forth in any one of SEQ ID NOs: 1-7 and SEQ ID NOs: 86, 88-89, 91-99, or any combination thereof.

In some embodiments, the fungal-derived PPO enzyme comprises an amino acid sequence having at least 90% similarity to at least one sequence as set forth in any one of SEQ ID NOs: 1-7 and SEQ ID NOs: 86, 88-89, 91-99, or any combination thereof.

According to some embodiments, the fungal-derived PPO enzyme comprises a pocket opening size of not more than 9.5 Angstrom, as determined by comparing a simulated 3D structure/folding of fungal-derived PPO with a crystal structure of human PPOX bound with acifluorfen, and wherein the simulated 3D structure/folding of fungal-derived PPO is structurally aligned to the crystal structure of human PPO and is superimposed with acifluorfen.

According to some embodiments, the exogenous fungal-derived PPO comprises a first arginine at a position structurally corresponding to arginine at position 97 in human PPOX (human Arg97) and/or a second arginine at a position structurally corresponding to arginine at position 62 in human PPOX (human Arg62), wherein the first and/or second arginine of the fungal-derived PPO have a different geometrical orientation, compared to the human Arg62 and/or human Arg97 geometrical orientation, as determined by comparing a simulated 3D structure/folding of fungal-derived PPO with a crystal structure of human PPOX bound with acifluorfen, and wherein the simulated 3D structure/folding of fungal-derived PPO is structurally aligned to the crystal structure of human PPO and is superimposed with acifluorfen.

According to some embodiments, the exogenous fungal-derived PPO comprises a phenylalanine at a position 404 (F404) which structurally corresponds to valine at position 347 (V347) of human PPOX, as determined by comparing a simulated 3D structure/folding of fungal-derived PPO with a crystal structure of human PPOX bound with acifluorfen, and wherein the simulated 3D structure/folding of fungal-derived PPO is structurally aligned to the crystal structure of human PPO and is superimposed with acifluorfen.

According to some embodiments, the exogenous fungal-derived PPO comprises a phenylalanine at a position 383 (F383) which structurally corresponds to a phenylalanine at position 331 (F331) of human PPOX, as determined by comparing a simulated 3D structure/folding of fungal-derived PPO with a crystal structure of human PPOX bound with acifluorfen, and wherein the simulated 3D structure/folding of fungal-derived PPO is structurally aligned to the crystal structure of human PPO and is superimposed with acifluorfen.

In some embodiments, the fungal-derived PPO comprises an amino acid sequence having less than 40% similarity to an amino acid sequence of an endogenous plant PPO enzyme.

In some embodiments, the fungal-derived PPO enzyme further comprises a plant chloroplast transit peptide.

In some embodiments, the fungal-derived PPO belongs to a fungal specie selected from *Aspergillus* sp., *Fusarium* sp., *Rhizopus* sp., *Penicillium* sp., *Trichoderma* sp., *Rhodotorula* sp., *Hesseltinella* sp., *Spizellomyces* sp. *Rhizophagus* sp., *Alternariav* sp., and *Cladosporium* sp.

In some embodiments, the fungal-derived PPO enzyme belongs to a fungal species selected from the group consisting of *Aspergillus, Fusarium, Rhizopus, Penicillium*, and *Trichoderma*.

In some embodiments, the fungal-derived PPO belongs to a fungal species selected from *Aspergillus* sp., *Penicillium* sp., *Trichoderma* sp., *Rhodotorula* sp., *Hesseltinella* sp.

In some embodiments, the fungal-derived PPO enzyme belongs to a fungal species of the clade leotiomyceta.

In some embodiments, the plant is selected from the group consisting of maize, wheat, rice, barley, soybean, cowpea, chickpea, cotton, sorghum, beans, rapeseed/canola, alfalfa, flax, sunflower, safflower, millet, rye, sugarcane, sugar beet, cocoa, tea, *Brassica*, coffee, sweet potato, flax, peanut, clover; lettuce, tomato, cucurbits, cassava, potato, carrot, radish, pea, lentils, cabbage, cauliflower, broccoli, brussels sprouts, peppers, pineapple, citrus, apples, pears, peaches, apricots, walnuts, avocado, banana, palm, *eucalyptus*, poplar, pine, coconut, orchids, *petunia*, carnations, roses, switchgrass, prairie grasses, indian grasses, big bluestem grass, camelina, or any combination thereof.

In some embodiments, the plant is selected from the group consisting of maize, wheat, rice, soybean, cowpea, chickpea, cotton, sorghum, rapeseed/canola, alfalfa, sunflower, sugarcane, sugar beet, camelina, or any combination thereof.

In some embodiments, the one or more PPO inhibitors is selected from the group consisting of herbicide families Phenylpyrazoles, Pyrimidindiones, Oxazolidinedione, Diphenylethers, Oxadiazoles, N-phenylphthalimides, Triazinone, Thiadiazoles, Triazolinones, and Triazolopyridinones, or any combination thereof.

In some embodiments, the plant is a broad leaf plant.

In some embodiments, the plant is a cereal plant.

According to some aspects, there is provided a seed of the transgenic plant according to any one of the preceding embodiments.

According to some aspects, there is provided a product derived from the transgenic plant according to any one of the preceding embodiments.

According to some aspects, there is provided a method of controlling weeds growth where crop plants are growing, using at least one PPO inhibitor herbicide, wherein the crop plants comprise the transgenic plant according to embodiments of the present invention, the method comprising applying a weed-controlling amount of the one or more PPO inhibitor herbicide.

In some embodiments, the one or more PPO inhibitors are selected from the group consisting of herbicides families Phenylpyrazoles, Pyrimidindiones, Oxazolidinedione, Diphenylethers, Oxadiazoles, N-phenylphthalimides, Triazinone, Thiadiazoles, Triazolinones, and Triazolopyridinones, or any combination thereof.

According to some aspects, there is provided a method for conferring resistance or tolerance to one or more PPO inhibitor herbicide in a crop plant, the method comprising genetically modifying the plant to express an exogenous fungal-derived PPO enzyme, wherein the fungal-derived PPO enzyme comprises an amino acid sequence having at least 80% similarity to at least one sequence as set forth in any one of SEQ ID NOs: 1-7 or SEQ ID NOs: 86, 88-89, 91-99, or any combination thereof.

According to some embodiments, herein provided is a transgenic plant expressing an exogenous fungal-derived Protoporphyrinogen Oxidase (PPO) enzyme conferring resistance or tolerance to at least one PPO-inhibitor herbicide.

According to some embodiments, the fungal-derived PPO enzyme comprises an amino acid sequence having at least 70% similarity to fungal-isolated PPO.

According to some embodiments, wherein the fungal-derived PPO enzyme comprises an amino acid sequence having at least 70%, at least 80% or at least 90% similarity to at least one fungal-isolated sequences set forth in any one of SEQ ID NOs: 1-7 or 86-100, or any combination thereof. Each possibility is a separate embodiment.

According to some embodiments, the fungal-isolated PPO comprises any one or more of the sequences set forth in any one of SEQ ID NOs: 1-7 or 86-100, or any combination thereof. Each possibility is a separate embodiment.

According to some embodiments, the fungal-derived PPO comprises at least one amino acid motif having at least 85% similarity to a sequence set forth in any one of SEQ ID NOs: 16-85, or any combination thereof. Each possibility is a separate embodiment.

According to some embodiments, the fungal-derived PPO comprises at least one amino acid motif having at least 95% similarity to at least one sequence as set forth in any one of SEQ ID NOs: 16-85, or any combination thereof. Each possibility is a separate embodiment.

According to some embodiments, the fungal-derived PPO comprises at least 5 amino acids motifs having at least 85% similarity to a sequence as set forth in any one of SEQ ID NOs: 16-85; and wherein each motif is selected from a different group consisting of SEQ ID NOs: 16-22 or SEQ ID NOs: 23-29 or SEQ ID NOs: 30-36 or SEQ ID NOs: 37-43 or SEQ ID NOs: 44-50 or SEQ ID NOs: 51-57 or SEQ ID NOs: 58-64 or SEQ ID NOs: 65-71 or SEQ ID NOs: 72-78, or SEQ ID NOs: 79-85, or any combination thereof. Each possibility is a separate embodiment.

According to some embodiments, the fungal-derived PPO comprises 10 amino acids motifs having at least 85% similarity to a sequence as set forth in any one of SEQ ID NOs: 16-85, or any combination thereof; and wherein each motif is selected from a different group consisting of SEQ ID NOs: 16-22 or SEQ ID NOs: 23-29 or SEQ ID NOs: 30-36 or SEQ ID NOs: 37-43 or SEQ ID NOs: 44-50 or SEQ ID NOs: 51-57 or SEQ ID NOs: 58-64 or SEQ ID NOs: 65-71 or SEQ ID NOs: 72-78, or SEQ ID NOs: 79-85, or any combination thereof. Each possibility is a separate embodiment.

According to some embodiments, the fungal-derived PPO, has less than 50% similarity to an amino acid sequence of an endogenous plant PPO enzyme, in some instances less than 45%, in some instances less than 40%, in some instances less than 35%, in some instances less than 30%, in some instances less than 25%, in some instances less than 20%, in some instances less than 15%, in some instances less than 10%, in some instances less than 5%. Each possibility is a separate embodiment.

According to some embodiments, the motif of a fungal-derived PPO, has less than 50% similarity to an amino acid sequence of an endogenous plant PPO enzyme, in some instances less than 45%, in some instances less than 40%, in some instances less than 35%, in some instances less than 30%, in some instances less than 25%, in some instances less than 20%, in some instances less than 15%, in some instances less than 10%, in some instances less than 5%. Each possibility is a separate embodiment.

According to some embodiments, the RNA transcript of the fungal-derived PPO includes introns or lacks introns.

According to some embodiments, the fungal-derived PPO enzyme further comprises a plant chloroplast transit peptide.

According to some embodiments, the fungal-derived PPO is selected from the group consisting of *Aspergillus* sp., *Fusarium* sp., *Rhizopus* sp., *Penicillium* sp., *Trichoderma* sp., *Rhodotorula* sp., *Hesseltinella* sp., *Spizellomyces* sp. *Rhizophagus* sp., *Alternariav* sp., and *Cladosporium* sp., or any combination thereof. Each possibility is a separate embodiment.

According to some embodiments, the fungal-derived PPO enzyme is isolated from a fungus of a species selected from the group consisting of *Aspergillus, Fusarium, Rhizopus*, and *Penicillium*, or any combination thereof. Each possibility is a separate embodiment.

According to some embodiments, the fungal-derived PPO enzyme is isolated from *Aspergillus* awamori, *Aspergillus oryzae* or *Aspergillus miliusol, or any combination thereof.* Each possibility is a separate embodiment.

According to some embodiments, the fungal-derived PPO enzyme is isolated from *Fusarium venenatum* or *Fusarium fujikuroi*, or any combination thereof. Each possibility is a separate embodiment.

According to some embodiments, the fungal-derived PPO enzyme is isolated from *Rhizopus arrhizus, Rhizopus arrhizus* or *Rhizopus stolonifer*, or any combination thereof. Each possibility is a separate embodiment.

According to some embodiments, the fungal-derived PPO enzyme is isolated from *Penicillium oxalicum* or *Penicillium roqueforti*, or any combination thereof. Each possibility is a separate embodiment.

According to some embodiments, the fungal-derived PPO enzyme is isolated from *Trichoderma reesei.*

According to some embodiments, the fungal-derived PPO enzyme is isolated from *Rhodotorula toruloides.*

According to some embodiments, the fungal-derived PPO enzyme is isolated from *Hesseltinella vesiculosa.*

According to some embodiments, the fungal-derived PPO enzyme is isolated from *Spizellomyces* punctatus.

According to some embodiments, the fungal-derived PPO enzyme is isolated from *Rhizophagus irregularis.*

According to some embodiments, the transgenic plant is selected from the group consisting of maize, wheat, rice, barley, soybean, cowpea, chickpea, cotton, sorghum, beans, rapeseed/canola, alfalfa, flax, sunflower, safflower, millet, rye, sugarcane, sugar beet, cocoa, tea, *Brassica*, coffee, sweet potato, flax, peanut, clover; lettuce, tomato, cucurbits, cassava, potato, carrot, radish, pea, lentils, cabbage, cauliflower, broccoli, brussels sprouts, peppers, pineapple, citrus, apples, pears, peaches, apricots, walnuts, avocado, banana, palm, *eucalyptus*, poplar, pine, coconut, orchids, *petunia*, carnations, roses, switchgrass, prairie grasses, indian grasses, big bluestem grass, camelina, or any combination thereof. Each possibility is a separate embodiment.

According to some embodiments, the transgenic plant is selected from the group consisting of maize, wheat, rice, soybean, cowpea, chickpea, cotton, sorghum, rapeseed/canola, alfalfa, sunflower, sugarcane, sugar beet, camelina, or any combination thereof. Each possibility is a separate embodiment.

According to some embodiments, the transgenic plant is selected from the group consisting of maize, soybean, cotton, rapeseed/canola, or any combination thereof. Each possibility is a separate embodiment.

According to some embodiments, the one or more PPO inhibitors is selected from the group consisting of herbicide families Phenylpyrazoles, Pyrimidindiones, Oxazolidinedione, Diphenylethers, Oxadiazoles, N-phenylphthalimides, Triazinone, Thiadiazoles, Triazolinones, and Triazolopyridinones, or any combination thereof. Each possibility is a separate embodiment.

According to some embodiments, the transgenic plant expressing an exogenous fungal-derived Protoporphyrinogen Oxidase (PPO) enzyme conferring resistance or tolerance to at least one PPO-inhibitor herbicide is a broad leaf plant.

According to some embodiments, the transgenic plant expressing an exogenous fungal-derived Protoporphyrinogen Oxidase (PPO) enzyme conferring resistance or tolerance to at least one PPO-inhibitor herbicide is a seed.

According to some embodiments, a product derived from the transgenic plant expressing an exogenous fungal-derived Protoporphyrinogen Oxidase (PPO) enzyme conferring resistance or tolerance to at least one PPO-inhibitor herbicide According to some embodiments, herein provided is a method of controlling weeds growth where crop plants are growing, using at least one PPO inhibitor herbicide, wherein the crop plants comprise the transgenic plant, the method comprising applying a weed-controlling amount of the one or more PPO inhibitor herbicide.

According to some embodiments, the one or more PPO inhibitors are selected from the group consisting of herbicides families Phenylpyrazoles, Pyrimidindiones, Oxazolidinedione, Diphenylethers, Oxadiazoles, N-phenylphthalimides, Triazinone, Thiadiazoles, Triazolinones, and Triazolopyridinones, or any combination thereof.

According to some embodiments, herein provided is a method for conferring resistance or tolerance to one or more PPO inhibitor herbicide in a crop plant, the method comprising genetically modifying the plant to express an exogenous fungal-derived PPO enzyme.

According to some embodiments, the fungal-derived PPO enzyme comprises an amino acid sequence having at least 70% similarity to at least one sequence set forth in any one of SEQ ID NOs: 1-7.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The patent or application file contains at least one drawing executed in color. Copies of this patent or patent application publication with color drawing(s) will be provided by the Office upon request and payment of the necessary fee.

The invention will now be described in relation to certain examples and embodiments with reference to the following illustrative figures.

FIG. 1A shows a picture illustrating the degree of susceptibility *Arabidopsis* plants have towards Strike. WT plants were treated with low levels of Strike (Flumioxazin 50%, by Adama), 0.000015% and 0.00003% diluted in water.

FIG. 1B shows assessment of fungal-isolated PPO tolerance genes expressed in transgenic plants. Presented are the results of the two experiments (trials #1 and 2) performed using PPO-type inhibitor herbicides, Strike (Flumioxazin 50%, by Adama) or Aurora (40% Carfentrazone-Ethyl, by FMC), applied at concentrations ranging from 0.01% to 1% as indicated in the figure. The level of tolerance exhibited by the transgenic plants was assessed using a plant resilience score that was given in scale of 0-5 where '0' represents highly damaged plants and '5' represents highly resistant plants. The fungal-isolated genes include PPO from *Aspergillus* sp. (SEQ ID NO: 1, SEQ ID NO: 8 and SEQ ID NO: 2, SEQ ID NO: 9), *Fusarium* sp. (SEQ ID NO: 3, SEQ ID NO: 10, SEQ ID NO: 11, and SEQ ID NO: 12), *Rhizopus* sp. (SEQ ID NO: 6), and *Penicillium* sp. (SEQ ID NO: 14).

FIG. 3A shows representative pictures presenting plants resilience score in scale of 1-5 where '1' represents highly damaged plants and '5' represents highly resistant plants.

FIG. 3B shows a table presenting the results of an in-planta screening as a list of SEQ ID NOs of fungal-isolated PPO their fungal species, and the score they were given (based on the resilience scale of FIG. 3A) in the in-planta screening performed in the presence of Strike at concentration of 2.5 kg/hectare. The list includes fungal-isolated PPO genes without cTP having amino acid sequence as set forth in any one of SEQ ID NOs: 1-7 and 86-100; and their respective chimeric PPO genes with N-terminus cTP that were transformed to *Arabidopsis* plants and have amino acid sequences as set forth in any one of SEQ ID NOs: 8-14 and 104-108.

FIG. 3C shows a table presenting the results of an in-planta screening as a list of the 5 best SEQ ID NOs of fungal-isolated PPO genes and the score they were given (based on the resilience scale of FIG. 3A) in the in-planta screening performed in the presence of an array of 4 PPO-herbicides of Group 14, at increasing concentrations: Strike at concentration of 2.5 kg/hectare, Star at concentration of 1.25 kg/hectare, Goal at concentration of 1.15 kg/hectare, and Aurora at concentration of 1.0 kg/hectare. The list includes fungal-isolated PPO genes without cTP having amino acid sequence as set forth in any one of SEQ ID NOs: 2, 94, and 96-98; and their respective chimeric PPO genes with N-terminus cTP that were transformed to *Arabidopsis* plants and have amino acid sequences as set forth in any one of SEQ ID NOs: 9, 112 and 114-116.

FIG. 6A shows a schematic illustration presenting the hydrogen bonds formed between the guanidinium group of two arginine residues (e.g., Arg97 (d1) and Arg62 (d2) in human PPOX or other amino acid in corresponding positions based on structural alignment of fungal PPO)(see FIG. 6B), located within the herbicide binding pocket and the oxygen atom of the acifluorfen herbicide (crystalized with the human PPO), either at the hydroxyl (Distance 1; d1) or carbonyl groups (Distance 2; d2) of C11, respectively. Dashed yellow line represents the measured distance.

FIG. 6B shows amino acids residues, positions thereof, and amino acid at corresponding positions, that form the herbicide binding pocket of several PPOs that were structurally aligned. The structural alignment of the amino acid related to the herbicide binding pocket is presented in the format of a table. Residues which contribute to tolerance are marked in red and green. SEQ ID NO: 101 (*Homo sapiens* PPOX data is the crystallized form with acifluorfen) is the reference sequence for the structural alignment/positions and include arginine at position (Arg62) and arginine at position (Arg97) among the other amino acid at positions forming the pocket (i.e., positions 62, 97-98, 168-172, 314, 331-334, 344-347, 368 and/or 419 of SEQ ID NO: 101). Amino acids at positions structurally corresponding to the reference human positions are in SEQ ID NO: 102-103 and in SEQ ID NOs: 2, 94, 96-98. Human PPOX (SEQ ID NO: 101) together with soybean *Glycine Max* PPO (GmPPO from soybean) (SEQ ID NO: 102) are both are considered as PPO-herbicide susceptible/sensitive proteins.

DETAILED DESCRIPTION

Figures 1A, 1B:
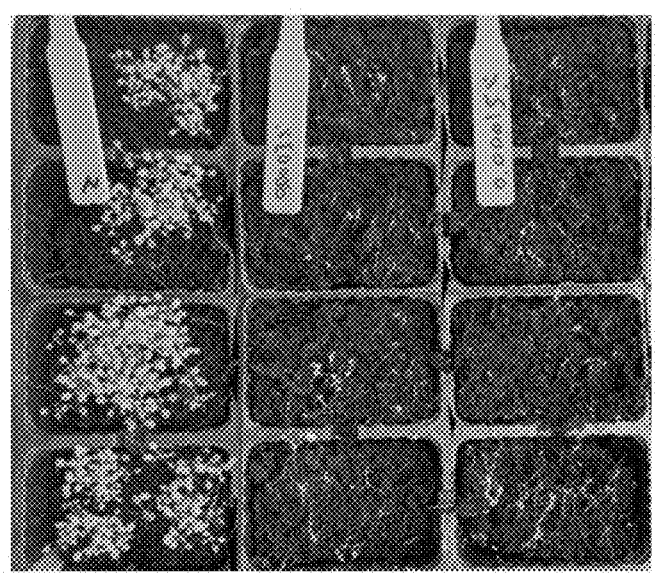
FIGS. 1A-1B present an assessment of PPO tolerance of WT *Arabidopsis* plants (FIG. 1A) and transgenic plants expressing fungal-isolated PPO (FIG. 1I1).

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

According to some aspects, the invention provides transgenic plant expressing an exogenous fungal-derived Protoporphyrinogen Oxidase (PPO) enzyme conferring resistance or tolerance to at least one PPO-inhibitor herbicide, wherein the fungal-derived PPO enzyme comprises an amino acid sequence having at least 80% similarity to fungal-isolated PPO.

According to some aspects, the invention discloses transgenic plants, cells, and seeds that have been genetically modified with exogenous fungal-derived PPO enzyme, variants, mutants, motifs, fragments and/or protein fusions thereof that when expressed in plants provide resistance or tolerance against PPO-type inhibitor herbicides thereby conferring the plant with a desirable trait for Herbicide Tolerance (HT). Each possibility is a separate embodiment.

In some embodiments, the included are amino acid sequences coding for PPO polypeptides derived or isolated from fungi and having enzymatic activity that complement the plant's endogenous PPO enzyme. In some embodiments, the fungal-derived PPO also includes variants, mutants, motifs, fragments and protein fusions thereof. Each possibility is a separate embodiment.

In some embodiments, methods are also provided for controlling weeds in a crop field by selectively protecting transgenic crop expressing fungal-derived PPO.

In a particular embodiment, the methods comprise introducing into a plant at least one expression cassette comprising a promoter operably linked to a nucleotide sequence that encodes a PPO polypeptide of the invention, variants, mutants, motifs, fragments and/or protein fusions thereof.

As used herein, the singular forms "a", "an" and "the" are intended to include the plural forms as well, unless the context clearly indicates otherwise. "a" and "an" are used herein to refer to one or more than one (i.e., to at least one) of the stated object. By way of example, "a nucleic acid" means one or more nucleic acids.

As used herein, "optional" or "optionally" means that the subsequently described event or circumstance does or does not occur, and that the description includes instances where said event or circumstance occurs and instances where it does not.

As used herein, the term "about" when referring to a measurable value such as an amount, a temporal duration, and the like, is meant to encompass variations of ±20% or in some instances±10%, or in some instances±5%, or in some instances±1%, or in some instances±0.1% from the specified value, as such variations are appropriate to perform the disclosed methods.

The term "PPO-inhibitor", "PPO-type inhibitor herbicide" or "PPO-herbicide" used herein, refers to substances that target the enzyme Protoporphyrinogen Oxidase (PPO) and inhibit its catalytic activity, thereby, preventing the enzyme from participating in the catalysis of the organic compound Protoporphyrin IX—a precursor of heme and chlorophyll. The terms may be used interchangeably.

Protoporphyrinogen Oxidase inhibitors (PPO-inhibitors) are a class of herbicides that inhibit plant growth by interfering with the biosynthesis of heme thereby blocking oxygen from being carried into chloroplasts. Inhibition of PPO oxidation enzymatic activity not only attenuates photosynthesis due to blockage of the production of heme and chlorophyll but also results in forming highly reactive molecules that attack and destroy lipids and protein membranes, causing cells and organelles to become leaky and disintegrate rapidly.

Non-limiting examples of PPO-type inhibitor herbicides include the following herbicide families, the Phenylpyrazoles, Pyrimidindiones, Oxazolidinedione, Diphenylethers, Oxadiazoles, N-phenylphthalimides, Triazinone, Thiadiazoles, Triazolinones, and Triazolopyridinones and their commercial names are, for example, Star, Goal, Strike and Aurora. Such herbicides include the active compounds flumioxazin, fomesafen, fluthiacet, carfentrazone, sulfentrazone, acifluorfen, lactofen, flumiclorac, saflufenacil, or others.

As used herein, the term "confer" refers to providing a characteristic or trait, such as herbicide tolerance or resistance, to a plant, such as these plants grow and develop without or with minor herbicidal effect in the presence of the herbicide.

As used herein, plants that are substantially "tolerant" to a herbicide exhibit, when treated with said herbicide, a dose/response curve which is shifted to the right with respect to the same dose/response exhibited by non-tolerant plants (i.e., a tolerant plant will require using higher concentrations of herbicide to show the same herbicidal effect exhibited by the non-tolerant plant). Tolerant plants will typically require at least twice as much herbicide as non-tolerant plants in order to produce a given herbicidal effect. Plants that are substantially "resistant" to the herbicide exhibit few, if any of the symptoms that can occur within 1 to 2 hours after exposure and include browning (necrosis) of the tissue, lytic, chlorotic or other lesions or, at least, none that impact significantly on the growth and development of the plant, when subjected to the herbicide at concentrations and rates which are typically employed by the agricultural community to inhibit or kill weeds in the field. The terms "tolerance" and "resistance" may be interchangeably used.

As used herein, the terms "tolerant", "resistant", "improved resistance", "improved herbicide-tolerance", or "improved PPO-inhibitor tolerance" may be interchangeably used and may refer to the improved ability of fungal PPO (derived or isolated), variant, motifs, mutants, or fragments thereof, or protein fusions thereof, including for example, but not limited to chloroplast transit peptide (cTP), to confer enhanced/increased/elevated tolerance against PPO-inhibitors when exogenously expressed in transgenic plants, relative to a plant that is unmodified (wt) or does not express the fungal PPO-derived gene but expresses an "empty vector" as control.

Alternatively, the terms "tolerant", may refer to the ability of transgenic plants to resist PPO-inhibitors herbicidal activity due to the expression of the exogenous fungal PPO, variant, motifs, mutants, or fragments thereof, or protein fusions thereof.

In some embodiments, the term "confer tolerance" may refer to, or include the improved ability of fungal PPO to confer enhanced/increased/elevated tolerance; or the ability of transgenic plants to resist to PPO-inhibitors herbicidal activity; relative to a plant that is unmodified (wt) or does not express the fungal PPO-derived gene but expresses an "empty vector" as control. Each possibility is a different embodiment.

In some embodiments, the improved ability of fungal PPO to confer enhanced/increased/elevated tolerance; or the ability of transgenic plants to resist to PPO-inhibitors herbicidal activity is determined by giving a plant a resilience score in scale of 1-5 where '1' represents highly damaged plants and '5' represents highly resistant plants; and if the score is at least 2, or preferably at least 3, or even preferably at least 4, or even preferably is 5, than the fungal PPO conferred the plant with enhanced/increased/elevated tolerance and the plant is resistant, relative to a wt plant or plant expressing an "empty vector" that scores 1. Each possibility is a different embodiment.

In some embodiments, the term "confer tolerance" comprises a score of at least 2, or preferably at least 3, or even preferably at least 4, or even preferably is 5. Each possibility is a different embodiment.

In this regard reference is preferably made to FIG. 3A, but may also be mad to FIG. 1B where the scale used was of 0-5 and where '0' represents highly damaged plants (no tolerance) and '5' represents highly resistant plants.

As used herein, the term "plant" refers to the whole plant, any parts thereof, or cultures thereof, such as a plant seed, a plant cell, a plant tissue, and a plant organ, at any stage of development. Examples of parts of a plant include but are not limited to meristems, roots, stems, leaves, flowers, fruits, and seeds, at any stage of development, in-planta, in-vitro, or in culture.

The disclosed invention can be applied to any plant or crop plant species, including, but not limited to, monocots and dicots. Examples of crop plant species include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum* meliaceous), foxtail millet (*Setaria italica*), finger millet (*Eleusine coracana*), sunflower (*Helianthus annuus*), safflower (Carthamus tinctorius), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), grapes (*Vitis vinifera*), palm trees from the Arecaceae (e.g, coconut palm (*Cocos mucifera*), oil palm (*Elaeis guineensis*), date palm (*Phoenix* spp.), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus* casica), guava (*Psidium guajava*), mango (*Mangifera indica*), olive (*Olea europaea*), papaya (*Carica papaya*), cashew (*Anacardium* occidentals), macadamia (Macadamia *integrifolia*), almond (*Prunus* amygdalus), *Eucalyptus* sp., *Pinus* spp., sugar beets (*Beta vulgaris*), sugarcane (*Saccharum* spp.), oats, barley, vegetables, ornamentals, lawn grasses (poaceae family) and conifers. Each possibility is a separate embodiment.

Additional examples of crop plant species include, but are not limited to cowpea, chickpea, beans, rapeseed/canola, clover; lettuce, tomato, cucurbits, carrot, radish, pea, lentils, cabbage, cauliflower, broccoli, brussels sprouts, peppers, apples, pears, peaches, apricots, walnuts, poplar, pine, orchids, *petunia*, carnations, roses, switchgrass, prairie grasses, indian grasses, big bluestem grass, camelina.

As used herein, the term "Fungal-derived" refers to a Protoporphyrinogen Oxidase (PPO) gene and gene products, or sequences thereof, as well as to variants, mutants, motifs, or fragments thereof, and include synthetic or cloned PPO or protein fusions thereof, that is expressed in a cell or represented in a library. The terms "Fungal-derived" and "PPO-derived" may be used interchangeably.

According to some embodiments, the fungal-derived PPO confers resistance or tolerance to at least one PPO-inhibitor herbicide.

According to some embodiments, the fungal-derived PPO have an amino acid sequence as set forth in any one of SEQ ID NO: 1-100.

According to some embodiments, the fungal-derived PPO is a fungal isolated PPO having an amino acid sequence as set forth in any one of SEQ ID NO: 1-7 or 86-100. Each possibility is a separate embodiment.

According to some embodiments, the fungal-derived PPO have an amino acid sequence of a PPO-derived motif as set forth in any one of SEQ ID NO: 16-85.

According to some embodiments, the fungal-derived PPO have an amino acid sequence comprising at least 60%, at least 70%, at least 80% at least 90% or at least 95% identity to fungal-isolated PPO.

According to some embodiments, the fungal-derived PPO have an amino acid sequence comprising at least 95% similarity to fungal-isolated PPO.

As used herein, the term "Fungal-isolated" refers to a native full-length PPO gene and gene products, or sequences thereof, originally isolated or extracted from fungi as genomic DNA or RNA (i.e., that was then processed to cDNA), and include synthetic or cloned PPO gene and gene products, or sequences thereof, or protein fusions thereof, that is expressed in a cell, or represented in a library.

According to some embodiments, the fungal-isolated PPO or fungal-derived PPO may be modified to include a signal peptide or a target peptide including for example, but not limited to chloroplast transit peptide (cTP).

In some embodiments, protein fusions of fungal-isolated PPO or fungal-derived PPO comprises fusion with chloroplast transit peptide (cTP).

According to some embodiments, the fungal-isolated PPO may be modified to achieve optimization of its function including for example, but not limited to by way of genetic codon usage optimization to be optimally expressed in a plant cell.

According to some embodiments, the fungal-isolated PPO or fungal-derived PPO of the invention, variants, mutants, motifs and/or fragments thereof, belongs to the clade leotiomyceta.

According to some embodiments, the fungal-derived or fungal-isolated PPO of the invention belong to the group consisting of *Aspergillus, Fusarium, Rhizopus, Penicillium, Trichoderma, Alternaria*, and *Cladosporium*.

According to some embodiments, the fungal-isolated PPO has an amino acid sequence as set forth in any one of SEQ ID NO: 1-7. Each possibility is a separate embodiment.

According to some embodiments, the fungal-derived PPO enzyme comprises an amino acid sequence having at least 70% similarity to fungal-isolated PPO, at least 75% similarity to fungal-isolated PPO, at least 80% similarity to fungal-isolated PPO, at least 85% similarity to fungal-isolated PPO, at least 90% similarity to fungal-isolated PPO, at least 95% similarity to fungal-isolated PPO, at least 96% similarity to fungal-isolated PPO, at least 97% similarity to fungal-isolated PPO at least 98% similarity to fungal-isolated PPO, at least 99% similarity to fungal-isolated PPO, at least 99.9% similarity to fungal-isolated PPO, or more. Each possibility is a separate embodiment According to some embodiments, fungal-derived PPO comprises fungal-isolated PPO.

According to some embodiments, fungal-derived PPO sequences share, with respect to each other, at least 60% similarity, in some instances at least 65% similarity, in some instances at least 70% similarity, in some instances at least 75% similarity, in some instances at least 80% similarity, in some instances at least 85% similarity, in some instances least 90% similarity, in some instances at least 95% similarity, in some instances at least 96%, in some instances at least 97%, in some instances at least 98%, or in some instances at least 99% similarity.

According to some embodiments, the fungal-derived nucleic acid template is used to amplify PPO; in some embodiments, the fungal-derived nucleic acid template used to amplify PPO is a fungal genomic DNA template or the transcript of mRNA template; in some embodiments, the fungal-derived nucleic acid template used to amplify PPO is synthetic or clonal PPO expressed in a cell or represented by a library. Each possibility is a separate embodiment.

According to some embodiments, the RNA transcript of the fungal-derived PPO sequence of the invention, includes introns; According to some embodiments, the RNA transcript of the fungal-derived PPO sequence of the invention, completely lacks or partially lacks introns; According to some embodiments, the RNA transcript of the fungal-derived PPO sequence of the invention, includes at least one intron, or at least 2 introns, or at least 5 introns, or at least half the number of introns of the full-length native transcript. Each possibility is a separate embodiment.

According to some embodiments, the RNA transcript of the fungal-derived PPO polypeptide of the invention, is expressed as a fully mature intron-less RNA product; according to some embodiments, the RNA transcript of the fungal-derived PPO polypeptide of the invention, is expressed as an un-spliced or partially spliced pre-mature RNA product. Each possibility is a separate embodiment.

The terms "similarity" and "sequence similarity" may be interchangeably used and refer hereinafter to the level of "identities" or "positives" between two sequences when they are compared by aligning them using an alignment tool. As used herein, the similarity is with respect to a directly compared fungal-derived PPO or fungal-isolated PPO, or to any other PPO genes or sequences being directly referred to, including but not limited to genes from plants, humans, or other organisms.

As used herein, the term "identities" means that the two aligned residues are the same. As used herein, the term "positives" means that two aligned residues are not the same, but they share chemical, physical and/or structural characteristics that make them practically replaceable. For example, Lysine and Arginine are both positively charged amino acids and are therefore considered as "positive" with respect to each other, and Aspartate and Glutamate are negatively charged amino acids and therefore are also considered as "positive" with respect to each other.

In some embodiments, an amino acid sequence of a fungal-derived PPO comprises a % similarity to an amino acid sequence of a fungal-isolated PPO. In some embodiments, an amino acid sequence of a fungal-derived PPO comprises a % identity to an amino acid sequence of a fungal-isolated PPO.

In some embodiments, the % similarity of an amino acid sequence of a fungal-derived PPO comprises at least 60%, at least 65%, at least 70%, at least 75%, at least 80%, at least 81%, at least 82%, at least 83%, at least 84%, at least 85%, at least 86%, at least 87%, at least 88%, at least 88%, at least 89%, at least 90%, at least 91%, at least 92%, at least 93%, at least 94%, at least 95%, at least 96%, at least 97%, at least 98%, at least 99%, at least 99.9% similarity or more, to an amino acid sequence of a fungal-isolated PPO. Each possibility is a separate embodiment.

In some embodiments, the % identity of an amino acid sequence of a fungal-derived PPO comprises at least 30%, at least 35%, at least 40%, at least 45%, at least 50%, at least 51%, at least 52%, at least 53%, at least 54%, at least 55%, at least 56%, at least 57%, at least 58%, at least 59%, at least 60%, at least 65%, at least 66%, at least 67%, at least 68%, at least 69%, at least 70%, at least 71%, at least 72%, at least 73%, at least 74%, at least 75%, at least 80% identity or more, to an amino acid sequence of a fungal-isolated PPO. Each possibility is a separate embodiment.

As used herein, when comparing two amino acid sequences the level of similarity may refer to the degree of positivity between residues of the aligned sequence.

In some embodiments, the level of similarity between two amino acid sequences is the degree of positivity between residues of the aligned sequence (total % of the complete sequence). In some embodiments, the level of similarity between two amino acid sequences is the degree of identity (total %) between residues of the aligned sequence (total % of the complete sequence).

Sequence similarity, therefore, refers to the optimal matching of the residues (i.e. sequence similarity may be determined, for example, by multiple sequence alignment (MSA). The optimal matching is determined by an algorithm that finds the minimal number of edit operations (inserts, deletes, and substitutions) in order to align one sequence to another sequence. A sequence alignment tool, for example CLUSTALW, can be utilized to accurately compare, analyze, and identify the level of similarity between two or more fragments, variants, mutants, motifs, fragments and/or homologous sequences of proteins or genes with statistical confidence. According to some embodiments, the optimal matching may also be determined by an algorithm that finds spatial overlapping residues according to the structure or a model of the translated proteins. According to some embodiments, the optimal matching of two residues may also be determined according to a common part in the catalytic mechanism of two proteins.

Multiple sequence alignment (MSA) may be applied for analysis of sequence similarity (calculations of % similarity or % identity) based on optimal matching of the residues, as described hereinabove.

The terms "variants", "mutants", "motifs", and "fragments" of the disclosed nucleotide sequences and amino acid sequences of the proteins encoded thereby are also encompassed by the present invention and refer to similar sequences.

According to some embodiments, the present invention encompasses fungal-isolated or PPO-derived amino acid sequences, including variants, mutants, motifs, and fragments thereof that may have with respect to each other at least 60% similarity, in some instances at least 65% similarity, in some instances at least 70% similarity, in some instances at least 75% similarity, in some instances at least 80% similarity, in some instances at least 85% similarity, in some instances least 90% similarity, in some instances at least 95% similarity, in some instances at least 96%, in some instances at least 97%, in some instances at least 98%, or in some instances at least 99% similarity. Each possibility is a separate embodiment.

PPO-derived variants, mutants, motifs, or fragments of a fungal-derived polypeptide of the present invention may be encoded to retain the biological activity of the full-length fungal-isolated PPO protein, or they may have improved activity, or have increased or decreased activity with respect to the fungal-isolated PPO or other PPO-derived polypeptides including that particular sequence it derived from and including but not limited to other sequences from plants, humans, or other organisms.

As used herein the terms "variants" or "mutants" refer to similar sequences. The terms are used with respect to, fungal-derived sequence or to any other PPO genes or sequences being directly referred to, including but not limited to PPO genes from plants, humans, or other organisms.

A variant may refer to naturally occurring allelic variants (i.e., genetic diversity, polymorphism) when it is directly referred to, or it may refer to genetically engineered (i.e., mutated or changed forms) when directly referred. Otherwise, as used herein the terms variants and mutants may be interchangeably used.

A polynucleotide variant or mutant or a polypeptide variant or mutant, comprises a deletion, substitution and/or addition of one or more residue at one or more positions of the disclosed PPO-derived sequence. One of skill in the art will recognize that variants or mutants of the nucleic acids may be constructed such that an open reading frame is maintained, therefore variants or mutants of a nucleotide sequence may encode polypeptide or fragments thereof that retain the biological activity of the full-length fungal-isolated or PPO-derived protein, have improved activity, or have increased or decreased activity with respect to the fungal-isolated PPO or other PPO-derived polypeptides. For polynucleotides, conservative variants include those sequences that, because of the degeneracy of the genetic code, encode the amino acid sequence of the fungal-derived PPO polypeptides. Variants or mutants can be identified with the use of well-known molecular biology techniques, for example, with next generation sequencing (NGS), polymerase chain reaction (PCR) and hybridization techniques. Variants or mutated polynucleotides may be generated, for example, by using site-directed mutagenesis or solid phase synthesis. According to some embodiments, variants or mutants of a nucleotide sequence that encodes a functional fungal-derived protein will have at least about 50%, 55%, 60%, 65%, 70%, 75%, 80%, 85%, 90%, 91%, 92%, 93%, 94%, 95%, 96%, 97%, 98%, 99% or more sequence similarity to with respect to the fungal-isolated PPO or other PPO-derived including that particular polynucleotide it derived from, or at least about 60%, 65%, 70%, 75%, 80%, 85%, 90%, 91%, 92%, 93%, 94%, 95%, 96%, 97%, 98%, 99% or more sequence similarity to with respect to the fungal-isolated PPO or other PPO-derived polypeptides including that particular amino acid it derived from, as determined by a sequence alignment tool. Each possibility is a separate embodiment.

As used herein, the term "motif" refers to a continuous sequence of amino acids in a polypeptide that may include specific patterns of amino acid residues and/or structures that characterize it.

According to some embodiments, a motif in a fungal-isolated or PPO-derived polypeptide may have a corresponding continuous sequence of amino acids in PPO polypeptides of plants, human, or other species. Such correspondence may be determined, for example, by optimal matching using multiple sequence alignment (MSA).

According to some embodiments, a motif of the invention may be in a fungal-derived PPO polypeptide or fungal-isolated polypeptide that shares similarity at least across *Aspergillus, Fusarium, Rhizopus, Penicillium, Trichoderma, Alternaria* and *Cladosporium.*

According to some embodiments, a motif of the invention may be in a fungal-derived PPO polypeptide or fungal-isolated polypeptide that shares similarity at least across *Aspergillus*, Fusarium, Rhizopus, Penicillium.

According to some embodiments, the fungal-derived PPO polypeptide or fungal-isolated polypeptide shares similarity at least across *Aspergillus, Fusarium, Rhizopus, Penicillium, Trichoderma, Alternaria* and *Cladosporium* According to some embodiments, the fungal-derived PPO polypeptide or fungal-isolated polypeptide shares similarity at least across *Aspergillus*, Fusarium, Rhizopus, Penicillium.

According to some embodiments, motifs of the invention may be any sequence that shares at least about 60%, 65%, 70%, 75%, 80%, 85%, 90%, 91%, 92%, 93%, 94%, 95%, 96%, 97%, 98%, 99% or more sequence similarity to the amino acid sequence set forth in any one of SEQ ID Nos: 16-85.

According to some embodiments, a motif of the present invention may retain the biological activity of the full-length fungal-isolated PPO protein, or it may have improved activity, enhanced, or decreased with respect to the fungal-isolated PPO or other PPO-derived polypeptides including that particular sequence it derived from.

According to some embodiments, a motif of the present invention includes at least about 2 amino acids, at least about 4 amino acids, at least about 10 amino acids, at least about 15 amino acids, at least about 20 amino acids, at least about 25 amino acids, at least about 30 amino acids, at least about 40 amino acids, or at least about 45 amino acids. Each possibility is a different embodiment.

According to some embodiments, a motif of the present invention includes about 2 to about 50 amino acids, about 4 to about 45 amino acids, about 10 to about 40 amino acids, about 15 to about 35 amino acids, or about 15 to about 30 amino acids. Each possibility is a different embodiment.

According to some embodiments, the fungal-derived PPO polypeptides disclosed herein comprise 10 motifs. According to some embodiments, motif 1 comprises any one of the amino acids set forth in SEQ ID NOs: 16-22; motif 2 comprises any one of the amino acids set forth in SEQ ID NOs: 23-29; motif 3 comprises any one of the amino acids set forth in SEQ ID NOs: 30-36; motif 4 comprises any one of the amino acids set forth in SEQ ID NOs: 37-43; motif 5 comprises any one of the amino acids set forth in SEQ ID NOs: 44-50; motif 6 comprises any one of the amino acids set forth in SEQ ID NOs: 51-57; motif 7 comprises any one of the amino acids set forth in SEQ ID NOs: 58-64; motif 8 comprises any one of the amino acids set forth in SEQ ID NOs: 65-71; motif 9 comprises any one of the amino acids set forth in SEQ ID NOs: 72-78; and motif 10 comprises any one of the amino acids set forth in SEQ ID NOs: 79-85. Each possibility is a different embodiment.

According to some embodiments, the fungal-derived PPO polypeptides disclosed herein comprise 10 motifs. According to some embodiments, motif 1 comprises any one of the amino acids set forth in SEQ ID Nos: 16-22; motif 2 comprises any one of the amino acids set forth in SEQ ID Nos: 23-29; motif 3 comprises any one of the amino acids set forth in SEQ ID Nos: 30-36; motif 4 comprises any one of the amino acids set forth in SEQ ID Nos: 37-43; motif 5 comprises any one of the amino acids set forth in SEQ ID Nos: 44-50; motif 6 comprises any one of the amino acids set forth in SEQ ID Nos: 51-57; motif 7 comprises any one of the amino acids set forth in SEQ ID Nos: 58-64; motif 8 comprises any one of the amino acids set forth in SEQ ID Nos: 65-71; motif 9 comprises any one of the amino acids set forth in SEQ ID Nos: 72-78; and motif 10 comprises any one of the amino acids set forth in SEQ ID Nos: 79-85. Each possibility is a different embodiment.

As used herein, the term "fragment" refers to a portion of a nucleotide sequence or a portion of an amino acid sequence. According to some embodiments, a fragment of a nucleotide sequence that encodes a functional fungal-isolated or PPO-derived protein of the invention will encode at least 2, 4, 7, 10, 15, 25, 30, 40, 50, 60, 70, 80, 90, 100, 110, 120, 150, 180, 200, 250, 300, 350 contiguous amino acids, or up to the total number of amino acids present in the full-length polypeptide of the invention. Each possibility is a different embodiment.

On of skill in the art will recognize that fragments of the nucleic acids of the invention may be constructed such that an open reading frame is maintained, therefore variants, mutants, motifs, or fragments of a fungal-isolated or PPO-derived polypeptide of the present invention may be encoded to retain the biological activity of the full-length fungus-derived PPO protein, or they may have improved activity, or have increased or decreased activity with respect to the fungal-isolated PPO or other PPO-derived polypeptides including that particular sequence it derived from.

The terms "polypeptide", "peptide", and "protein" are used interchangeably herein to refer to a polymer of amino acid residues. The terms apply to amino acid polymers in which one or more amino acid residues is an artificial chemical analog of a corresponding naturally occurring amino acid, as well as to naturally occurring amino acid polymers. Polypeptides of the invention can be produced either from a nucleic acid disclosed herein, or by the use of standard molecular biology techniques. For example, a PPO polypeptide of the invention, variants, mutants, motifs, and/or fragments thereof can be produced by expression of a recombinant nucleic acid of the invention in an appropriate host cell, or alternatively by chemical synthesis or by a combination of ex-vivo procedures, such as protease digestion and purification.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein of the invention may comprise non-translated sequences within translated regions of the nucleic acid (e.g., introns) or may lack or partially lack such intervening non-translated sequences (e.g., as in cDNA).

As used herein, the term "genetically modified" refers to plants or cells thereof transformed with a nucleic acid of foreign/exogenous origin that has been introduced into their genome by transformation with agrobacterium, biolistics, protoplasts, viral expression (transient) etc. as known in the art, in order to achieve transient or stable expression of the transgene. The terms "genetically modified" and "transgenic" may be interchangeably used.

According to some embodiments, an expression cassette comprising a promoter operably linked to a nucleotide sequence that encodes a fungal-derived PPO polypeptide of the invention, variants, mutants, motifs, and/or fragments thereof may be introduced into plants. Generally, the expression cassette will comprise a selectable marker gene for the selection of transformed cells.

According to some embodiments, a fungal-derived PPO sequence is fused to a chloroplast transit peptide (cTP).

According to some embodiments, fungal-derived PPO sequences conferred high levels of tolerance to the transgenic plants against the PPO-inhibitor herbicides Strike and/or Aurora. Each possibility is a separate embodiment.

According to some embodiments, some fungal-derived PPO sequences conferred high levels of tolerance to the transgenic plants against the PPO-inhibitor herbicides Strike but not against Aurora. According to some embodiments, some fungal-derived PPO sequences conferred high levels of tolerance to the transgenic plants against the PPO-inhibitor herbicides Aurora but not against Strike.

According to some embodiments, high levels of tolerance means that the transgenic plants are more than about $10^4$ times (4 orders of magnitude) more tolerant than WT control plants.

According to some embodiments, very high levels of tolerance mean more than about $10^5$ (5 orders of magnitude) more tolerant to treatment as compared to WT or other plants that express an empty cassette without the fungal-derived gene and serve as control plants).

According to some embodiments, transgenic plants expressing fungal-derived PPO genes exhibit an advantageous improved growth across all range of concentration tested (0.01% to 0.5 for Aurora and 0.01% to 1% for Strike) and therefore have increased tolerance to both PPO-inhibitor herbicides when applied in a dose-dependent manner.

According to some embodiments, all PPO-genes derived from the genera of Aspergillus sp. (SEQ ID NO: 1, SEQ ID NO: 8, SEQ ID NO: 2, SEQ ID NO: 9 and SEQ ID NO: 86-88), Fusarium sp. (SEQ ID NO: 3, SEQ ID NO: 10, SEQ ID NO: 11, SEQ ID NO: 12, SEQ ID NO: 89 and 90), Rhizopus sp. (SEQ ID NO: 6 and SEQ ID NO: 91-93), Penicillium sp. (SEQ ID NO: 14, SEQ ID NO: 94 and SEQ ID NO: 95), Trichoderma sp. (SEQ ID NO: 96), Rhodotorula sp. (SEQ ID NO: 97), Hesseltinella sp. (SEQ ID NO: 98), Spizellomyces sp. (SEQ ID NO: 99) or Rhizophagus sp. (SEQ ID NO: 100) conferred high levels of tolerance to the transgenic plants against the PPO-inhibitor herbicides Strike and/or Aurora. Each possibility is a separate embodiment.

According to some embodiments, transgenic plants expressing genes of Aspergillus sp. (SEQ ID NO: 1, SEQ ID NO: 8 and SEQ ID NO: 2, SEQ ID NO: 9), genes of Fusarium sp. (for example, SEQ ID NO: 10 and SEQ ID NO: 12), and the gene of Rhizopus sp. (SEQ ID NO: 6) exhibited very high levels of resistance to strike. Each possibility is a separate embodiment.

According to some embodiments, transgenic plants expressing genes of Aspergillus sp. (for example, SEQ ID NO: 1, SEQ ID NO: 8, SEQ ID NO: 2, SEQ ID NO: 9) and the genes of Rhizopus sp. (SEQ ID NO: 6) and Penicillium sp. (SEQ ID NO: 14) exhibited very high levels of resistance to Aurora as compared to control plants. Each possibility is a separate embodiment.

According to some embodiments, Penicillium gene (SEQ ID NO: 14) conferred to the transgenic plant very high level of resistance against Aurora, but not against Strike.

According to some embodiments, Fusarium genes (for example, SEQ ID NO: 10 and SEQ ID NO: 12) conferred to the transgenic plant high levels of resistance against Strike, but not against Aurora.

According to some embodiments, transgenic plants expressing fungal-isolated PPO genes exhibit an advantageous improved growth across all range of concentration tested (0.01% to 0.5 for Aurora and 0.01% to 1% for Strike) and therefore have increased tolerance to both PPO-inhibitor herbicides when applied in a dose-dependent manner.

According to some embodiments, ten motifs (motifs 1-10) were recognized in fungal-derived PPO. According to some embodiments, the motifs are about 4 to about 30 amino acids in length.

According to some embodiments, motifs of fungal-isolated PPO sequences may share more common amino acid sequences and/or structural features between enzymes of Aspergillus, Fusarium, Rhizopus, and Penicillium, than the corresponding sequences of the plant derived-PPO share between enzymes of Arabidopsis, Tabacum, and Soybean, for example, motifs 1, 2, 3, 4, 6, 7, and 10. Each possibility is a separate embodiment.

According to some embodiments, motifs of fungal-derived PPO sequences may share more common amino acid sequences and/or structural features between themselves, than the corresponding sequences of the plant derived-PPO share between enzymes of plant.

According to some embodiments, a total of 70 motif sequences identified in fungal-isolated PPO enzymes of the genera *Aspergillus* sp., *Fusarium* sp., *Rhizopus* sp., and *Penicillium* sp., and are considered distinct and distinguishable with respect to their corresponding sequences in plants PPO enzyme.

According to some embodiments, the 70 motifs have an amino acid sequence as set forth in SEQ ID NO: 16-85.

According to some embodiments, a fungi-derived PPO polypeptide comprises 10 motifs considered as distinct and distinguishable with respect to their corresponding sequences in plants PPO enzyme.

According to some aspects, there is provided a transgenic plant expressing an exogenous fungal-derived Protoporphyrinogen Oxidase (PPO) enzyme comprising amino acid sequence having at least 80% similarity to a fungal-isolated PPO sequence as set forth in any one of SEQ ID NOs: 2, 94, 96-98, or any combination thereof. Each possibility is a separate embodiment.

In some embodiments, the exogenous fungal-derived PPO comprises an amino acid sequence having at least 90% similarity to fungal-isolated PPO sequence as set forth in any one of SEQ ID NOs: 2, 94, 96-98, or any combination thereof. Each possibility is a separate embodiment.

In some embodiments, the fungal-derived Protoporphyrinogen Oxidase (PPO) enzyme comprises amino acid sequence having at least 80% similarity, at least 81%, at least 82%, at least 83%, at least 84%, at least 85%, at least 86%, at least 87%, at least 88%, at least 88%, at least 89%, at least 90%, at least 91%, at least 92%, at least 93%, at least 94%, at least 95%, at least 96%, at least 97%, at least 98%, at least 99%, at least 99.9%, or more, to an amino acid sequence of a fungal-isolated PPO. Each possibility is a separate embodiment.

In some embodiments, the amino acid sequence of a fungal-isolated PPO comprises SEQ ID NOs: 2, 94, 96-98. Each possibility is a separate embodiment.

Reference is now made to FIGS. 3A-3C.

According to some embodiments, the fungal-derived PPO comprises a pocket opening size of less than 9.5 Angstrom.

According to some embodiments, the fungal-derived PPO comprises a pocket opening size of less than about 10 Angstrom, less than about 9.5 Angstrom, less than about 9.0 Angstrom, less than about 8.5 Angstrom, less than about 8.0 Angstrom, less than about 7.5 Angstrom, less than about 7.0 Angstrom, less than about 6.5 Angstrom, less than about 6.0 Angstrom, or less than about 5.5 Angstrom. Each possibility is a separate embodiment.

According to some embodiments, the fungal-derived PPO comprises a pocket opening size of between about 4.5 Angstrom to 9.5 Angstrom, between about 5.0 Angstrom to 9.0 Angstrom, between about 5.0 Angstrom to about 8.5 Angstrom, between about 5.0 Angstrom to about 8.5 Angstrom. Each possibility is a separate embodiment.

In some embodiments, the pocket opening size of any one of the fungal-derived PPO comprises a difference/reduction of at least 2.1 Angstrom with respect to the pocket opening size of the human PPOX.

In some embodiments, the pocket opening size of any one of the fungal-derived PPO comprises a difference/reduction of at least about 2.1 Angstrom, at least about 2.5 Angstrom, at least about 3.0 Angstrom, at least about 3.5, at least 4.0 Angstrom, at least 4.5 Angstrom, at least 5.0 Angstrom, or at least 5.5 Angstrom or more, with respect to the pocket opening size of the human PPOX. Each possibility is a separate embodiment.

In some embodiments, the pocket opening size of any one of the fungal-derived PPO comprises a difference/reduction between about 2.0 Angstrom to 6.0 Angstrom, between about 2.0 Angstrom to 5.5 Angstrom, between about 2.5 Angstrom to about 5.0 Angstrom, between about 3.0 Angstrom to about 4.5 Angstrom. Each possibility is a separate embodiment.

Figure 5A:
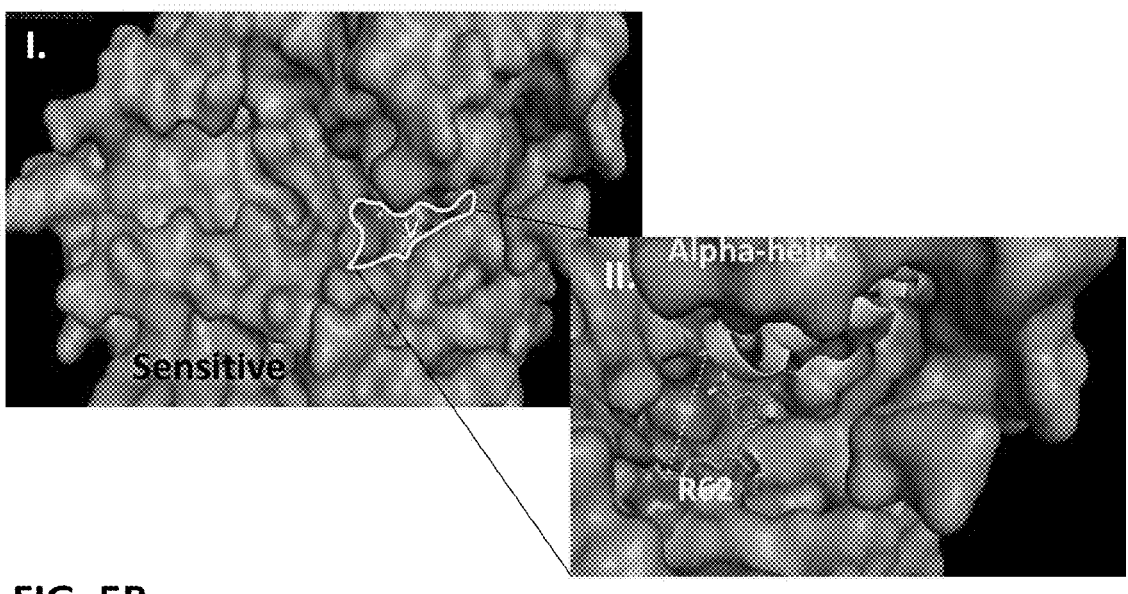
FIG. 5A shows a surface view illustration of the 3D structure of the human PPOX (SEQ ID NO: 101) presenting: (I) a frontal view of the herbicide binding pocket (defined by a yellow line); and (11) an alpha helix structure (shown in yellow) positioned in an identical orientation at the opening of the pocket of each one of the human, plant and fungal PPOs having amino acid sequence denoted by SEQ ID NOs: 101-103 and SEQ ID NOs: 2, 94, 96-98, even though their amino acid sequences are different. Also shown, a dashed yellow line representing the measured distance of the pocket opening size as defined and measured from a same position on the alpha helix where valine is at position 170 (V170) in human PPOX (or in structurally corresponding positions in SEQ ID NOs: 101-103 and SEQ ID NOs: 2, 94, 96-98), to arginine at position 62 (Arg62) (or in structurally corresponding positions in SEQ ID NOs: 101-103 and SEQ ID NOs: 2, 94, 96-98) which is at the widest point of the opening.
Figure 5B:
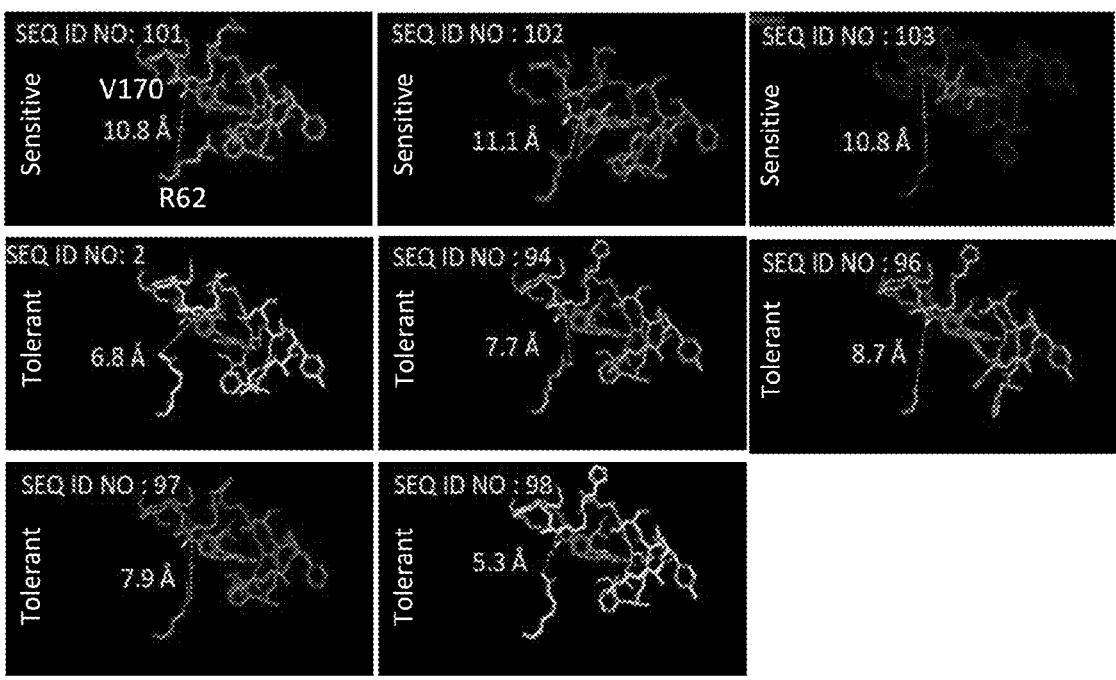
FIG. 5B shows the pocket opening size (yellow dashed line) of human sensitive PPO (SEQ ID NO: 101), plant sensitive PPOs (SEQ ID NOs: 102-103) and fungal tolerant PPOs (SEQ ID NOs: 2, 94, 96-98). The pocket opening size is measured as the distance between the amino group of the side chain of human Arg62, or amino acid at a structurally corresponding position in plant and fungal PPOs, to V170 of the human PPOX or amino acid at a structurally corresponding position in plant and fungal PPOs. The human V170, or amino acid at a structurally corresponding position in plant and fungal PPOs, is located in the alpha helix structure shown in FIG. 5A, whereas the human Arg62, or an amino acid at a structurally corresponding position in plant and fungal PPOs, is located at the widest point of the opening.

As used herein, the term "pocket opening size" refers to a space at the surface of the PPO enzyme through which where the herbicide enters its binding site, and is measured as a distance between the amino group of the side chain of human Arg62, or an amino acid in a structurally corresponding position in plant and fungal PPOs, to V170 of the human PPOX or an amino acid in a structurally corresponding position in fungal or plant PPOs. The human V170, or an amino acid in a structurally corresponding position in fungal or plant PPOs, is located in the alpha helix structure shown in FIG. 5A, whereas the human Arg62, or an amino acid in a structurally corresponding position in fungal or plant PPOs, is located at the widest point of the opening as seen in FIG. 5A and FIG. 5B.

In some embodiments, wherein the amino acid at a structurally corresponding position to human Arg62, in plant and fungal PPOs, is not arginine (i.e., see FIG. 6B: Q123 (SEQ ID NO: 102), T70 (SEQ ID NO: 103) or S102 (SEQ ID NO: 96)), distances were measured from the same position on the alpha helix to the amino group at the end of the side chain of Glutamine in SEQ ID NO: 102, or the methyl group at the end of the side chain of threonine in SEQ ID NO:103, or the hydroxyl group at the end of the side chain of serine in SEQ ID NO: 96. While these three amino acids have different chemical groups, structurally they occupy the same position and form the inner edge of the pocket opening so the distance measured was the smallest, so the specific atom was always located at the end of the side chain.

In some embodiments, the amino acid sequence of a fungal-isolated PPO comprises one or more of SEQ ID NOs: 2, 94, 96-98, or any combination thereof. Each possibility is a separate embodiment.

In some embodiments, the amino acid sequence of a fungal-isolated PPO comprises one or more of SEQ ID NOs: 2, 94, 97-98, or any combination thereof. Each possibility is a separate embodiment.

In some embodiments, the amino acid sequence of a fungal-isolated PPO comprises one or more of SEQ ID NOs: 2 and 98. Each possibility is a separate embodiment.

Reference is now made to FIGS. 5A-5C, FIG. 6B and Table 1.

In some embodiments, the fungal-derived PPO confers resistance or tolerance to at least one PPO-inhibitor herbicide.

In some embodiments, the fungal-derived PPO confers resistance or tolerance to at least one PPO-inhibitor herbicide, at least two, at least three, at least five, at least 7, or at least 10 PPO-inhibitor herbicide. Each possibility is a separate embodiment.

In some embodiments, the pocket opening size of the fungal-derived PPO is determined by comparing a simulated 3D structure/folding of the fungal-derived PPO with a crystal structure of human PPO bound with acifluorfen provided by PDB identifier: 4IVO.

In some embodiments, the simulated 3D structure/folding of the fungal-derived PPO is structurally aligned to the crystal structure of human PPO and is superimposed with acifluorfen.

As used herein, the term "simulated 3D structure/folding", "simulated structure" or "structural alignment" or "structure-based alignment" refers to computation/modeling of 3D structure/folding using structural alignment/structural simulation/structural homology and include superimposition of a target sequence, for example of fungal-PPOs, on a solved crystal structure in order to compute 3D structure/folding of the target sequence (i.e., the simulated structure) and determining structural similarity between the simulated structure and the crystal structure using RMSD (Root Mean Square Deviation) measurements. The simulation may include, for example, a fungal PPO sequence that is structurally aligned and superimposed to a crystal structure of human PPOX bound with acifluorfen, as provided by PDB identifier: 4IVO in order to simulate 3D structure/folding of the fungal PPO. In some embodiments thereof, the simulated 3D structure/folding of the fungal-derived PPO is superimposed with acifluorfen. In some preferred embodiments, the structural simulation is performed in accordance with the description of the method in preferred Example 5, but other embodiments may also refer to the description of Example 3.

The terms human PPO and human PPOX may be used interchangeably.

As used herein the term "comparing simulated 3D structure/folding" may refer, but is not limited to a comparison mad between a simulated 3D structure/folding of fungal-derived PPO superimposed with acifluorfen and the crystal structure of human PPOX bound with acifluorfen, as provided by PDB identifier: 4IVO; and may include, for example, but is not limited to: any structural similarities/differences (e.g., pocket opening size, distances, and geometrical orientation) that can be identified/measured and may relate to identities of amino acid at structurally corresponding positions, differences in geometrical orientation of amino acids at structurally corresponding positions, differences in geometrical orientation of structural elements (e.g., secondary and tertiary structures), measurements of distances or angles between different amino acids and distances or angles between amino acids and herebecides/acifluorfen.

In some embodiments, geometrical orientation comprises a direction, angular position, and/or distance, or any combination thereof. Each possibility is a separate embodiment. In some embodiments, geometrical orientation comprises distance.

As used herein the term "geometrical orientation" may be interpreted in its broad sense as accepted in the art when referring to a structural comparison between amino acid molecules/polymers positioned in 3D space, including reference to parameters including but not limited to the directions, angular positions, distances, and overall arrangement/identity of atoms and molecules in the 3D space. When structurally aligned and superimposed—two corresponding atoms/molecules/polymers may be characterized by differences in the herein-abovementioned non-limiting parameters of geometrical orientation, between themselves, and as a direct consequence of these difference between themselves—additional differences may exist such as but not limited to: distance from a reference point ("third party") that can be characterized/measured and compared. By way of example: when the sequence of the fungal PPO is structurally aligned and superimposed based on the human PPO crystal structure, and the two structures are compared—human Arg97 or human Arg62, each has different geometrical orientation with respect to an amino acid at a corresponding positions in fungal PPO, and as a direct consequence of this difference in their geometrical orientation—a difference may also exist in the measured distance between human Arg97 or human Arg62 to a reference point e.g., bound acifluorfen (the "third party") and the measured distance between their corresponding amino acid position to the same reference point e.g., superimposed acifluorfen (the "third party").

In some embodiments, the comparing of the 3D structure/folding of fungal-derived PPO with a crystal structure of human PPO bound with acifluorfen, comprises comparing a simulated structure of the folding of fungal-derived PPO.

In some embodiments, the comparing of the 3D structure/folding of fungal-derived PPO with a crystal structure of human PPO bound with acifluorfen, comprises comparing a crystal structure of fungal-derived PPO.

According to some embodiments, the exogenous fungal-derived PPO comprises a first arginine at a position structurally corresponding to arginine at position 97 in human PPOX (human Arg97) and/or a second arginine at a position structurally corresponding to arginine at position 62 in human PPOX (human Arg62). Each possibility is a separate embodiment.

In some embodiments, the first and/or second arginine of the fungal-derived PPO have a different geometrical orientation, compared to the human Arg62 and/or human Arg97 geometrical orientation. Each possibility is a separate embodiment.

In some embodiments, the position of the fungal-derived PPO structurally corresponding to Arg62 and/or Arg97 and the different geometrical orientation thereof are determined by comparing a simulated 3D structure/folding of fungal-derived PPO with a crystal structure of human PPO bound with acifluorfen provided by PDB identifier: 4IVO. Each possibility is a separate embodiment.

In some embodiments, the simulated 3D structure/folding of fungal-derived PPO is structurally aligned to the crystal structure of human PPO and is superimposed with acifluorfen.

As used herein, the terms "structurally corresponding" "position structurally corresponding to" or "structurally corresponding position" may be interchangeably used, and may refer to an amino acid position, for example of a fungal PPO, that are structurally homologous as determined by structural alignment/simulation of the 3D structure/folding of the fungal PPO. For example, a corresponding an amino acid position may compose the enzyme binding site of the herbicide according to FIG. 6B (e.g., SEQ ID NOs: 2, 94, 96-98 and 100, SEQ ID Nos: 102 and 103), and may be structurally corresponding to any one of the following positions of the human PPOX that compose the human enzyme herbicide binding site according to FIG. 6B i.e., positions 62, 97-98, 168-172, 314, 331-334, 344-347, 368 and/or 419 of SEQ ID NO: 101.

According to some embodiments, the different geometrical orientation comprises a different distance of the first arginine of the fungal-derived PPO from a superimposed acifluorfen, and wherein the distance comprises a first distance (d1) between the guanidinium group of the first arginine residue of the fungal-derived PPO, and a of Cl 1 of the superimposed acifluorfen, and wherein d1 is more than 5.5 Angstrom.

In some embodiments, distance (d1) is more than 5.5 Angstrom, is more than 6.0 Angstrom, is more than 6.3 Angstrom, is more than 6.5 Angstrom, is more than 7.0 Angstrom, is more than 7.2 Angstrom. Each possibility is a separate embodiment.

In some embodiments, distance (d1) is between 5.6 Angstrom and 7.5 angstrom, is between 5.6 Angstrom and 6.6 angstrom. Each possibility is a separate embodiment.

According to some embodiments, the different geometrical orientation comprises a different distance of the second arginine of the fungal-derived PPO from a superimposed acifluorfen, and wherein the distance comprises a second distance (d2) between the guanidinium group of the second arginine residue of the fungal-derived PPO, and a carbonyl oxygen of C11 of a superimposed acifluorfen, and wherein d2 is more than 5 Angstrom.

In some embodiments, distance (d2) is more than 5.0 Angstrom, is more than about 5.5 Angstrom, is more than about 6.5 Angstrom, is more than about 7.0 Angstrom, is more than about 7.5 Angstrom, is more than about 8.0 Angstrom, is more than about 8.5 Angstrom, is more than about 9.0 Angstrom, is more than about 9.5 Angstrom, is more than about 10.0 Angstrom. Each possibility is a separate embodiment.

In some embodiments, distance (d2) is between 5.0 Angstrom and about 10 Angstrom, is between about 6.5 Angstrom and about 9.5 angstrom, is between about 8.5 Angstrom and about 9.5 angstrom. Each possibility is a separate embodiment.

According to some embodiments, a sum of the distances of d1 and d2 is more than about 11 Angstrom.

In some embodiments, a sum of the distances of d1 and d2 is more than about 11 Angstrom, more than about 12 Angstrom, more than about 13 Angstrom, more than about 14 Angstrom, more than about 15 Angstrom, more than about 15.5 Angstrom. Each possibility is a separate embodiment.

In some embodiments, a sum of the distances of d1 and d2 is between about 11 Angstrom and about 16 Angstrom, or between about 13.5 Angstrom and about 16 Angstrom.

Each possibility is a separate embodiment.

According to some embodiments, the sum of the distances of d1 and d2 of the fungal-derived PPO is different in more than about 7.3 Angstrom than a sum of distances of d1 and d2 of the human PPOX, and wherein the d1 and d2 of the human PPOX are the distances between the guanidinium group of human Arg97 and a hydroxyl of C11 of acifluorfen (d1 human PPOX) and of human Arg62 and a carbonyl of C11 of acifluorfen (d2 human PPOX).

In some embodiments, the different geometrical orientation comprising d1 and d2 are determined by comparing a simulated 3D structure/folding of fungal-derived PPO with a crystal structure of human PPOX bound with acifluorfen provided by PDB identifier: 4IVO.

In some embodiments, the simulated 3D structure/folding of fungal-derived PPO is structurally aligned to the crystal structure of human PPO and is superimposed with acifluorfen.

Figure 6C:
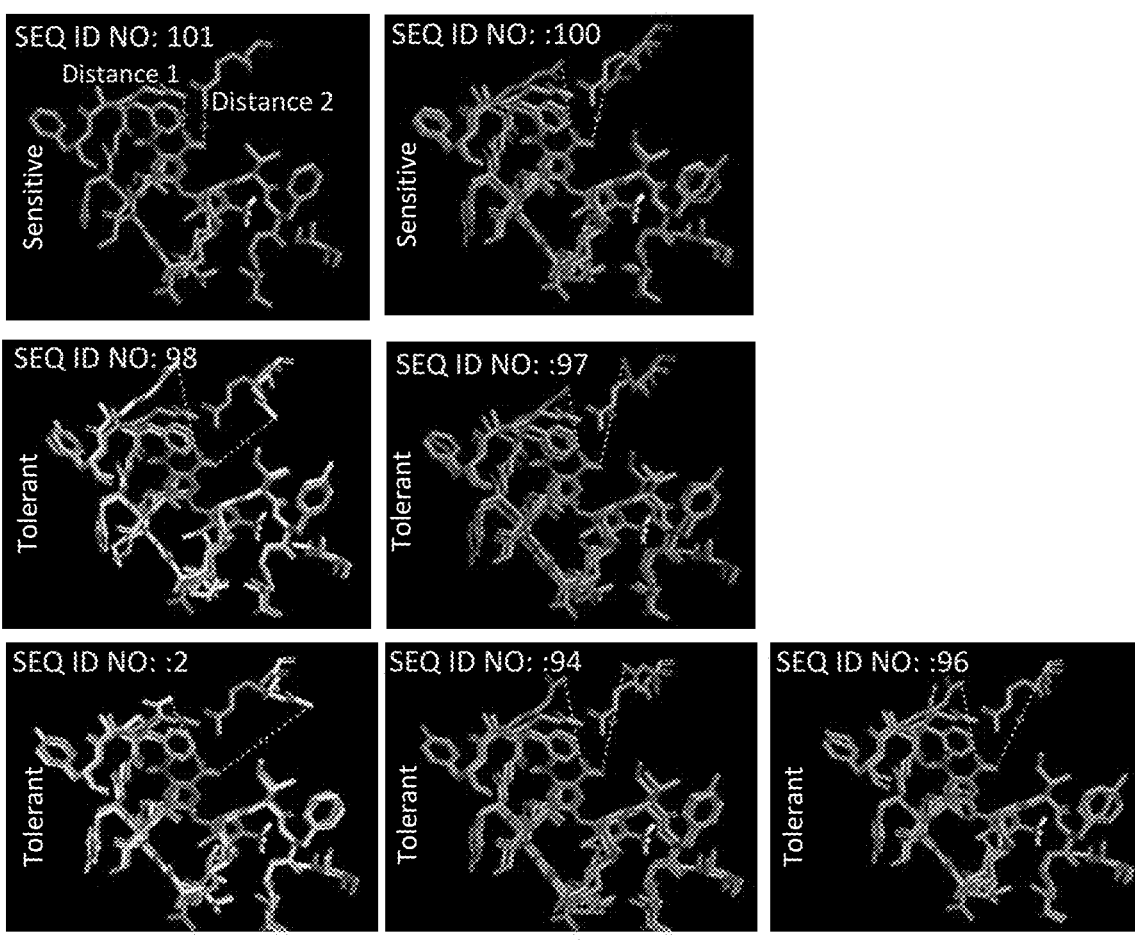
FIG. 6C distances of the hydrogen bonds between the herbicide Acifluorfen and the Arg62 and Arg97 in human PPOX, or other Arg in corresponding positions based on structural alignment of fungal PPO, in the herbicide binding domain pocket. Human PPO (SEQ ID NO: 101) in light green was superimposed with 3D predicted structures of fungal PPO proteins (SEQ ID: 100 and SEQ ID NO: 9, 94, and 96-98) and the hydrogen bonds were measured and summarized in Table 2. Longer distances corelate with the herbicide Star tolerance in a concentration of 1.25 kg/hectare. Dashed yellow line represents the measured distance.

Reference is now made to FIGS. 6A-6C and Table 2.

According to some embodiments, the exogenous fungal-derived PPO comprises an amino acid sequence having at least 80% similarity to fungal-isolated PPO sequence as set forth in any one of SEQ ID NOs: 2, 94, 96-98, or any combination thereof. Each possibility is a separate embodiment.

According to some embodiments, the exogenous fungal-derived PPO comprises an amino acid sequence having at least 90% similarity to fungal-isolated PPO as set forth in any one of SEQ ID NOs: 2, 94, 96-98, or any combination thereof. Each possibility is a separate embodiment.

In some embodiments, the fungal-derived Protoporphyrinogen Oxidase (PPO) enzyme comprises amino acid sequence having at least 80% similarity, at least 81%, at least 82%, at least 83%, at least 84%, at least 85%, at least 86%, at least 87%, at least 88%, at least 88%, at least 89%, at least 90%, at least 91%, at least 92%, at least 93%, at least 94%, at least 95%, at least 96%, at least 97%, at least 98%, at least 99%, at least 99.9%, or more, to an amino acid sequence of a fungal-isolated PPO. Each possibility is a separate embodiment.

In some embodiments, the amino acid sequence of a fungal-isolated PPO comprises the sequences denoted by any one of SEQ ID NOs: 2, 94, 96-98, or any combination thereof. Each possibility is a separate embodiment.

According to some embodiments, the exogenous fungal-derived PPO comprises a phenylalanine at a position 404 (F404) which structurally corresponds to valine at position 347 (V347) of human PPOX.

In some embodiments, the corresponding phenylalanine position of the fungal-derived PPO is determined by comparing a simulated 3D structure/folding of fungal-derived PPO with a crystal structure of human PPO bound with acifluorfen provided by PDB identifier: 4IVO.

In some embodiments, the simulated 3D structure/folding of fungal-derived PPO is structurally aligned to the crystal structure of human PPO and is superimposed with acifluorfen.

Figure 7:
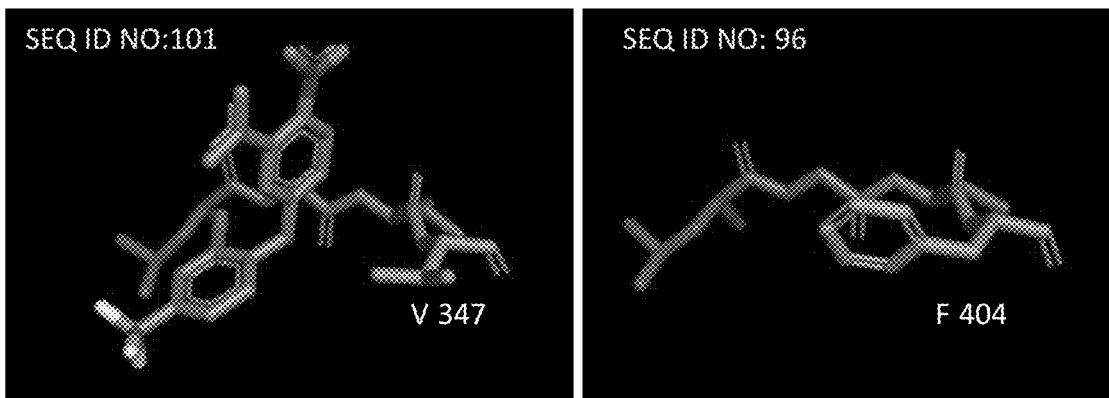
FIG. 7 shows a 3D illustration presenting a comparison between the geometrical orientation of valine V347 in the PPO binding pocket of the susceptible human PPOX denoted by SEQ ID NO: 101 and the corresponding (by structural alignment) phenylalanine F404 of the tolerant fungal PPO denoted by SEQ ID NO: 96 (see FIG. 6B). SEQ ID: 96 (on the right) exhibits a phenylalanine in a position that most other proteins have a Valine or Isoleucine. The added aromatic compound is facing into the pocket and interfering with the intermolecular bridge linking the amino acid moieties of the herbicide.

Reference is now made to FIG. 6B and FIG. 7.

According to some embodiments, the exogenous fungal-derived PPO comprises a phenylalanine at a position 383 (F383) which structurally corresponds to a phenylalanine at position 331 (F331) of human PPOX.

In some embodiments, the corresponding phenylalanine position of the fungal-derived PPO is determined by comparing a simulated 3D structure/folding of fungal-derived PPO with a crystal structure of human PPO bound with acifluorfen provided by PDB identifier: 4IVO.

In some embodiments, the simulated 3D structure/folding of fungal-derived PPO is structurally aligned to the crystal structure of human PPO and is superimposed with acifluorfen.

In some embodiments, the exogenous fungal-derived PPO comprises an amnio acid sequence having at least 80% similarity to fungal-isolated PPO sequence as set forth in SEQ ID NO: 96.

In some embodiments, the exogenous fungal-derived PPO comprises an amnio acid sequence having at least 90% similarity to fungal-isolated PPO of the sequence as set forth in SEQ ID NO: 96.

According to some embodiments, the exogenous fungal-derived PPO confers resistance or tolerance to at least one PPO-inhibitor herbicide.

In some embodiments, the one or more PPO inhibitors is selected from the group consisting of herbicide families Phenylpyrazoles, Pyrimidindiones, Oxazolidinedione, Diphenylethers, Oxadiazoles, N-phenylphthalimides, Triazinone, Thiadiazoles, Triazolinones, and Triazolopyridinones, or any combination thereof.

In some embodiments, the fungal-derived Protoporphyrinogen Oxidase (PPO) enzyme comprises amino acid sequence having at least 80% similarity, at least 81%, at least 82%, at least 83%, at least 84%, at least 85%, at least 86%, at least 87%, at least 88%, at least 88%, at least 89%, at least 90%, at least 91%, at least 92%, at least 93%, at least 94%, at least 95%, at least 96%, at least 97%, at least 98%, at least 99%, at least 99.9%, or more, to an amino acid sequence of a fungal-isolated PPO. Each possibility is a separate embodiment.

Figure 8:
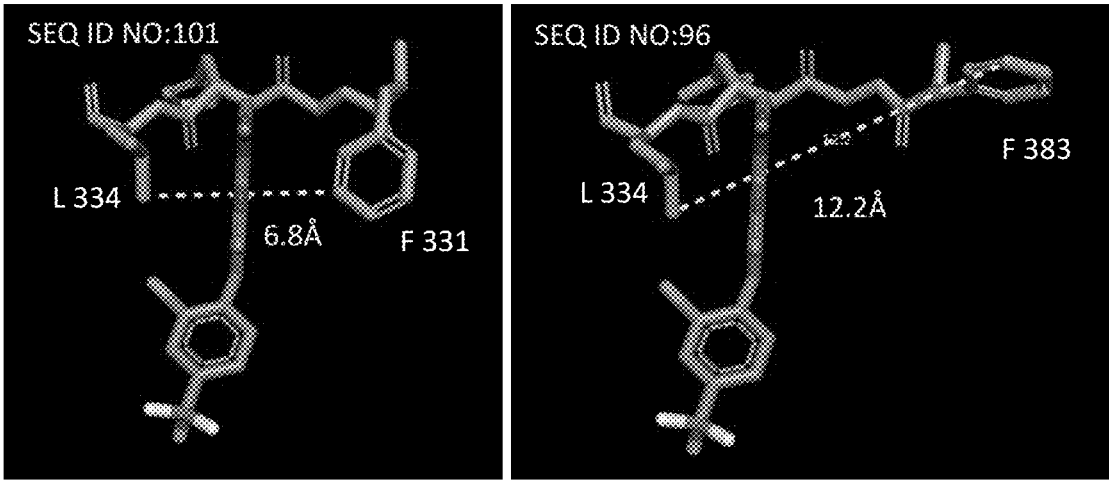
FIG. 8 shows a 3D illustration presenting a comparison between the geometrical orientation of phenylalanine F331 in the PPO binding pocket of the susceptible human PPOX denoted by SEQ ID NO: 101 and the corresponding (by structural alignment) phenylalanine F383 of the tolerant fungal PPO denoted by SEQ ID NO: 96 (see FIG. 6B). F331 together with Leucine at position 334 (FIG. 6B) stabilizes the herbicide molecule in the pocket of the human PPOX. Differently, SEQ ID NO:96 has Phenylalanine in a corresponding position F383, which is oriented perpendicular compared to the human PPOX, therefore the herbicide molecule is not stabilized inside the pocket, contributing to its tolerance.

Reference is now made to FIG. 6B and FIG. 8.

In some embodiments, a modes/mechanism of acquiring PPO-herbicide tolerance in fungal-derived or fungal-isolated PPOs comprises at least one of:

(i) reduced pocket opening size, affecting entry of the herbicide to the binding site (reduction in opening size);

(ii) de-stabilizing hydrogen bonds at positions corresponding (by structural alignment) to human position Arg62 and Arg97, affecting the binding to the herbicide (i.e., increased distance);

(iii) phenylalanine at a position 404 (F404) which structurally corresponds to valine at position 347 (V347) of human PPOX, affecting the binding to the herbicide (i.e., steric hindrance); and (iv) a phenylalanine at a position 383 (F383) which structurally corresponds to a phenylalanine at position 331 (F331) of human PPOX, affecting the binding to the herbicide (i.e., de-stabilizing conformation);

or any combination thereof. Each possibility is a separate embodiment.

In some embodiments, the amino acid sequence of a fungal-isolated PPO comprises one or more of the sequences denoted by any one of SEQ ID NOs: 2, 94, 96-98, or any combination thereof. Each possibility is a separate embodiment.

In some embodiments, the amino acid sequence of a fungal-isolated PPO comprises one or more of SEQ ID NOs: 2, 94, 97-98, or any combination thereof. Each possibility is a separate embodiment.

In some embodiments, the amino acid sequence of a fungal-isolated PPO comprises SEQ ID NOs: 2 and/or 98. Each possibility is a separate embodiment.

In some embodiments, the amino acid sequence of a fungal-isolated PPO comprises SEQ ID NOs: 96. Each possibility is a separate embodiment.

Reference is now made to Table 3 summarizing the modes/mechanism of acquiring PPO-herbicide tolerance in fungal-isolated PPOs.

In some embodiments, the fungal-derived PPO is isolated from a fungal species of the clade leotiomyceta.

In some embodiments, the fungal-derived PPO is isolated from a fungal species selected from *Aspergillus* sp., *Penicillium* sp., *Trichoderma* sp., *Rhodotorula* sp., *Hesseltinella* sp.

In some embodiments, the exogenous fungal-derived PPO has less than 40% similarity to an amino acid sequence of an endogenous plant PPO enzyme.

In some embodiments, the exogenous fungal-derived PPO enzyme further comprises a plant chloroplast transit peptide.

In some embodiments, the plant is selected from the group consisting of maize, wheat, rice, barley, soybean, cowpea, chickpea, cotton, sorghum, beans, rapeseed/canola, alfalfa, flax, sunflower, safflower, millet, rye, sugarcane, sugar beet, cocoa, tea, *Brassica*, coffee, sweet potato, flax, peanut, clover; lettuce, tomato, cucurbits, cassava, potato, carrot, radish, pea, lentils, cabbage, cauliflower, broccoli, brussels sprouts, peppers, pineapple, citrus, apples, pears, peaches, apricots, walnuts, avocado, banana, palm, *eucalyptus*, poplar, pine, coconut, orchids, *petunia*, carnations, roses, switchgrass, prairie grasses, indian grasses, big bluestem grass, camelina, and any combination thereof. Each possibility is a separate embodiment.

In some embodiments, the plant is selected from the group consisting of maize, wheat, rice, soybean, cowpea, chickpea, cotton, sorghum, rapeseed/canola, alfalfa, sunflower, sugarcane, sugar beet, camelina, or any combination thereof. Each possibility is a separate embodiment.

In some embodiments, the one or more PPO inhibitors is selected from the group consisting of herbicide families Phenylpyrazoles, Pyrimidindiones, Oxazolidinedione, Diphenylethers, Oxadiazoles, N-phenylphthalimides, Triazinone, Thiadiazoles, Triazolinones, and Triazolopyridinones, or any combination thereof. Each possibility is a separate embodiment.

In some embodiments, the plant is a broad leaf plant.

In some embodiments, the comparing of the 3D structure/folding of fungal-derived PPO with a crystal structure of human PPO bound with acifluorfen, comprises comparing a simulated structure of the folding of fungal-derived PPO or a crystal structure showing the folding fungal-derived PPO.

According to another aspect, there is provided a transgenic plant expressing an exogenous fungal-derived Protoporphyrinogen Oxidase (PPO) enzyme conferring resistance or tolerance to at least one PPO-inhibitor herbicide, wherein the fungal-derived PPO enzyme comprises an amino acid sequence having at least 80% similarity to fungal-isolated PPO sequences as set forth in any one of SEQ ID NOs: 1-7 and SEQ ID NOs: 86, 88-89, 91-99, or any combination thereof. Each possibility is a separate embodiment.

In some embodiments, the fungal-derived PPO enzyme comprises an amino acid sequence having at least 90% similarity to fungal-isolated PPO sequence as set forth in any one of SEQ ID NOs: 1-7 and SEQ ID NOs: 86, 88-89, 91-99, or any combination thereof.

In some embodiments, the fungal-derived Protoporphyrinogen Oxidase (PPO) enzyme comprises amino acid sequence having at least 80% similarity, at least 81%, at least 82%, at least 83%, at least 84%, at least 85%, at least 86%, at least 87%, at least 88%, at least 88%, at least 89%, at least 90%, at least 91%, at least 92%, at least 93%, at least 94%, at least 95%, at least 96%, at least 97%, at least 98%, at least 99%, at least 99.9%, or more, to an amino acid sequence of a fungal-isolated PPO. Each possibility is a separate embodiment.

In some embodiments, the amino acid sequence of a fungal-isolated PPO comprises any one of SEQ ID NOs: 1-7 and SEQ ID NOs: 86, 88-89, 91-99, or any combination thereof. Each possibility is a separate embodiment.

In some embodiments, the fungal-derived PPO enzyme comprises a pocket opening size of not more than 9.5 Angstrom.

In some embodiments, the exogenous fungal-derived PPO comprises a first arginine at a position structurally corresponding to arginine at position 97 in human PPOX (human Arg97) and/or a second arginine at a position structurally corresponding to arginine at position 62 in human PPOX (human Arg62), wherein the first and/or second arginine of the fungal-derived PPO have a different geometrical orientation, compared to the human Arg62 and/or human Arg97 geometrical orientation, and wherein said position of the fungal-derived PPO structurally corresponding to Arg62 and/or Arg97 and the different geometrical orientation thereof are determined by comparing a simulated 3D structure/folding of fungal-derived PPO with a crystal structure of human PPOX bound with acifluorfen provided by PDB identifier: 4IVO, and wherein the simulated 3D structure/folding of fungal-derived PPO is structurally aligned to the crystal structure of human PPO and is superimposed with acifluorfen.

In some embodiments, the exogenous fungal-derived PPO comprises a phenylalanine at a position 404 (F404) which structurally corresponds to valine at position 347 (V347) of human PPOX, and wherein said corresponding phenylalanine position of the fungal-derived PPO is determined by comparing a simulated 3D structure/folding of fungal-derived PPO with a crystal structure of human PPO bound with acifluorfen provided by PDB identifier: 4IVO, and wherein the simulated 3D structure/folding of fungal-derived PPO is structurally aligned to the crystal structure of human PPO and is superimposed with acifluorfen.

In some embodiments, the exogenous fungal-derived PPO comprises a phenylalanine at a position 383 (F383) which structurally corresponds to a phenylalanine at position 331 (F331) of human PPOX, and wherein said corresponding phenylalanine position of the fungal-derived PPO is determined by comparing a simulated 3D structure/folding of fungal-derived PPO with a crystal structure of human PPO bound with acifluorfen provided by PDB identifier: 4IVO, and wherein the simulated 3D structure/folding of fungal-derived PPO is structurally aligned to the crystal structure of human PPO and is superimposed with acifluorfen.

In some embodiments, the fungal-derived PPO comprises an amino acid sequence having less than 40% similarity to an amino acid sequence of an endogenous plant PPO enzyme.

In some embodiments, the fungal-derived PPO comprises an amino acid sequence having less than about 55% similarity, less than about 50% similarity, less than about 45% similarity, less than about 40% similarity, less than about 35% similarity, less than about 30% similarity, less than about 25% similarity, less than about 20% similarity, to an amino acid sequence of an endogenous plant PPO enzyme. Each possibility is a separate embodiment.

In some embodiments, the fungal-derived PPO enzyme further comprises a plant chloroplast transit peptide.

According to some embodiments, the fungal-derived PPO is isolated from a fungal specie selected from Aspergillus sp., Fusarium sp., Rhizopus sp., Penicillium sp., Trichoderma sp., Rhodotorula sp., Hesseltinella sp., Spizellomyces sp. Rhizophagus sp., Alternariav sp., and Cladosporium sp., or any combination thereof. Each possibility is a separate embodiment.

In some embodiments, the fungal-derived PPO enzyme is isolated from a fungal species selected from the group consisting of Aspergillus, Fusarium, Rhizopus, Penicillium, and Trichoderma., or any combination thereof. Each possibility is a separate embodiment.

In some embodiments, the fungal-derived PPO is isolated from a fungal species selected from Aspergillus sp., Penicillium sp., Trichoderma sp., Rhodotorula sp., Hesseltinella sp., or any combination thereof. Each possibility is a separate embodiment.

In some embodiments, the fungal-derived PPO enzyme is isolated from a fungal species of the clade leotiomyceta.

In some embodiments, the plant is selected from the group consisting of maize, wheat, rice, barley, soybean, cowpea, chickpea, cotton, sorghum, beans, rapeseed/canola, alfalfa, flax, sunflower, safflower, millet, rye, sugarcane, sugar beet, cocoa, tea, Brassica, coffee, sweet potato, flax, peanut, clover; lettuce, tomato, cucurbits, cassava, potato, carrot, radish, pea, lentils, cabbage, cauliflower, broccoli, brussels sprouts, peppers, pineapple, citrus, apples, pears, peaches, apricots, walnuts, avocado, banana, palm, eucalyptus, poplar, pine, coconut, orchids, petunia, carnations, roses, switchgrass, prairie grasses, indian grasses, big bluestem grass, camelina, and any combination thereof. Each possibility is a separate embodiment.

In some embodiments, the plant is selected from the group consisting of maize, wheat, rice, soybean, cowpea, chickpea, cotton, sorghum, rapeseed/canola, alfalfa, sunflower, sugarcane, sugar beet, camelina, or any combination thereof. Each possibility is a separate embodiment.

In some embodiments, the one or more PPO inhibitors is selected from the group consisting of herbicide families Phenylpyrazoles, Pyrimidindiones, Oxazolidinedione, Diphenylethers, Oxadiazoles, N-phenylphthalimides, Triazinone, Thiadiazoles, Triazolinones, and Triazolopyridinones, or any combination thereof.

In some embodiments, the plant is a broad leaf plant.

In some embodiments, the plant is a cereal plant.

According to some aspects, there is provided a seed of the transgenic plant, according to any one of the preceding embodiments.

According to some aspects, there is provided a product derived from the transgenic plant of any one of the preceding embodiments.

According to some aspects, there is provided a method of controlling weeds growth where crop plants are growing, using at least one PPO inhibitor herbicide, wherein the crop plants comprise the transgenic plant according to any one of the preceding embodiments, the method comprising applying a weed-controlling amount of the one or more PPO inhibitor herbicide.

In some embodiments, the one or more PPO inhibitors are selected from the group consisting of herbicides families Phenylpyrazoles, Pyrimidindiones, Oxazolidinedione, Diphenylethers, Oxadiazoles, N-phenylphthalimides, Triazinone, Thiadiazoles, Triazolinones, and Triazolopyridinones, or any combination thereof.

According to some aspects, there is provided method for conferring resistance or tolerance to one or more PPO inhibitor herbicide in a crop plant, the method comprising genetically modifying the plant to express an exogenous fungal-derived PPO enzyme, wherein the fungal-derived PPO enzyme comprises an amino acid sequence having at least 80% similarity to a fungal-isolated PPO sequence as set forth in any one of SEQ ID NOs: 1-7 or SEQ ID NOs: 86, 88-89, 91-99, or any combination thereof.

Sequences:

According to some embodiments, the native fungal-isolated PPO polypeptides have the amino acid sequence set forth in any one of SEQ ID NO: 1-7 and SEQ ID NO: 86-100:

```
SEQ ID NO: 1
PPO from Aspergillus sp. Protein.
>SEQ ID NO: 1
MRLPCASSRVFRQVRAPLALLSRGQRHAVHTKQFDAAVIGGGITGLTAAYQLSRDPSCSKVTLYEKSPHLG
GWLSSEQIPVPGGHVVFEYGPRTLRTSSPSCLPMMDLIMNLDLLDDVLICDKKSPAAQNRYIYYPDHLVRL
PFPPTEGLLKTAWTLLMEPLFETFLYSAIFEKPKRAENTHILSRDESVADFVSRRESPKISENLASAVMAG
IFAGDVNRLSAEMAIGYVRELEKRYGSIVDGMMTQRASEMRAMPMDELLALESVAVPSHSDDRYWKSLRAV
VSDASVLTLKNGLGQLTDAMAAQLRSSRNVEVVTGTEVTSLSQNPKTQDLTIGFGKNESKTHNRVIATHAP
SSLARQIQNTKVGVVPSDTIRDLGQNNYAVTVMVVNLYYEDPDLVPVEGFGYLLPSSVPFEQNPERALGVI
FGSQSSEGQDTAPGTKLTVMMGGHLWDGWSESDYPDPDKAIEMAQALLHRHLGIKTAPSVARARLLRDAIP
QYTVGHLSRMKELSHSVRSDFHKRLTLAGAWYGTVGIGVVDCIRQGYLASSYGVGSKKLGPGNSRRPWTKH
DFHNWELEGGIATSPVRLDNVHVTERQHY
```

-continued

SEQ ID NO: 2
PPO from *Aspergillus* sp. Protein.
>SEQ ID NO: 2
MRLPCASSRAFRQVRAPLALLHRGQRHAVHTKQFDAAVIGGGITGLTAAYQLSRDPSCSKVTLYEKSSHLG
GWLSSEQIPVPGGHVVFEYGPRTLRTSSPSCLPMMDLIMNLDLLDDVLICDKKSPAAQNRYIYYPDHLVRL
PFPPTEGLLKTAWTLLMEPLFETFLYSAIFEKPKRAENTHILSRDESVADFVSRRFSPKISENLASAVMAG
IFAGDVNRLSAEMAIGYVRELEKRYGSIVDGMMTQRASEMRAMPMDELLALESVAVPSHSDDRYWKSLRAV
VTDASVLTLKNGLGQLTDAMAAQLRSSRNVEVVTGTEVTSLSQNPKTQDLTIGFGKNESRTHNRVIATHAP
SSLARQIQNTKVGVVPSDTIRDLGQNNYAVTVMVVNLYYEDPDLVPVEGFGYLLPSSVPFEQNPERALGVI
FGSQSSEGQDTAPGTKLTVIMGGHLWDGWSESDYPDPDKAIEMAQALLHRHLGIKTAPSVARARLLRDAIP
QYTVGHLSRMKELSHSVRSDFHKRLTLAGAWYGTVGIGVVDCIRQGYLASSYGVGSKKLGPGNSRRPWTKH
DFHNWELEGGIATSPVRFDNVHVTERQHY SEQ ID NO: 3
PPO from *Fusarium* sp. Protein.
>SEQ ID NO: 3
MSRRRAESTAVALLSSPAKSHLQPPLRRLDGIRSLSTSSALARRRPIVACNYTQSFNNGRTFVSQAKDANI
AVLGGGLTGLTAAYYLAKKLPSTAKITLYESSDRLGGWIKTDRVPVDIEGKSGTLSFERGARSLSSLVGNT
FRFDDLVLYDLALDLGLAINSPSQQPRYIYYPDHLVPTPPNISIFDMLREPLYLEIIGASLGLGINSLRKR
TLPSKDYSVSEWLYAVSNSRKGIGNLASAMMHGIYGGDIHKLSARCVLDRLYWGWYLPNPGLSVRPMPVAE
QALLETLGQDKQIQKMALEPRSALVDFGDKGMESLPQALSAALREQPNITIKTGEAVQDVVYNKANQQVHI
TSSNAKDNSKHNSKVYDKVISTLSAQDIALLAGNKLPSLSTAHSVSVMTVNIWFPQENLKPPGFGYLIPNS
VAPELNPEHALGVFFDSDVQTRSKDEPAGTKLFVLMGGHYYDRPDVTPPTEEEAIIQARNLLERHLGIPRD
APAYATANFARECIPQHYVGHQDRLKAAHTELTRNFGGRLAVAGGSFTRIGAVASLRAGYDAATAAKKGLE
ATGLEYLNDIQQFSVVATSHIPVRHFK SEQ ID NO: 4
PPO from *Fusarium* sp. Protein.
>SEQ ID NO: 4
MSRRRAESTAVALLSSPAKSHLQPPLRRLDGIRSLSTSSALARRRPIVACNYTQSFNNGRTFVSQAKDANI
AVLGGGLTGLTAAYYLAKKLPSTAKITLYESSDRLGGWIKTDRVPVDIEGKSGTLSFERGARSLSSLVGNT
FRFDDLVLYDLALDLGLAINSPSQQPRYIYYPDHLVPTPPNISIFDMLREPLYLEIIGASLGLGINSLRKR
TLPSKDYSVSEWLYAVSNSRKGIGNLASAMMHGIYGGDIHKLSARCVLDRLYWGWYLPNPGLSVRPMPVAE
QALLETLGQDKQIQKMALEPRSALVDFGDKGMESLPQALSAALREQPNITIKTGEAVQDVVYNKANQQVHI
TSSNAKDNSKHNSKVYDKVISTLSAQDIALLAGNKLPSLSTAHSVSVMTVNIWFPQENLKPPGFGYLIPNS
VAPELNPEHALGVFFDSDVQTRSKDEPAGTKLFVLMGGHYYDRPDVTPPTEEEAIIQARNLPERHLGIPRD
APAYATANFARECIPQHYVGHQDRLKAAHTELTRNFGGRLAVAGGSFTRIGAVASLRAGYDAATAAKKGLE
ATGLEYLNDIQQFSVVATSHIPVRHFK SEQ ID NO: 5
PPO from *Fusarium* sp. Protein.
>SEQ ID NO: 5
MSRRRAESTAVALLSSPAKSHLQPPLRRLDGIRSLSTSSALARRRPIVACNYTQSFNNGRTFVSQAKDANI
AVLGGGLTGLTAAYYLAKKLPSTAKITLYESSDRLGGWIKTDRVPVDIEGKSGTLSFERGARSLSSLVGNT
FRFDDLVLYDLALDLGLAINSPSQQPRYIYYPDHLVPTPPNISIFDMLREPLYLEIIGASLGLGINSVRKR
TLPSKDYSVSEWLYAVSNSRKGIGNLASAMMHGIYGGDIHKLSARCVLDRLYWGWYLPNPGLSVRPMPVAE
QALLETLGQDKQIQKMALEPRSALVDFGDKGMESLPQALSAALREQPNITIKTGEAVQDVVYNKANQQVHI
TSSNAKDNSKHNSKVYDKVISTLSAQDIALLAGNKLPSLSTAHSVSVMTVNIWFPQENLKPPGFGYLIPNS
VAPELNPEHALGVFFDSDVQTRSKDEPAGTKLFVLMGGHYYDRPDVTPPTEEEAIIQARNLLERHLGIPRD
APAYATANFARECIPQHYVGHQDRLKAAHTELTRNFGGRLAVAGGSFTRIGAVASLRAGYDAATAAKKGLE
ATGLEYLNDIQQFSVVATSQIPVRHFK SEQ ID NO: 6
PPO from *Rhizopus* sp. Protein.
>SEQ ID NO: 6
MSSVAILGGGISGLSAAYYLARMAPPTTKITLIEGKKRLGGWIESRRVTPGHYDNIHQLPKNNSKENTILF
EAGPRTLRPEGSNGAILLEMIRHLELNNENLMSVSKSHPSARHRYIYYKDKINTLPSDLQSFLLNKPPVLK
SVPLAALLEPLKPSRFDKDGIAKDGIQDESIYSFMTRRFNEHTAIHLMGAVIHGIYAGDIKSLSLQSTLRS
LYEAERIYGSAVLGMMKGASQVTTSVRERGMAARSRKEDPEWFGRMEKMSVIGFKSGMDTLPHQITSWLEQ
CPNVEVITDDPAEHIEIAHENKIKTQKGKTVHADHIISTLPSPVLERLVQHQPVLPHLSYNPSADVAVVNL
AYSPDEMKLQYDGFGFLTPHRDTPYGNPLPGTLGVVFDSNALPIESERAVKLTAMIGGSDWKDAFGNVPID
ELEPKVALDYTRKAVGTFLDIHAEPRYSMVNLQKQCIPQYLVGHQDRMLSLHHAIKKNYGHALSVSGASYL
GVSVPDCIKNSRMLVEELLVSGALGSRQKVVTGLGKLEEQPTVDEMRDNARLSRGNTSVIMKS SEQ ID NO: 7
PPO from *Penicillium* sp. Protein.
>SEQ ID NO: 7
MRLLTASKGLRSPQKPLISAIRCQHRAYNAAVIGGGITGLTAAWQLIQDRECSSVTIYEKSRRLGGWLQSE
TIPVEGGEVVFEYGPRTLRSAMPASLPLLYLVSNLGLEDELITTSKRSPAALNRYIYYPDHLVRLPSPDPD
LSLMENARNIFRTITTEPLFEGFITGLLSEPNKPARPQEEWAIDESLAEFITRRFNRKIADNLVSAVMHGI
YAGNIDEMSAQAIMGPLRNLEDGGILFGLLIKSIMGKKTRSMDDFLAVDAVYKTPETMQRLDEINRVVKTA
STFTFKRGTQQLVEGLTRALRTSEKVRLVMDADILALDPPANRGHKLKIYTGIRGEESFDHVISAISAPAM
ARILDPQGQVKIDCDPEDEYRALWNSKKARHPKPNIGTVSGLHFFRHATTVMVVNLYYKTPNLLPVDGFGY
LIPRSIPYEQNPECGLGVIFASASSSGESPVAPYPKVSQDSAPGTKITIMFGGHYWDGWKKQDYPDHKTAV
RMAKDMLERHLGITEPPALVRTRLQENAIPKYTPLHIHQIYALSRWAKEEYHNRLVLVGNSFSGVGVGDCV
RQGIMAATHGVGRHKLTATPRLKSKDWCPWKEYNYQHWDLKGGVTTAPVRLFESDI -continued SEQ ID NO: 86
PPO from *Trichoderma* sp. Protein.
>SEQ ID NO: 86
MRLPCASSRVFRQVRAPLALLRRGQRHALHTKQFDAAVIGGGITGLTAAYQLSRDPSCSKVTLYEKSSHLG
GWLSSEQIPVRGGHVVFEYGPRTLRTSAPSCLPMMDLIMNLDLLDDVLICDKKSPAAQNRYIYYPDHLVRL
PFPPPTEGLLKTAWTLLMEPLFETFLQSALFEKPKRAVDGDVLSRDESVADFVSRRFSPKMSENLASAVMAG
IFAGDVNRLSADMAIGYVRELEKRYGSIVDGMMTQRASELRAMPMDEFLALESVAVPSHKDDRYWKSLRAV
VSDASVLTLKNGLGQLTDAMAAQLRSSNNVEVVSGTEVTSLSQNPETRDLTIGFGKNESKTHNRVIATHAP
SSLARQLENTKVGVAPSDTLRALGQNNYAVTVMVVNLYYEDPDLVPVQGFGYLLPSSIPFEENPERALGVI
FGSQSSEGQDTAPGTKLTVMMGGHLWDGWSESDYPDPDKAVEMAQALLHRHLGIKTAPSVARARLLRDAIP
QYTVGHLSRMKELSQSVRGDFHKRLTLAGAWYGTVGIGVVDCIRQGYIASSFGVGSKKLGPGGGRRPWTKH
DFHNWELEGGICTSPVRFDNVHITERQH SEQ ID NO: 87
PPO from *Aspergillus* sp. Protein.
>SEQ ID NO: 87
MRLPCVPSCALRGVRTPLAFARIGQRYSSTYDAAVIGGGITGLTAAYRLSQDPNCSKITLYEKAPRVGGWL
LSEKIPVEGGNVVFEYGPRTLRTAVPSCLPLLDLLVELGLHDDVLLTSSSSPAARNRYIYYPDHLVRMPAP
DPNAGPIENITNPLFAMLREPVFEGLIASALLEPVRAPPDHKTENSDESVADFVSRRLCPEVADNLVSALF
HGIYAGDISRLSAQTLLGTFRDLENDDRRVIGGYINSLMSDVKLMAMDDLLALESVAHEKPGMYWKSLRTL
VNKTSVLTLKDGLSQLSDALVDALKKSKKVDVLANTDVKSITQNPMTDDLIVGSGQDRSRIHNRVIATIPA
PELANKLATTTVKDQKVPQSTIRNLQEHNYAVTVMVVNLYFPNPDLLPVSGFGYLIPRSIPYEQNPERALG
VIFGSDSSVGQDTAPGTKLTVMMGGHWWDGWKESDYPDHDTAVAMSRALLHRHLGITDAPTLTSSRLQRNA
IPQYTVGHLSRMRELSRSTRHELNNRLTLAGSWYNGVGVTDCIRQGYLAASFGVGARKLGPGDGDRPWRRF
DYEKWELEGGIVTSPVRWAEVYRTERKHF SEQ ID NO: 88
PPO from *Aspergillus* sp. Protein.
>SEQ ID NO: 88
MRLPHASSHALKGSRLSLALARNGQRRSLHTPTYDAVVGGGITGLTTAYRLSRDPKCSKITLYEKSKNVG
GWLQSEKIPFKDGHVVFEYGPRTLRTALPSCLPLLDLLEELDLLGEVLVTSKTSAAALNRYIYYPDHLARV
PAPDPARGALGNALSLMWSLFREPVFKSIFLGIYNDIQSPAPQKLKADESVGDFISRRLSPELADNLVSSV
FHGIYAGDIYQLSAEALLGQHREPEGGVPSIMLRLINEARMNHTPELLDDQLAMELILEEKSRSYLNALAV
LVRQASVLTLRNGLGQLTDALLAALAKSKKVDILPEAEVTAISRNQNSSNITISHGQDEHRMHNRVVSTIP
APHLAKALRQGGGEDKKLPHNTIQALEEHNYAVTVMVVNLFYEKEDLLPVKGFGYLIPRSIPFEQNPERGL
GVIFGSETSAGQDTVPGTKLTVMLGGHLWDGWTESDYPDHDTAVKMARTLLERHLGITDAPAISRSRLHRN
AIPQYTVGHPARMDRISESARADFSNRLSLAGSWYGGIGVVDCIRHAYLTAAYGVSAQKLRSGGQDRPWKL
FNYTQWELEGGIVKSPVRLVWRRPDSKN SEQ ID NO: 89
PPO from *Fusarium* sp. Protein.
>SEQ ID NO: 89
MSHSRAESTAVALLSSAAHSTTKPHLRVPLCRLNGFRNLSTCSASALTRRRPIIACKHTQSSRDGRRYVSQ
AKDANIAVIGGGLTGLSAAYYLAKKLPSTTKITLYEANDRLGGWIKTDRVPVDIEGKKGIVSFERGSRSLT
SLVGNTFRFDDLVLYDLTLDLGLSLNFPPARPRYVYYPDHLVATPPNISIFDILREPLYLESFGAGLGLMI
NQLRKRQLPAEDESVADWLYKVINSRKGIGNLASAMMHGIYGGDINKLSARSVLDRIYWGWYMPNPGLHAR
PMPLPEQLILETLGQDRQIQKLALEPKSTLIDFGDKGMESLPQAIGAALRDQPNVTIMTGEAVNDIQYDEA
KKQVQINSFNTQNEEKSNSQAYDKIVSTLSAQHIARLAGDKVQSLSAAHSVSVMTVNIWFPQENLKPPGFG
YLIPDSVEPELNPEHALGVFFDSDVGTRSKDEPAGTKLFVLMGGHYYDRPGVTPPTEDEAIVQARNLLERH
LGIPRDAPAYATANFAKECIPQHNVGHQDLLRNAHAELKQNFGGRLAVAGGSFHRIGTIASLRSGYDAAVA
TKNGLEATGLEYLETITEFAVVPTDMIPVRLFK SEQ ID NO: 90
PPO from *Fusarium* sp. Protein.
>SEQ ID NO: 90
MSRRRAESTAVALLGSPAKPHLPLPLRRLDAIRSLSTSSALTRRRPIVARNYTQFFNNGRTFVSQAKDANI
AVLGGGLTGLTAAYYLAKKLPSTAKITLYESSDRLGGWIKTDRVPVDVEGKSGTVSFERGARSLSSLAGNT
FRFDDLVLYDLALDLGLVVNSPRQQPRYIYYPDHLVPMPPNVSIFDIFREPLYLESIGASLGLGINSLRKR
TLPSKDYSVSEWLYAVSNSRKGVGTLASAMMHGIYGGDIDKLSARSVLDRVYWGWYLPNPGLSARPMPVAE
QTLLETLGQDKQIQKMALEPRSALVDFGDKGMESLPQALSTALREQPNVTIKTGEAVQDVVHNKTNQQVHV
TSSNAKNKSEHNSKVYDKVISTLSAQDIARLTGDKLPSLSTAHSVSVMTVNIWFPRENLKPPGFGYLIPNS
VAPELNPEHALGVFFDSDVQTRSKDEPAGTKLFVLMGGHYYDRPDVTPPTEEEAILQARNLLERHLGIPRD
APAYATANFARECIPQHYVGHQDRLRAAHTELTHNFGGRLAVAGGSFTRIGAIASLRAGYDAATAAKEGLE
ATGLEYLNDIQQFSVVATSHIPVRHFK SEQ ID NO: 91
PPO from *Rhizopus* sp. Protein.
>SEQ ID NO: 91
MSSVAILGGGISGLSAAYYLARMAPPTTKITLIEGKKRLGGWIESRRVTPGHYDNIHQLPKNNSKENTILF
EAGPRTLRPEGSNGAILLEMIRHLELNNENLMSVSKSHPSARHRYIYYKDKINTLPSDLQSFLLNKPPVLK
SVPLAALLEPLKPSRFDKDGIAKDGIEDESIYSFMTRRFNEHTAIHLMGAVIHGIYAGDIKSLSLQSTLRS
LYEAERIYGSAVLGMMKGASQVTTSVRERGMAARSRKEDPEWFGRMEKMSVIGFKSGMDTLPHQITSWLEQ
CPNVEVITDDPAEHIEIAHENKIKTQKGKTVHADHIISTLPSPVLERLVQHQPVLPHLSYNPSADVAVVNL
AYSPDEMKLQYDGFGFLTPHRDTPYGNPLPGTLGVVFDSNALPIESERAVKLTAMIGGSDWKDAFGNVPID
ELEPKVALDYTRKAVGTFLDIHAEPRYSMVNLQKQCIPQYLVGHQDRMLSLHHAIKKNYGHALSVSGASYL
GVSVPDCIKNSRMLVEELLVSGALGSRQKVVTGLGKLEEQPTVDEMRDNARLSRGNTSVIMKS SEQ ID NO: 92
PPO from *Rhizopus* sp. Protein.
>SEQ ID NO: 92
MSSIAVLGGGISGLSAAYYLARLAPASTKIVLIEGKDRLGGWIHSRRVAPGKYSRDKAPQLSNEKDSILFE
AGPRSLRPEGPNGAILLEMIQNLDLNNEGLLSVPKTDPSVKNRYIYYDGEINTLPSGPISMLLKKPPVFKS
VILAGALEPLRSSRFKNGKPKDGIEDESMYNFMKRRFNEHTAINLMGAVAHGVYAGDVKQLSIQSTLRMLY
EAEKNYGSVIVGMMRGAANTSTMRERGMAVRSRDKDPEWFGRMEKMSVLGFKDGMETLPDRLCSWLEQRPN
VEIIRNDPVESIEPLENGKESKIKTKSNEFFADHVLSTIPSFTLEKLIKPNSLPNLSHNPASDVAVVNFAY
SPEVKLGYDGFGFLTPHRDTKYRVPVPGTLGVIFDSNAMPGQETEQPEVVKVTAMMGGADWKDAFGKATID
ELDPEVAYKYARKGMSVFLNLHDEPTHAMVNLQKQCIPQYVVGHEGRMRELHHALKQNYGHLMSLTGASYM
GVSVPDCIKNSRMLVEELLVSGALGSRDKVVTGLGRTVESNSKELQDGARISKGTVDVIMKS SEQ ID NO: 93
PPO from *Rhizopus* sp. Protein.
>SEQ ID NO: 93
MSAVILGGGISGLSAAYYLARMAPSTTKITLIEGKNRLGGWIESRRVTAGHYDNIHCLPKENQQNTVLFEA
GPRTLRPEGTNGAILLEMIRHLDLNNDDLLSIPKSHPSAKNRYIYYQDKINKLPSDFGSFLRQRPPVLKSV
PLAGLLEPLRTSRFENGLPKNGEEDESIYSFISRRFNEHTATHLMGAVIHGIYAGDVRALSLQSTLNSLYE
AERTYGSAVLGMLKGVSQATQTMRERGMAARSRKDDPDWFGRMEKMSVIGFKTGMDSLPDKITAWLKQRPN
VEIITHDSVQHIGEGKIKTEHREIEADHIISTLPSSVLHSLLSRPLPHLMHNPAVDVAVVNLAYPSDIKLD
YDGFGFLTPHRDSKYPNPVPGTLGVVFDSNSLPIDSEHATKLTVMMGGSDWKDAFGDVSLDQLDPQVALQR
ARQAVSTFLGIHAEPHASMVHLQKQCIPQYLVGHRQRMRSLHHAIKQDYGHSLSVSGASYLGVSVPDCIKN
SRMLVEELLVSGALGSRQKIVTGLGRLEQEMTVEEMRDNARVSKSNTSVIIKS SEQ ID NO: 94
PPO from *Penicillium* sp. Protein.
>SEQ ID NO: 94
MRLLTASKGLRSPQKPLISAIRCQHRSYNAAVIGGGITGLTAAWQLIQDRECSSVTIYEKSRRLGGWLQSE
TIPVEGGEVVFEYGPRTLRSAMPASLPLLYLVSNLGLEDELITTSKRSPAALNRYIYYPDHLVRLPTPDPD
LSLMENARNIFRTITTEPLFEGFITGLLSEPNKPARPQEEWAIDESLAEFITRRFNRKIADNLVSAVMHGI
YADNIDEMSAQAIMGPLRNLEDGGILFGLLIKSIMGKKTRSMDDFLAVDAVYKTPETMQRLDEINRVVKTA
STFTFKRGTQQLVEGLTRALRASEKVRLVMDADILALDPPANRGHKLKIYTGIRGEESFDHVISAISAPAM
ARILDPQGQVKIDCDPEDEYRALWNSKKARHPKPNIGTVSGLHFFRHATTVMVVNLYYKTPNLLPVDGFGY
LIPRSIPYEQNPECGLGVIFASASSSGESPVAPYPKVSQDSAPGTKITIMFGGHYWDGWKKQDYPDHKTAV
RMAKDMLERHLGITEPPALVRTRLQENAIPKYKPPHIHQIYALSRWAKEEYHNRLVLVGNSFSGVGVGDCV
RQGIMAATHGVGRHKLTATPRLESKDWCPWKEYNYQHWDLKGGVPTAPVRLFESDI SEQ ID NO: 95
PPO from *Penicillium* sp. Protein.
>SEQ ID NO: 95
MRLPCVSRALRPRPRQLTHLLNGQKCTYSAVVLGGGITGLTAAWQLAQDPICKSITLFEKTDRLGGWIDSE
TVPVDGGNVVFEYGPRTLRSSLPGSLPLLYLATNLGLYKDLIVTPNTSPAAQNRYIYYPDRLVRMPAPKPE
LSFAENFDSFVNTMMEPLFNKFLSGIVKDVFTPPRHPTEWAEDESVADFIGRRFGPKVADNIVSAVYHGIY
AGDIDQLSAQTLLGSVRNLEGGIGGIGGLVSGGVTASLISRSLSKTKTRNMEDFMAIDAISAGPELVRRQH
DLEVLAAGASTFTFKRGVGQLTEALVASLKASGKVRFQMNKEITGLRALARAPAIAMEFWSDRHSQVKTFE
YDYVISTIPPVALAKTMRKTEQLEAKLYPVGLTPLLLRRQDYAVTVLVVNLYYPNPNLLPVEDGFGYLIPR
SIPYEQNPECGLGVIFASSSSVGNGTDPSSSEVNQDSAPGTKITVMLGGHYWDGFEEYPDHDTAVKMARDM
LKRHMNITDTPTVTRSRLQKDAIPQYTVGHLDRMYKLSDTVRKDYQKRLILAGNWYNGVSVGDCVKQGILS
ATYGIGRNRLNYEPSPWRPWTSFDYKRWKLEGGIVMSPVRLVDSKI SEQ ID NO: 96
PPO from *Trichoderma* sp. Protein.
>SEQ ID NO: 96
MSLKRADGAAMAFLRLSSAVCGRRRIPAGGLPADANVAVLGGGLTGLTTAYYLAKWLPPTAKITLLEASD
RLGGWIKTDRVPVKVGGVEGVVSFERGPRSLSSLNKSTWRFDDLVLWDLALDLGLRVVSPPDKPRYIYYP
DHLVPLPPHTSLAAFASEPLVLESLWAGFGYVLRRLFSRKAGVPVQDLSIADWIQHITGSRAVAENLASA
MVHGIYGGDIYTLSARSVLDRFYWVHYLPALGPDVRHMALSEQVFMEAMGQDPLIRKLAQQPRGALLNFG
EAGMETLPIALADALNGQANVEVKLGAKVTGLEYESETEMMKITTTGQDDSPAEKYHKVISTLPSQHLAR
ITDTLPSLASSHAVSIMTVNIWYPQTNLKPPGFGYLIPLSVPAEQNPERALGVFFDSDVGVRGPDEPAGT
KLFVLMGGHYYDKKQPGASVRVPSEEEAIEQAKRVLERHLGIPQSTPCFAMARLASECIPQYVCGHQDTM
AAADEDLRDSFDGRLAVAGGSYTKIGAMGALRNGYDIANTVVREDWLTTGLEQLEFPTQFCGVPTERIPV
RRFSRR SEQ ID NO: 97
PPO from *Rhodotorula* sp. Protein.
>SEQ ID NO: 97
MQSYSGNALARQSVPIKPIRRRTPRLNLIRSLPSPRFFVTSPSSSQRHDHPYHTLAILGGGLSGLSTAHYF
LRTLSPSLRDQTRIVVLEKEERVGGWCRAVRIQNGRRLGENEKPEGTEDLLVFETGPRSVRPVGLLGWLTI
EMAHELGLTPSIVTVPKSAPSARNRFIYTGHRSSTSISPILKAALPTIPSALLEPFRPRSPLHDDPSGLAD
ESVDSFIARRFGRRLADELASAGIHGIYAGDTRRLSVRAVLPALWELEKEWGSVVIGALFGSFARRRGWKK
NSPWRMRQQAETEEMERVKERIRAKGGEALVEDMEKASVWGVKGGLQVVTETLREKLEAEGVEFWMGEKGK
VEHVEKVDGGWQIRTSSGALDASQLVTTIPQLLPSSLAPPALPATTVSVVNLAFEKPAPGSPPLHPAGFGY
LIPRTVPSSLNPHRALGVIFDSDVMPDVDSSSSLGLTKLSLLLGGSYWLDRHPPPQPSHDDLVNAALETLR
LHFPDRPIPKPVHAFTHTHVNCIPQVPPGEMPSFRAFGDRLREAGNVAVVGGGFAAVGVNGCVKAAWEVGS
AMAQAVNAQAGGKEGEGEEKVREAVARTVKTGTEMWEL -continued

```
SEQ ID NO: 98
PPO from Hesseltinella sp. Protein.
>SEQ ID NO: 98
MPRSIVVLGGGISGLSAAYYLSRLVPQAHIRLIESNKRAGGFIKTQQVNDHLIFEAGPRTLRPHGTSGTVL
LDMIKDLDLSPLLVNIPKSHPSAQHRYIEYHGQINQLPSGLADMLLHSPPIMDSVITAGMREPFLARASTT
KDESLYNFMERRFNEHTALNLMGAMAHGIYAGDAKQLSVHSTFPILAACEQEYGSVVLGMLSGKLSVESPR
ERQLADACRAKDPEWFKQMQQSSVLGFLPGLGALPSRLTQFLSSQPNVSMQLGETVSRLDGQSSHQIEITT
SQGQIYHADHIVSTLPSHALARISMPTTTSLPHLTHNPSADVALVNLAYEKCKVKPGLDGFGFLTPHADTM
PPSQFPGLLGMIFDSNSLGVQDQDSNMVRFTAMIGGADWNLAFGSLHDNDAISSKALTMATAALSKYLEIH
ESPAHYHCRILRQCIPQYLVGHRQRMNELHAALQHSFGHTMSVTGASYLGVSVPDCIKHSRMLIEDLVDTG
ALGSKQAVITGLEKVTLPMYYKL SEQ ID NO: 99
PPO from Spizellomyces sp. Protein.
>SEQ ID NO: 99
MSSPSHFAVLGGGVSGLSTAWYLSKLAPKTARITVVEKNARVGGWVHTNMQDGQLYELGPRTIRPVGVAGR
AVLDMVYRLNLVEEVLTTPKNSPAAINRYIYQNSRLHHLPTSPLDLLMPWKAKSPLLKGLLFSVLREPFVK
PTNASDESIHGFVERRFGRALADNLVSAVIHGIYAGDSTQLSVRSAMPFLWECEKKHGSVGRGVLAPPAVA
PIGDERAPLSVESNDAKKFISDIQRNSSIFSFKNGMQTLTDALKRDLDKEENVSFIRGNIESLSFKEGVEI
AHTASSQPLKADHVISAIPAVDLSRILPPSSHALSSLLSSIKSVDVAVVNISFGGHFSKILPVNGFGYLVP
ATEDTPILGTVFDSCAMPKQDSGDQTRVTVMMGGHKFHKYFGDPDVVSKEKLLETAMTAVRTHLGVNAEPI
ASSVVIHKQCIPQYVVGHRDRLHAIHEEVKSQHIQLSLVGASYLGVAVNDCVKGARDLVSNLLVETQAKQR
RITGLERIET SEQ ID NO: 100
PPO from Rhizophagus sp. Protein.
>SEQ ID NO: 100
MSSPNNFVILGGGISGLSAAWYLSRYAPSTTKILVLEGSNRFGGWIKSKRVGQHKILFEQGPRTLRPNGIG
GSVVLDMVNRLNLIPSLHAVTKDDDAAKDRFIYYPDKIVKLPGTSLLSSMKSVFTNNELLKSIPSILFEPF
IKPARNYHDETIHEFISRRESKSISDILISALIHGIYAGDINKLSIRSTFTRLYNLEQKYGSVIKGLLMSN
KEEFLSQQDKYLLKIINDENKDFLSIFKNVSLYSFKDGIEQLSSAIVNDLKNKENVQLKTNNQVTKLEFGE
NVKIFTNEAVYEADHVISALPSRALYNILPEKDVLPHLNYNPSVSVATINLAYAHPKILPVKGFGYLIPQS
TPHNPYHVLGVVFDSNAMPLQDEPSRTYTKLTIMMGGHYFNSISEKDDFPKKEILLQQSIEILEKHLGIYS
TPLYYLVDIQKNCIPQYYVGHYSRLKELHYAIKNHYANRLSVTGASYWGISINDCVLNSAKLVLNILSNSP
NVVTGLEEVEIQNEHYL
```

According to some embodiments, chimeric fungal-isolated PPO polypeptide is fused to chloroplast transit peptide (cTP), and have the amino acid sequence set forth in any one of SEQ ID NO: 8-14 and SEQ ID NO: 104-118;

```
SEQ ID NO: 8
PPO from Aspergillus sp. fused to cTP. Chimeric Protein.
>SEQ ID NO: 8
MELSLLRPTTQSLLPSFSKPNLRLNVYKPLRLRCSVAGGMRLPCASSRVFRQVRAPLALLSRGQRHAVHTK
QFDAAVIGGGITGLTAAYQLSRDPSCSKVTLYEKSPHLGGWLSSEQIPVPGGHVVFEYGPRTLRTSSPSCL
PMMDLIMNLDLLDDVLICDKKSPAAQNRYIYYPDHLVRLPFPPTEGLLKTAWTLLMEPLFETFLYSAIFEK
PKRAENTHILSRDESVADFVSRRFSPKISENLASAVMAGIFAGDVNRLSAEMAIGYVRELEKRYGSIVDGM
MTQRASEMRAMPMDELLALESVAVPSHSDDRYWKSLRAVVSDASVLTLKNGLGQLTDAMAAQLRSSRNVEV
VTGTEVTSLSQNPKTQDLTIGFGKNESKTHNRVIATHAPSSLARQIQNTKVGVVPSDTIRDLGQNNYAVTV
MVVNLYYEDPDLVPVEGFGYLLPSSVPFEQNPERALGVIFGSQSSEGQDTAPGTKLTVMMGGHLWDGWSES
DYPDPDKAIEMAQALLHRHLGIKTAPSVARARLLRDAIPQYTVGHLSRMKELSHSVRSDFHKRLTLAGAWY
GTVGIGVVDCIRQGYLASSYGVGSKKLGPGNSRRPWTKHDFHNWELEGGIATSPVRLDNVHVTERQHY SEQ ID NO: 9
PPO from Aspergillus sp. fused to cTP. Chimeric Protein.
>SEQ ID NO: 9
MELSLLRPTTQSLLPSFSKPNLRLNVYKPLRLRCSVAGGMRLPCASSRAFRQVRAPLALLHRGQRHAVHTK
QFDAAVIGGGITGLTAAYQLSRDPSCSKVTLYEKSSHLGGWLSSEQIPVPGGHVVFEYGPRTLRTSSPSCL
PMMDLIMNLDLLDDVLICDKKSPAAQNRYIYYPDHLVRLPFPPTEGLLKTAWTLLMEPLFETFLYSAIFEK
PKRAENTHILSRDESVADFVSRRFSPKISENLASAVMAGIFAGDVNRLSAEMAIGYVRELEKRYGSIVDGM
MTQRASEMRAMPMDELLALESVAVPSHSDDRYWKSLRAVVTDASVLTLKNGLGQLTDAMAAQLRSSRNVEV
VTGTEVTSLSQNPKTQDLTIGFGKNESRTHNRVIATHAPSSLARQIQNTKVGVVPSDTIRDLGQNNYAVTV
MVVNLYYEDPDLVPVEGFGYLLPSSVPFEQNPERALGVIFGSQSSEGQDTAPGTKLTVIMGGHLWDGWSES
DYPDPDKAIEMAQALLHRHLGIKTAPSVARARLLRDAIPQYTVGHLSRMKELSHSVRSDFHKRLTLAGAWY
GTVGIGVVDCIRQGYLASSYGVGSKKLGPGNSRRPWTKHDFHNWELEGGIATSPVRFDNVHVTERQHY SEQ ID NO: 10
PPO from Fusarium sp. fused to cTP. Chimeric Protein.
>SEQ ID NO: 10
MELSLLRPTTQSLLPSFSKPNLRLNVYKPLRLRCSVAGGMSRRAESTAVALLSSPAKSHLQPPLRRLDGI
RSLSTSSALARRRPIVACNYTQSFNNGRTFVSQAKDANIAVLGGGLTGLTAAYYLAKKLPSTAKITLYESS
DRLGGWIKTDRVPVDIEGKSGTLSFERGARSLSSLVGNTFRFDDLVLYDLALDLGLAINSPSQQPRYIYYP
DHLVPTPPNISIFDMLREPLYLEIIGASLGLGINSLRKRTLPSKDYSVSEWLYAVSNSRKGIGNLASAMMH
GIYGGDIHKLSARCVLDRLYWGWYLPNPGLSVRPMPVAEQALLETLGQDKQIQKMALEPRSALVDFGDKGM
ESLPQALSAALREQPNITIKTGEAVQDVVYNKANQQVHITSSNAKDNSKHNSKVYDKVISTLSAQDIALLA
GNKLPSLSTAHSVSVMTVNIWFPQENLKPPGFGYLIPNSVAPELNPEHALGVFFDSDVQTRSKDEPAGTKL
```

-continued

```
FVLMGGHYYDRPDVTPPTEEEAIIQARNLLERHLGIPRDAPAYATANFARECIPQHYVGHQDRLKAAHTEL
TRNFGGRLAVAGGSFTRIGAVASLRAGYDAATAAKKGLEATGLEYLNDIQQFSVVATSHIPVRHFK

SEQ ID NO: 11
PPO from Fusarium sp. fused to cTP. Chimeric Protein.
>SEQ ID NO: 11
MELSLLRPTTQSLLPSFSKPNLRLNVYKPLRLRCSVAGGMSRRRAESTAVALLSSPAKSHLQPPLRRLDGI
RSLSTSSALARRRPIVACNYTQSFNNGRTFVSQAKDANIAVLGGGLTGLTAAYYLAKKLPSTAKITLYESS
DRLGGWIKTDRVPVDIEGKSGTLSFERGARSLSSLVGNTFREDDLVLYDLALDLGLAINSPSQQPRYIYYP
DHLVPTPPNISIFDMLREPLYLEIIGASLGLGINSLRKRTLPSKDYSVSEWLYAVSNSRKGIGNLASAMMH
GIYGGDIHKLSARCVLDRLYWGWYLPNPGLSVRPMPVAEQALLETLGQDKQIQKMALEPRSALVDFGDKGM
ESLPQALSAALREQPNITIKTGEAVQDVVYNKANQQVHITSSNAKDNSKHNSKVYDKVISTLSAQDIALLA
GNKLPSLSTAHSVSVMTVNIWFPQENLKPPGFGYLIPNSVAPELNPEHALGVFFDSDVQTRSKDEPAGTKL
FVLMGGHYYDRPDVTPPTEEEAIIQARNLPERHLGIPRDAPAYATANFARECIPQHYVGHQDRLKAAHTEL
TRNFGGRLAVAGGSFTRIGAVASLRAGYDAATAAKKGLEATGLEYLNDIQQFSVVATSHIPVRHFK SEQ ID NO: 12
PPO from Fusarium sp. fused to cTP. Chimeric Protein.
>SEQ ID NO: 12
MELSLLRPTTQSLLPSFSKPNLRLNVYKPLRLRCSVAGGMSRRRAESTAVALLSSPAKSHLQPPLRRLDGI
RSLSTSSALARRRPIVACNYTQSFNNGRTFVSQAKDANIAVLGGGLTGLTAAYYLAKKLPSTAKITLYESS
DRLGGWIKTDRVPVDIEGKSGTLSFERGARSLSSLVGNTFRDDLVLYDLALDLGLAINSPSQQPRYIYYP
DHLVPTPPNISIFDMLREPLYLEIIGASLGLGINSVRKRTLPSKDYSVSEWLYAVSNSRKGIGNLASAMMH
GIYGGDIHKLSARCVLDRLYWGWYLPNPGLSVRPMPVAEQALLETLGQDKQIQKMALEPRSALVDFGDKGM
ESLPQALSAALREQPNITIKTGEAVQDVVYNKANQQVHITSSNAKDNSKHNSKVYDKVISTLSAQDIALLA
GNKLPSLSTAHSVSVMTVNIWFPQENLKPPGFGYLIPNSVAPELNPEHALGVFFDSDVQTRSKDEPAGTKL
FVLMGGHYYDRPDVTPPTEEEAIIQARNLLERHLGIPRDAPAYATANFARECIPQHYVGHQDRLKAAHTEL
TRNFGGRLAVAGGSFTRIGAVASLRAGYDAATAAKKGLEATGLEYLNDIQQFSVVATSQIPVRHFK SEQ ID NO: 13
PPO from Rhizopus sp. fused to cTP. Chimeric Protein.
>SEQ ID NO: 13
MELSLLRPTTQSLLPSFSKPNLRLNVYKPLRLRCSVAGGMSSVAILGGGISGLSAAYYLARMAPPTTKITL
IEGKKRLGGWIESRRVTPGHYDNIHQLPKNNSKENTILFEAGPRTLRPEGSNGAILLEMIRHLELNNENLM
SVSKSHPSARHRYIYYKDKINTLPSDLQSFLLNKPPVLKSVPLAALLEPLKPSRFDKDGIAKDGIQDESIY
SFMTRRFNEHTAIHLMGAVIHGIYAGDIKSLSLQSTLRSLYEAERIYGSAVLGMMKGASQVTTSVRERGMA
ARSRKEDPEWFGRMEKMSVIGFKSGMDTLPHQITSWLEQCPNVEVITDDPAEHIEIAHENKIKTQKGKTVH
ADHIISTLPSPVLERLVQHQPVLPHLSYNPSADVAVVNLAYSPDEMKLQYDGFGFLTPHRDTPYGNPLPGT
LGVVFDSNALPIESERAVKLTAMIGGSDWKDAFGNVPIDELEPKVALDYTRKAVGTFLDIHAEPRYSMVNL
QKQCIPQYLVGHQDRMLSLHHAIKKNYGHALSVSGASYLGVSVPDCIKNSRMLVEELLVSGALGSRQKVVT
GLGKLEEQPTVDEMRDNARLSRGNTSVIMKS SEQ ID NO: 14
PPO from Penicillium sp. fused to cTP. Chimeric Protein.
>SEQ ID NO: 14
MELSLLRPTTQSLLPSFSKPNLRLNVYKPLRLRCSVAGGMRLLTASKGLRSPQKPLISAIRCQHRAYNAAV
IGGGITGLTAAWQLIQDRECSSVTIYEKSRRLGGWLQSETIPVEGGEVVFEYGPRTLRSAMPASLPLLYLV
SNLGLFDELITTSKRSPAALNRYIYYPDHLVRLPSPDPDLSLMENARNIFRTITTEPLFEGFITGLLSEPN
KPARPQEEWAIDESLAEFITRRFNRKIADNLVSAVMHGIYAGNIDEMSAQAIMGPLRNLEDGGILFGLLIK
SIMGKKTRSMDDFLAVDAVYKTPETMQRLDEINRVVKTASTFTFKRGTQQLVEGLTRALRTSEKVRLVMDA
DILALDPPANRGHKLKIYTGIRGEESFDHVISAISAPAMARILDPQGVKIDCDPEDEYRALWNSKKARHP
KPNIGTVSGLHFFRHATTVMVVNLYYKTPNLLPVDGFGYLIPRSIPYEQNPECGLGVIFASASSSGESPVA
PYPKVSQDSAPGTKITIMFGGHYWDGWKKQDYPDHKTAVRMAKDMLERHLGITEPPALVRTRLQENAIPKY
TPLHIHQIYALSRWAKEEYHNRLVLVGNSFSGVGVGDCVRQGIMAATHGVGRHKLTATPRLKSKDWCPWKE
YNYQHWDLKGGVPTAPVRLFESDI SEQ ID NO: 104
PPO from Trichoderma sp. fused to cTP. Chimeric Protein
>SEQ ID NO: 104
MELSLLRPTTQSLLPSFSKPNLRLNVYKPLRLRCSVAGGMRLPCASSRVFRQVRAPLALLRRGQRHALHTK
QFDAAVIGGGITGLTAAYQLSRDPSCSKVTLYEKSSHLGGWLSSEQIPVRGGHVVFEYGPRTLRTSAPSCL
PMMDLIMNLDLLDDVLICDKKSPAAQNRYIYYPDHLVRLPFPPTEGLLKTAWTLLMEPLFETFLQSALFEK
PKRAVDGDVLSRDESVADFVSRRFSPKMSENLASAVMAGIFAGDVNRLSADMAIGYVRELEKRYGSIVDGM
MTQRASELRAMPMDEFLALESVAVPSHKDDRYWKSLRAVVSDASVLTLKNGLGQLTDAMAAQLRSSNNVEV
VSGTEVTSLSQNPETRDLTIGFGKNESKTHNRVIATHAPSSLARQLENTKVGVAPSDTLRALGQNNYAVTV
MVVNLYYEDPDLVPVQGFGYLLPSSIPFEENPERALGVIFGSQSSEGQDTAPGTKLTVMMGGHLWDGWSES
DYPDPDKAVEMAQALLHRHLGIKTAPSVARARLLRDAIPQYTVGHLSRMKELSQSVRGDFHKRLTLAGAWY
GTVGIGVVDCIRQGYIASSFGVGSKKLGPGGGRRPWTKHDFHNWELEGGICTSPVRFDNVHITERQH SEQ ID NO: 105
PPO from Aspergillus sp. fused to cTP. Chimeric Protein
>SEQ ID NO: 105
MELSLLRPTTQSLLPSFSKPNLRLNVYKPLRLRCSVAGGMRLPCVPSCALRGVRTPLAFARIGQRYSSTYD
AAVIGGGITGLTAAYRLSQDPNCSKITLYEKAPRVGGWLLSEKIPVEGGNVVFEYGPRTLRTAVPSCLPLL
DLLVELGLHDDVLLTSSSSPAARNRYIYYPDHLVRMPAPDPNAGPIENITNPLFAMLREPVFEGLIASALL
EPVRAPPDHKTFNSDESVADFVSRRLCPEVADNLVSALFHGIYAGDISRLSAQTLLGTFRDLENDDRRVIG
GYINSLMSDVKLMAMDDLLALESVAHEKPGMYWKSLRTLVNKTSVLTLKDGLSQLSDALVDALKKSKKVDV
LANTDVKSITQNPMTDDLIVGSGQDRSIHNRVIATIPAPELANKLATTTVKDQKVPQSTIRNLQEHNYAV
TVMVVNLYFPNPDLLPVSGFGYLIPRSIPYEQNPERALGVIFGSDSSVGQDTAPGTKLTVMMGGHWWDGWK
```

-continued

```
ESDYPDHDTAVAMSRALLHRHLGITDAPTLTSSRLQRNAIPQYTVGHLSRMRELSRSTRHELNNRLTLAGS
WYNGVGVTDCIRQGYLAASFGVGARKLGPGDGDRPWRRFDYEKWELEGGIVTSPVRWAEVYRTERKHF

SEQ ID NO: 106
PPO from Aspergillus sp. fused to cTP. Chimeric Protein
>SEQ ID NO: 106
MELSLLRPTTQSLLPSFSKPNLRLNVYKPLRLRCSVAGGMRLPHASSHALKGSRLSLALARNGQRRSLHTP
TYDAAVVGGGITGLTTAYRLSRDPKCSKITLYEKSKNVGGWLQSEKIPFKDGHVVFEYGPRTLRTALPSCL
PLLDLLEELDLLGEVLVTSKTSAAALNRYIYYPDHLARVPAPDPARGALGNALSLMWSLFREPVFKSIFLG
IYNDIQSPAPQKLKADESVGDFISRRLSPELADNLVSSVFHGIYAGDIYQLSAEALLGQHREPEGGVPSIM
LRLINEARMNHTPELLDDQLAMELILEEKSRSYLNALAVLVRQASVLTLRNGLGQLTDALLAALAKSKKVD
ILPEAEVTAISRNQNSSNITISHGQDEHRMHNRVVSTIPAPHLAKALRQGGGEDKKLPHNTIQALEEHNYA
VTVMVVNLFYEKEDLLPVKGFGYLIPRSIPFEQNPERGLGVIFGSETSAGQDTVPGTKLTVMLGGHLWDGW
TESDYPDHDTAVKMARTLLERHLGITDAPAISRSRLHRNAIPQYTVGHPARMDRISESARADFSNRLSLAG
SWYGGIGVVDCIRHAYLTAAYGVSAQKLRSGGQDRPWKLFNYTQWELEGGIVKSPVRLVWRRPDSKN SEQ ID NO: 107
PPO from Fusarium sp. fused to cTP. Chimeric Protein
>SEQ ID NO: 107
MELSLLRPTTQSLLPSFSKPNLRLNVYKPLRLRCSVAGGMSHSRAESTAVALLSSAAHSTTKPHLRVP
LCRLNGFRNLSTCSASALTRRRPIIACKHTQSSRDGRRYVSQAKDANIAVIGGGLTGLSAAYYLAKKL
PSTTKITLYEANDRLGGWIKTDRVPVDIEGKKGIVSFERGSRSLTSLVGNTFREDDLVLYDLTLDLGL
SLNFPPARPRYVYYPDHLVATPPNISIFDILREPLYLESFGAGLGLMINQLRKRQLPAEDESVADWLY
KVTNSRKGIGNLASAMMHGIYGGDINKLSARSVLDRIYWGWYMPNPGLHARPMPLPEQLILETLGQDR
QIQKLALEPKSTLIDFGDKGMESLPQAIGAALRDQPNVTIMTGEAVNDIQYDEAKKQVQINSENTQNE
EKSNSQAYDKIVSTLSAQHIARLAGDKVQSLSAAHSVSVMTVNIWFPQENLKPPGFGYLIPDSVEPEL
NPEHALGVFFDSDVGTRSKDEPAGTKLFVLMGGHYYDRPGVTPPTEDEAIVQARNLLERHLGIPRDAP
AYATANFAKECIPQHNVGHQDLLRNAHAELKQNFGGRLAVAGGSFHRIGTIASLRSGYDAAVATKNGL
EATGLEYLETITEFAVVPTDMIPVRLEK SEQ ID NO: 108
PPO from Fusarium sp. fused to cTP. Chimeric Protein
>SEQ ID NO: 108
MELSLLRPTTQSLLPSFSKPNLRLNVYKPLRLRCSVAGGMSRRRAESTAVALLGSPAKPHLPLPLRRLDAI
RSLSTSSALTRRRPIVARNYTQFFNNGRTFVSQAKDANIAVLGGGLTGLTAAYYLAKKLPSTAKITLYESS
DRLGGWIKTDRVPVDVEGKSGTVSFERGARSLSSLAGNTFRFDDLVLYDLALDLGLVVNSPRQQPRYIYYP
DHLVPMPPNVSIFDIFREPLYLESIGASLGLGINSLRKRTLPSKDYSVSEWLYAVSNSRKGVGTLASAMMH
GIYGGDIDKLSARSVLDRVYWGWYLPNPGLSARPMPVAEQTLLETLGQDKQIQKMALEPRSALVDFGDKGM
ESLPQALSTALREQPNVTIKTGEAVQDVVHNKTNQQVHVTSSNAKNKSEHNSKVYDKVISTLSAQDIARLT
GDKLPSLSTAHSVSVMTVNIWFPRENLKPPGFGYLIPNSVAPELNPEHALGVFFDSDVQTRSKDEPAGTKL
FVLMGGHYYDRPDVTPPTEEEAILQARNLLERHLGIPRDAPAYATANFARECIPQHYVGHQDRLRAAHTEL
THNFGGRLAVAGGSFTRIGAIASLRAGYDAATAAKEGLEATGLEYLNDIQQFSVVATSHIPVRHFK SEQ ID NO: 109
PPO from Rhizopus sp. fused to cTP. Chimeric Protein
>SEQ ID NO: 109
MELSLLRPTTQSLLPSFSKPNLRLNVYKPLRLRCSVAGGMSSVAILGGGISGLSAAYYLARMAPPTTKITL
IEGKKRLGGWIESRRVTPGHYDNIHQLPKNNSKENTILFEAGPRTLRPEGSNGAILLEMIRHLELNNENLM
SVSKSHPSARHRYIYYKDKINTLPSDLQSFLLNKPPVLKSVPLAALLEPLKPSREDKDGIAKDGIEDESIY
SFMTRRFNEHTAIHLMGAVIHGIYAGDIKSLSLQSTLRSLYEAERIYGSAVLGMMKGASQVTTSVRERGMA
ARSRKEDPEWFGRMEKMSVIGFKSGMDTLPHQITSWLEQCPNVEVITDDPAEHIEIAHENKIKTQKGKTVH
ADHIISTLPSPVLERLVQHQPVLPHLSYNPSADVAVVNLAYSPDEMKLQYDGFGELTPHRDTPYGNPLPGT
LGVVFDSNALPIESERAVKLTAMIGGSDWKDAFGNVPIDELEPKVALDYTRKAVGTFLDIHAEPRYSMVNL
QKQCIPQYLVGHQDRMLSLHHAIKKNYGHALSVSGASYLGVSVPDCIKNSRMLVEELLVSGALGSRQKVVT
GLGKLEEQPTVDEMRDNARLSRGNTSVIMKS SEQ ID NO: 110
PPO from Rhizopus sp. fused to cTP. Chimeric Protein
>SEQ ID NO: 110
MELSLLRPTTQSLLPSFSKPNLRLNVYKPLRLRCSVAGGMSSIAVLGGGISGLSAAYYLARLAPASTKIVL
IEGKDRLGGWIHSRRVAPGKYSRDKAPQLSNEKDSILFEAGPRSLRPEGPNGAILLEMIQNLDLNNEGLLS
VPKTDPSVKNRYIYYDGEINTLPSGPISMLLKKPPVFKSVILAGALEPLRSSRFKNGKPKDGIEDESMYNF
MKRRFNEHTAINLMGAVAHGVYAGDVKQLSIQSTLRMLYEAEKNYGSVIVGMMRGAANTSTMRERGMAVRS
RDKDPEWFGRMEKMSVLGFKDGMETLPDRLCSWLEQRPNVEIIRNDPVESIEPLENGKESKIKTKSNEFFA
DHVLSTIPSFTLEKLIKPNSLPNLSHNPASDVAVVNFAYSPEVKLGYDGFGFLTPHRDTKYRVPVPGTLGV
IFDSNAMPGQETEQPEVVKVTAMMGGADWKDAFGKATIDELDPEVAYKYARKGMSVFLNLHDEPTHAMVNL
QKQCIPQYVVGHEGRMRELHHALKQNYGHLMSLTGASYMGVSVPDCIKNSRMLVEELLVSGALGSRDKVVT
GLGRTVESNSKELQDGARISKGTVDVIMKS SEQ ID NO: 111
PPO from Rhizopus sp. fused to cTP. Chimeric Protein
>SEQ ID NO: 111
MELSLLRPTTQSLLPSFSKPNLRLNVYKPLRLRCSVAGGMSAVILGGGISGLSAAYYLARMAPSTTKITLI
EGKNRLGGWIESRRVTAGHYDNIHCLPKENQQNTVLFEAGPRTLRPEGINGAILLEMIRHLDLNNDDLLSI
PKSHPSAKNRYIYYQDKINKLPSDFGSFLRQRPPVLKSVPLAGLLEPLRTSRFENGLPKNGEEDESIYSFI
SRRFNEHTATHLMGAVIHGIYAGDVRALSLQSTLNSLYEAERTYGSAVLGMLKGVSQATQTMRERGMAARS
RKDDPDWFGRMEKMSVIGFKTGMDSLPDKITAWLKQRPNVEIITHDSVQHIGEGKIKTEHREIEADHIIST
LPSSVLHSLLSRPLPHLMHNPAVDVAVVNLAYPSDIKLDYDGFGFLTPHRDSKYPNPVPGTLGVVEDSNSL
PIDSEHATKLTVMMGGSDWKDAFGDVSLDQLDPQVALQRARQAVSTFLGIHAEPHASMVHLQKQCIPQYLV
```

GHRQRMRSLHHAIKQDYGHSLSVSGASYLGVSVPDCIKNSRMLVEELLVSGALGSRQKIVTGLGRLEQEMT
VEEMRDNARVSKSNTSVIIKS

SEQ ID NO: 112
PPO from *Penicillium* sp. fused to cTP. Chimeric Protein
>SEQ ID NO: 112
MELSLLRPTTQSLLPSFSKPNLRLNVYKPLRLRCSVAGGMRLLTASKGLRSPQKPLISAIRCQHRSYNAAV
IGGGITGLTAAWQLIQDRECSSVTIYEKSRRLGGWLQSETIPVEGGEVVFEYGPRTLRSAMPASLPLLYLV
SNLGLFDELITTSKRSPAALNRYIYYPDHLVRLPTPDPDLSLMENARNIFRTITTEPLFEGFITGLLSEPN
KPARPQEEWAIDESLAEFITRRFNRKIADNLVSAVMHGIYADNIDEMSAQAIMGPLRNLEDGGILFGLLIK
SIMGKKTRSMDDFLAVDAVYKTPETMQRLDEINRVVKTASTFTFKRGTQQLVEGLTRALRASEKVRLVMDA
DILALDPPANRGHKLKIYTGIRGEESFDHVISAISAPAMARILDPQGQVKIDCDPEDEYRALWNSKKARHP
KPNIGTVSGLHFFRHATTVMVVNLYYKTPNLLPVDGFGYLIPRSIPYEQNPECGLGVIFASASSSGESPVA
PYPKVSQDSAPGTKITIMFGGHYWDGWKKQDYPDHKTAVRMAKDMLERHLGITEPPALVRTRLQENAIPKY
KPPHIHQIYALSRWAKEEYHNRLVLVGNSFSGVGVGDCVRQGIMAATHGVGRHKLTATPRLESKDWCPWKE
YNYQHWDLKGGVPTAPVRLFESDI SEQ ID NO: 113
PPO from *Penicillium* sp. fused to cTP. Chimeric Protein
>SEQ ID NO: 113
MELSLLRPTTQSLLPSFSKPNLRLNVYKPLRLRCSVAGGMRLPCVSRALRPRPRQLTHLLNGQKCTYSAVV
LGGGITGLTAAWQLAQDPICKSITLFEKTDRLGGWIDSETVPVDGGNVVFEYGPRTLRSSLPGSLPLLYLA
TNLGLYKDLIVTPNTSPAAQNRYIYYPDRLVRMPAPKPELSFAENFDSFVNTMMEPLFNKFLSGIVKDVFT
PPRHPTEWAEDESVADFIGRRFGPKVADNIVSAVYHGIYAGDIDQLSAQTLLGSVRNLEGGIGGIGGLVSG
GVTASLISRSLSKTKTRNMEDFMAIDAISAGPELVRRQHDLEVLAAGASTFTFKRGVGQLTEALVASLKAS
GKVRFQMNKEITGLRALARAPAIAMEFWSDRHSQVKTFEYDYVISTIPPVALAKTMRKTEQLEAKLYPVGL
TPLLLRRQDYAVTVLVVNLYYPNPNLLPVEDGFGYLIPRSIPYEQNPECGLGVIFASSSSVGNGTDPSSSE
VNQDSAPGTKITVMLGGHYWDGFEEYPDHDTAVKMARDMLKRHMNITDTPTVTRSRLQKDAIPQYTVGHLD
RMYKLSDTVRKDYQKRLILAGNWYNGVSVGDCVKQGILSATYGIGRNRLNYEPSPWRPWTSFDYKRWKLEG
GIVMSPVRLVDSKI SEQ ID NO: 114
PPO from *Trichoderma* sp. fused to cTP. Chimeric Protein
>SEQ ID NO: 114
MELSLLRPTTQSLLPSFSKPNLRLNVYKPLRLRCSVAGGMSLKRADGAAMAFLRLSSAVCGRRRIPAG
GLPADANVAVLGGGLTGLTTAYYLAKWLPPTAKITLLEASDRLGGWIKTDRVPVKVGGVEGVVSFERG
PRSLSSLNKSTWREDDLVLWDLALDLGLRVVSPPDKPRYIYYPDHLVPLPPHTSLAAFASEPLVLESL
WAGFGYVLRRLFSRKAGVPVQDLSIADWIQHITGSRAVAENLASAMVHGIYGGDIYTLSARSVLDRFY
WVHYLPALGPDVRHMALSEQVFMEAMGQDPLIRKLAQQPRGALLNFGEAGMETLPIALADALNGQANV
EVKLGAKVTGLEYESETEMMKITTTGQDDSPAEKYHKVISTLPSQHLARITDTLPSLASSHAVSIMTV
NIWYPQTNLKPPGFGYLIPLSVPAEQNPERALGVFFDSDVGVRGPDEPAGTKLFVLMGGHYYDKKQPG
ASVRVPSEEEAIEQAKRVLERHLGIPQSTPCFAMARLASECIPQYVCGHQDTMAAADEDLRDSEDGRL
AVAGGSYTKIGAMGALRNGYDIANTVVREDWLTTGLEQLEFPTQFCGVPTERIPVRRESRR SEQ ID NO: 115
PPO from *Rhodotorula* sp. fused to cTP. Chimeric Protein
>SEQ ID NO: 115
MELSLLRPTTQSLLPSFSKPNLRLNVYKPLRLRCSVAGGMQSYSGNALARQSVPIKPIRRRTPRLNLIRSL
PSPRFFVTSPSSSQRHDHPYHTLAILGGGLSGLSTAHYFLRTLSPSLRDQTRIVVLEKEERVGGWCRAVRI
QNGRRLGENEKPEGTEDLLVFETGPRSVRPVGLLGWLTIEMAHELGLTPSIVTVPKSAPSARNRFIYTGHR
SSTSISPILKAALPTIPSALLEPFRPRSPLHDDPSGLADESVDSFIARRFGRRLADELASAGIHGIYAGDT
RRLSVRAVLPALWELEKEWGSVVIGALFGSFARRRGWKKNSPWRMRQQAETEEMERVKERIRAKGGEALVE
DMEKASVWGVKGGLQVVTETLREKLEAEGVEFWMGEKGKVEHVEKVDGGWQIRTSSGALDASQLVTTIPQL
LPSSLAPPALPATTVSVVNLAFEKPAPGSPPLHPAGFGYLIPRTVPSSLNPHRALGVIFDSDVMPDVDSSS
SLGLTKLSLLLGGSYWLDRHPPPQPSHDDLVNAALETLRLHPPDRPIPKPVHAFTHTHVNCIPQVPPGEMP
SFRAFGDRLREAGNVAVVGGGFAAVGVNGCVKAAWEVGSAMAQAVNAQAGGKEGEGEEKVREAVARTVKTG
TEMWEL SEQ ID NO: 116
PPO from *Hesseltinella* sp. fused to cTP. Chimeric Protein
>SEQ ID NO: 116
MELSLLRPTTQSLLPSFSKPNLRLNVYKPLRLRCSVAGGMPRSIVVLGGGISGLSAAYYLSRLVPQAHIRL
IESNKRAGGFIKTQQVNDHLIFEAGPRTLRPHGTSGTVLLDMIKDLDLSPLLVNIPKSHPSAQHRYIEYHG
QINQLPSGLADMLLHSPPIMDSVITAGMREPFLARASTTKDESLYNFMERRFNEHTALNLMGAMAHGIYAG
DAKQLSVHSTFPILAACEQEYGSVLGMLSGKLSVESPRERQLADACRAKDPEWFKQMQQSSVLGFLPGLG
ALPSRLTQFLSSQPNVSMQLGETVSRLDGQSSHQIEITTSQGQIYHADHIVSTLPSHALARISMPTTTSLP
HLTHNPSADVALVNLAYEKCKVKPGLDGFGFLTPHADTMPPSQFPGLLGMIFDSNSLGVQDQDSNMVRFTA
MIGGADWNLAFGSLHDNDAISSKALTMATAALSKYLEIHESPAHYHCRILRQCIPQYLVGHRQRMNELHAA
LQHSFGHTMSVTGASYLGVSVPDCIKHSRMLIEDLVDTGALGSKQAVITGLEKVTLPMYYKL SEQ ID NO: 117
PPO from *Spizellomyces* sp. fused to cTP. Chimeric Protein
>SEQ ID NO: 117
MELSLLRPTTQSLLPSFSKPNLRLNVYKPLRLRCSVAGGMSSPSHFAVLGGGVSGLSTAWYLSKLAPKTAR
ITVVEKNARVGGWVHTNMQDGQLYELGPRTIRPVGVAGRAVLDMVYRLNLVEEVLTTPKNSPAAINRYIYQ
NSRLHHLPTSPLDDLLMPWKAKSPLLKGLLFSVLREPFVKPTNASDESIHGFVERRFGRALADNLVSAVIHG
IYAGDSTQLSVRSAMPFLWECEKKHGSVGRGVLAPPAVAPIGDERAPLSVESNDAKKFISDIQRNSSIFSF
KNGMQTLTDALKRDLDKEENVSFIRGNIESLSFKEGVEIAHTASSQPLKADHVISAIPAVDLSRILPPSSH
ALSSLLSSIKSVDVAVVNISFGGHFSKILPVNGFGYLVPATEDTPILGTVEDSCAMPKQDSGDQTRVTVMM

```
GGHKFHKYFGDPDVVSKEKLLETAMTAVRTHLGVNAEPIASSVVIHKQCIPQYVVGHRDRLHAIHEEVKSQ
HIQLSLVGASYLGVAVNDCVKGARDLVSNLLVETQAKQRRITGLERIET

SEQ ID NO: 118
PPO from Rhizophagus sp. fused to cTP. Chimeric Protein
>SEQ ID NO: 118
MELSLLRPTTQSLLPSFSKPNLRLNVYKPLRLRCSVAGGMSSPNNFVILGGGISGLSAAWYLSRYAPSTTK
ILVLEGSNRFGGWIKSKRVGQHKILFEQGPRTLRPNGIGGSVVLDMVNRLNLIPSLHAVTKDDDAAKDRFI
YYPDKIVKLPGTSLLSSMKSVFTNNFLLKSIPSILFEPFIKPARNYHDETIHEFISRRESKSISDILISAL
IHGIYAGDINKLSIRSTFTRLYNLEQKYGSVIKGLLMSNKEEFLSQQDKYLLKIINDENKDFLSIFKNVSL
YSFKDGIEQLSSAIVNDLKNKENVQLKTNNQVTKLEFGENVKIFTNEAVYEADHVISALPSRALYNILPEK
DVLPHLNYNPSVSVATINLAYAHPKILPVKGFGYLIPQSTPHNPYHVLGVVEDSNAMPLQDEPSRTYTKLT
IMMGGHYFNSISEKDDFPKKEILLQQSIEILEKHLGIYSTPLYYLVDIQKNCIPQYYVGHYSRLKELHYAI
KNHYANRLSVTGASYWGISINDCVLNSAKLVLNILSNSPNVVTGLEEVEIQNEHYL According to some embodiments, human PPO have the amino acid sequence set
forth in SEQ ID NO: 101;

SEQ ID NO 101: 4IVO_B. Structure of human protoporphyrinogen IX
oxidase(R59Q) [Homo sapiens]
>SEQ ID NO: 101
MGRTVVVLGGGISGLAASYHLSRAPCPPKVVLVESSERLGGWIRSVRGPNGAIFELGPQGIRPAGALGART
LLLVSELGLDSEVLPVRGDHPAAQNRFLYVGGALHALPTGLRGLLRPSPPFSKPLFWAGLRELTKPRGKEP
DETVHSFAQRRLGPEVASLAMDSLCRGVFAGNSRELSIRSCFPSLFQAEQTHRSILLGLLLGAGRTPQPDS
ALIRQALAERWSQWSLRGGLEMLPQALETHLTSRGVSVLRGQPVCGLSLQAEGRWKVSLRDSSLEADHVIS
AIPASVLSELLPAEAAPLARALSAITAVSVAVVNLQYQGAHLPVQGFGHLVPSSEDPGVLGIVYDSVAFPE
QDGSPPGLRVTVMLGGSWLQTLEASGCVLSQELFQQRAQEAAATQLGLKEMPSHCLVHLHKNCIPQYTLGH
WQKLESARQFLTAHRLPLTLAGASYEGVAVNDCIESGRQAAVSVLGTEPNS
```

According to some embodiments, plant PPO have the amino acid sequence set forth in any one of SEQ ID NOs: 102-103 and SEQ ID NOs: 119-121:

```
SEQ ID NO: 102
Glycine max protoporphyrinogen oxidase 1, chloroplastic [Glycine max]
XP_003536005.1
>SEQ ID NO: 102
MVSVFNEILFPPNQTLLRPSLHSPTSFFTSPTRKFPRSRPNPILRCSIAEESTASPPKTRDSAPVDCVVVG
GGVSGLCIAQALATKHANANVVVTEARDRVGGNITTMERDGYLWEEGPNSFQPSDPMLTMVVDSGLKDELV
LGDPDAPRFVLWNRKLRPVPGKLTDLPFFDLMSIGGKIRAGFGALGIRPPPPGHEESVEEFVRRNLGDEVE
ERLIEPFCSGVYAGDPSKLSMKAAFGKVWKLEKNGGSIIGGTFKAIQERNGASKPPRDPRLPKPKGQTVGS
FRKGLTMLPDAISARLGNKVKLSWKLSSISKLDSGEYSLTYETPEGVVSLQCKTVVLTIPSYVASTLLRPL
SAAAADALSKFYYPPVAAVSISYPKEAIRSECLIDGELKGFGQLHPRSQGVETLGTIYSSSLFPNRAPPGR
VLLLLNYIGGATNTGILSKTDSELVETVDRDLRKILINPNAQDPFVVGVRLWPQAIPQFLVGHLDLLDVAKA
SIRNTGFEGLFLGGNYVSGVALGRCVEGAYEVAAEVNDELTNRVYK SEQ ID NO:103
Nicotiana tabacum protoporphyrinogen oxidase, mitochondrial, Accession number:
NP_001312887.1
>SEQ ID NO: 103
MAPSAGEDKHSSAKRVAVIGAGVSGLAAAYKLKIHGLNVTVFEAEGKAGGKLRSVSQDGLIWDEGANT
MTESEGDVTFLIDSLGLREKQQFPLSQNKRYIARNGTPVLLPSNPIDLIKSNFLSTGSKLQMLLEPIL
WKNKKLSQVSDSHESVSGFFQRHFGKEVVDYLIDPFVAGTCGGDPDSLSMHHSFPELWNLEKREGSVI
LGAIRSKLSPKNEKKQGPPKTSANKKRQRGSFSFLGGMQTLTDAICKDLREDELRLNSRVLELSCSCT
EDSAIDSWSIISASPHKRQSEEESFDAVIMTAPLCDVKSMKIAKRGNPFLLNFIPEVDYVPLSVVITT
FKRENVKYPLEGFGVLVPSKEQQHGLKTLGTLFSSMMFPDRAPNNVYLYTTEVGGSRNRELAKASRTE
LKEIVTSDLKQLLGAEGEPTYVNHLYWSKAFPLYGHNYDSVLDAIDKMEKNLPGLFYAGNHRGGLSVG
KALSSGCNAADLVISYLESVSTDSKRHC SEQ ID NO: 119
PPO from Arabidopsis thaliana, Mitochondrial AtPPO2
>SEQ ID NO: 119
MASGAVADHQIEAVSGKRVAVVGAGVSGLAAAYKLKSRGLNVTVFEADGRVGGKLRSVMQNGLIWDEGANT
MTEAEPEVGSLLDDLGLREKQQFPISQKKRYIVRNGVPVMLPTNPIELVTSSVLSTQSKFQILLEPFLWKK
KSSKVSDASAEESVSEFFQRHFGQEVVDYLIDPFVGGTSAADPDSLSMKHSFPDLWNVEKSFGSIIVGAIR
TKFAAKGGKSRDTKSSPGTKKGSRGSFSFKGGMQILPDTLCKSLSHDEINLDSKVLSLSYNSGSRQENWSL
SCVSHNETQRQNPHYDAVIMTAPLCNVKEMKVMKGGQPFQLNFLPEINYMPLSVLITTFTKEKVKRPLEGE
GVLIPSKEQKHGFKTLGTLFSSMMFPDRSPSDVHLYTTFIGGSRNQELAKASTDELKQVVTSDLQRLLGVE
GEPVSVNHYYWRKAFPLYDSSYDSVMEAIDKMENDLPGFFYAGNHRGGLSVGKSIASGCKAADLVISYLES
CSNDKKPNDSL SEQ ID NO: 120
PPO from Nicotiana tabacum, Chloroplastic NtPPO1
>SEQ ID NO: 120
MTTTPIANHPNIFTHQSSSSPLAFLNRTSFIPFSSISKRNSVNCNGWRTRCSVAKDYTVPSSAVDGGPAAE
LDCVIVGAGISGLCIAQVMSANYPNLMVTEARDRAGGNITTVERDGYLWEEGPNSFQPSDPMLTMAVDCGL
```

-continued

```
KDDLVLGDPNAPRFVLWKGKLRPVPSKLTDLPFFDLMSIPGKLRAGFGAIGLRPSPPGHEESVEQFVRRNL
GGEVFERLIEPFCSGVYAGDPSKLSMKAAFGKVWKLEETGGSIIGGTFKAIKERSSTPKAPRDPRLPKPKG
QTVGSFRKGLRMLPDAISARLGSKLKLSWKLSSITKSEKGGYHLTYETPEGVVSLQSRSIVMTVPSYVASN
ILRPLSVAAADALSNFYYPPVGAVTISYPQEAIRDERLVDGELKGFGQLHPRTQGVETLGTIYSSSLFPNR
APKGRVLLLNYIGGAKNPEILSKTESQLVEVVDRDLRKMLIKPKAQDPLVVGVRVWPQAIPQFLVGHLDTL
STAKAAMNDNGLEGLFLGGNYVSGVALGRCVEGAYEVASEVTGFLSRYAYK

SEQ ID NO: 121
PPO from Arabidopsis thaliana, Chloroplastic AtPPO1
>SEQ ID NO: 121
MELSLLRPTTQSLLPSFSKPNLRLNVYKPLRLRCSVAGGPTVGSSKIEGGGGTTITTDCVIVGGGISGLCI
AQALATKHPDAAPNLIVTEAKDRVGGNIITREENGFLWEEGPNSFQPSDPMLTMVVDSGLKDDLVLGDPTA
PRFVLWNGKLRPVPSKLTDLPFFDLMSIGGKIRAGFGALGIRPSPPGREESVEEFVRRNLGDEVFERLIEP
FCSGVYAGDPSKLSMKAAFGKVWKLEQNGGSIIGGTFKAIQERKNAPKAERDPRLPKPQGQTVGSFRKGLR
MLPEAISARLGSKVKLSWKLSGITKLESGGYNLTYETPDGLVSVQSKSVVMTVPSHVASGLLRPLSESAAN
ALSKLYYPPVAAVSISYPKEAIRTECLIDGELKGFGQLHPRTQGVETLGTIYSSSLFPNRAPPGRILLLNY
IGGSTNTGILSKSEGELVEAVDRDLRKMLIKPNSTDPLKLGVRVWPQAIPQFLVGHEDILDTAKSSLTSSG
YEGLFLGGNYVAGVALGRCVEGAYETAIEVNNEMSRYAYK
```

According to some embodiments, chloroplast transit peptide (cTP) have the amino acid sequence set forth in SEQ ID NO: 15:

```
SEQ ID NO: 15
cTP from Arabidopsis thaliana PPOX1 Protein
>SEQ ID NO: 15
MELSLLRPTTQSLLPSFSKPNLRLNVYKPLRLRCSVAGG
```

The following examples are presented in order to more fully illustrate some embodiments of the invention. They should in no way be construed, however, as limiting the broad scope of the invention. One skilled in the art can readily devise many variations and modifications of the principles disclosed herein without departing from the scope of the invention.

EXAMPLES

Example 1—in Planta Screening of PPO Tolerance Genes and Identification of Fungal-Isolated PPO Tolerance In planta screen of transgenic plants was performed to identify transgenes conferring resistance against PPO-type inhibitor herbicides. Transgenic plants exhibiting PPO herbicide tolerance were sampled and PPO herbicide-tolerance genes were isolated and annotated. Fungal genes were identified as conferring the exhibited tolerance. The fungal origin of each gene was identified using nucleic acid sequencing. Each tolerance conferring native gene was amplified form the genomic DNA (gDNA) of the origin fungi with a specific primer set complementing to the coding sequence (cds) or to the untranslated regions (UTR) of the gene The amino acid sequences of the isolated fungal PPO genes are set forth in:

SEQ ID NO: 1 (PPO from *Aspergillus* sp.);

SEQ ID NO: 2 (PPO from *Aspergillus* sp.);

SEQ ID NO: 3 (PPO from *Fusarium* sp.);

SEQ ID NO: 4 (PPO from *Fusarium* sp.);

SEQ ID NO: 5 (PPO from *Fusarium* sp.);

SEQ ID NO: 6 (PPO from *Rhizopus* sp.);

SEQ ID NO: 7 (PPO from *Penicillium* sp.).

Example 2—Assessment of Fungal-Isolated PPO Gene Tolerance in Transgenic Plants

Methods:

Cloning and transformation of fungal PPO genes—The nucleotide sequences encoding the PPO protein were cloned into a binary plant expression vector under the control of the 35S constitutive promoter and HSP terminator.

The vectors were used to transform *Arabidopsis* plants using *agrobacterium* according to the flower dipping method.

Generation of cTP chimeric PPO genes—The sequence of the N-terminal chloroplast transit peptide (cTP) of the chloroplast PPO from *Arabidopsis thaliana* (AtPPO1) (amino acids 1-38 (AtcTP_38)) were added to the sequence of the fungal PPO tolerance genes, in order to enhance the performance of their polypeptides as PPO inhibitors resistant genes. (SEQ ID NO: 8 was cloned from SEQ ID NO: 1, SEQ ID NO: 9 was cloned from SEQ ID NO: 2, SEQ ID NO: 10 was cloned from SEQ ID NO: 3, SEQ ID NO: 11 was cloned from SEQ ID NO: 4, SEQ ID NO: 12 was cloned from SEQ ID NO: 5, SEQ ID NO: 13 was cloned from SEQ ID NO: 6 SEQ ID NO: 14 was cloned from SEQ ID NO: 7).

Assessment of fungal-isolated PPO gene tolerance in transgenic plants—T1 or T2 generation transformed seeds were germinated on Basta selection (Bayer) according to manufacturer instructions (~30-35 plants per pot, four pots per gene). When reaching two rosette leaves, plants were treated with PPO-inhibitor herbicide by foliar application of Strike (Flumioxazin 50%, Adama) or Aurora (40% Carfentrazone-Ethyl, FMC), at concentrations ranging from 0.000015% to 1% diluted in water as indicated herein below.

Results:

Assessment of PPO tolerance of WT *Arabidopsis* plants and transgenic plants expressing fungal-isolated PPO having amino acid sequence as denoted by SEQ ID NOs: 1-3, 6 and the N terminus cTP fusions denoted by SEQ ID NOs: 8-12, and 14 was performed (FIG. 1A-1B).

To assess the level of susceptibility of *Arabidopsis* plants towards Strike, an initial calibration was aimed to set the limit of natural tolerance of the WT plants. For that, WT *Arabidopsis* plants were treated with low levels of Strike, 0.000015% and 0.00003%. diluted in water FIG. 1A shows that WT plants are susceptible to these low amounts of Strike.

To assess the level of tolerance exhibited by transgenic *Arabidopsis* plants expressing the different fungal-isolated PPO genes, three experiment were performed in transgenic plants. In experiment #1, T2 generation transformed seeds were germinated and plants were treated with 0.01%, 0.1% and 0.5% Strike. In experiment #2, T2 generation transformed seeds were germinated in two separate tables, one for each PPO-inhibitor herbicide selection treatment, followed by treatment of plants in one table with 0.01%, 0.1%, 0.5% and 1% Strike and plant in the second table with 0.01%, 0.1% and 0.5% Aurora.

FIG. 1B summarizes the results of the three experiments described hereinabove. The level of tolerance exhibited by the transgenic plants was assessed using a four data points plant resilience score that was given in scale of 0-5 where '0', represents highly damaged plants and '5' represents highly tolerant/resistant plants.

Advantageously and unexpectedly, all PPO-genes derived from the genera of *Aspergillus* sp. Encoding the amino acids set forth in SEQ ID NO: 1, SEQ ID NO: 8 and SEQ ID NO: 2, and SEQ ID NO: 9, *Fusarium* sp. Encoding the amino acids set forth in SEQ ID NO: 3, SEQ ID NO: 10, SEQ ID NO: 11, and SEQ ID NO: 12, *Rhizopus* sp. Encoding the amino acids set forth in SEQ ID NO: 6, and *Penicillium* sp. Encoding the amino acids set forth in SEQ ID NO: 14, conferred high levels of tolerance (i.e., tolerance of more than about $10^4$ times (4 orders of magnitude) of WT) to the transgenic plants against the PPO-inhibitor herbicides Strike and/or Aurora.

Notably, especially advantageous are transgenic plants expressing the PPO proteins of *Aspergillus* sp. (SEQ ID NO: 1, SEQ ID NO: 8, SEQ ID NO: 2, and SEQ ID NO: 9), genes of *Fusarium* sp. (for example, SEQ ID NO: 10 and SEQ ID NO: 12), and the gene of *Rhizopus* sp. (SEQ ID NO: 6) that exhibited very high levels (i.e., about $10^5$ (5 orders of magnitude) more tolerant to treatment as compared to control plants) of resistance to strike.

Also advantageous are transgenic plants expressing the PPO proteins of *Aspergillus* sp. (for example, SEQ ID NO: 1, SEQ ID NO: 8, SEQ ID NO: 2, and SEQ ID NO: 9) and the genes of *Rhizopus* sp. (SEQ ID NO: 6) and *Penicillium* sp. (SEQ ID NO: 14) that exhibited very high levels of resistance to Aurora as compared to control plants.

Figure 2A:
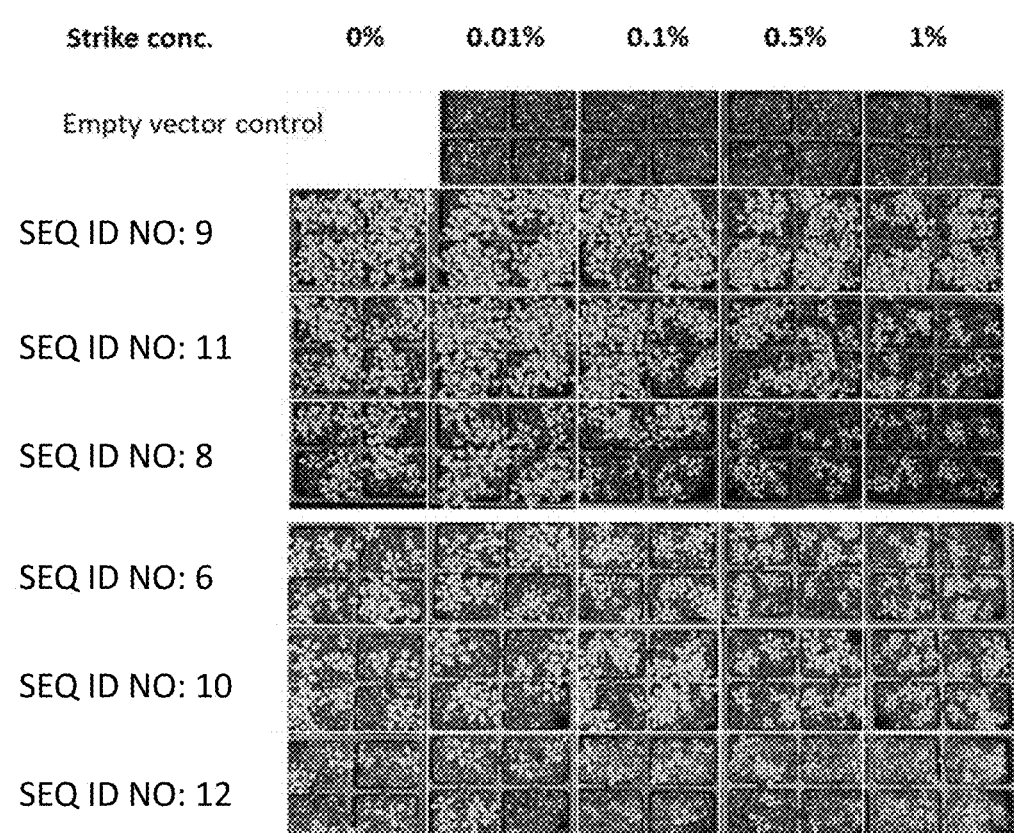
FIG. 2A-B show images of transgenic plants expressing fungal-isolated PPO tolerance genes and treated with two types of PPO-type inhibitor herbicides, Strike (Flumioxazin 50%, by Adama) (FIG. 2A) or Aurora (40% Carfentrazone-Ethyl, by FMC) (FIG. 2B), at concentrations ranging from 0.01% to 0.1%, or receiving no treatment (0%), as indicated in the figure. The effect of PPO-inhibitor on the transgenic plants is compared to control plants transformed with an empty vector.
Figure 2B:
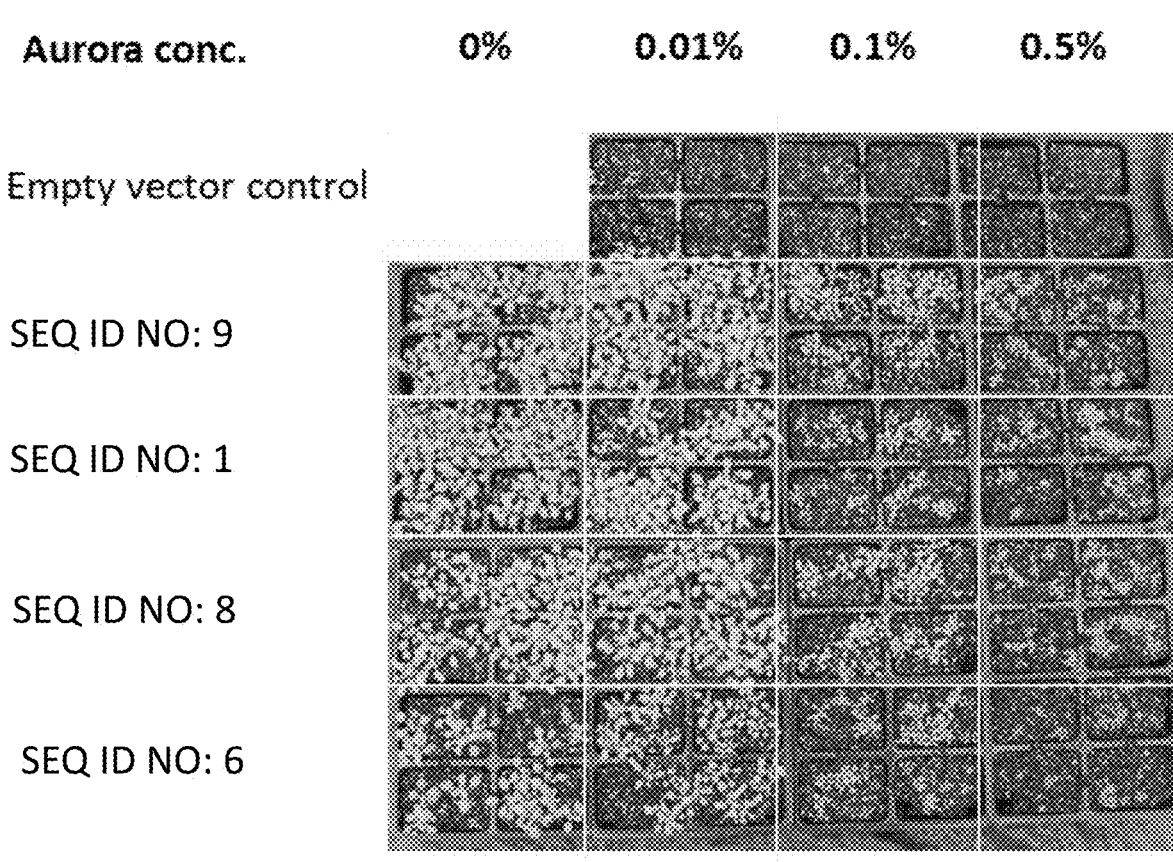

Also notable is the very high level of resistance that the *Penicillium* PPO protein (SEQ ID NO: 14) conferred to the transgenic plant against Aurora, but not against Strike, and on the other hand the high levels of resistance that *Fusarium* proteins (for example, SEQ ID NO: 10 and SEQ ID NO: 12) conferred to the transgenic plant against Strike, but not against Aurora. FIG. 2A-B show images that compare between transgenic plants of experiments #1 and #2 described hereinabove, to control plants transformed with an empty vector. The figures present the effect receiving no treatment (0%) or receiving treatment with increasing concentrations of Strike (FIG. 2A) or Aurora (FIG. 2B), have on transgenic plants expressing fungal-isolated PPO genes in comparison to control plants.

It is indicative by the figures that the transgenic plants expressing fungal-isolated PPO genes exhibit an advantageous improved growth across all range of concentration tested (0.01% to 0.5 for Aurora and 0.01% to 1% for Strike) and therefore have increased tolerance to both PPO-inhibitor herbicides when applied in a dose-dependent manner.

Example 3—Analysis of Putative Motifs in Fungal-Isolated PPO Tolerance Genes

Method:

Multiple Sequence Alignment (MSA) of fungal-isolated and plant PPO genes combined with a structural alignment—The 3D model of a PPO herbicide tolerance genes from each fungi species were predicted by the SWISS-MODEL Server (Waterhouse, A. 2018). A model of a single representative from each species were selected: SEQ ID NO: 2 (*Aspergillus*); SEQ ID NO: 3 (*Fusarium*); SEQ ID NO: 6 (*Rhizopus*); SEQ ID NO: 7 (*Penicillium*). Model #1 Template is the Protoporphyrinogen oxidase structure of human protoporphyrinogen IX oxidase (HsPPO) (PDB: 3NKS.1.A; Qin X., 2011) having amino acid sequence denoted by SEQ ID NO: 101 The models were aligned (structure-based alignment) over 3NKS and 1SEZ (*N. tabacum* mitochondrial PPO2; Koch M., 2004 and PDB) using the SWISS-MODEL server.

Additional PPO herbicide tolerance genes were aligned separately against its species representative, and the alignments were combined to the structure-based alignment: SEQ ID NO: 1 against SEQ ID NO: 2 (*Aspergillus*); SEQ ID NO: 4 and SEQ ID NO: 5 against SEQ ID NO: 3 (*Fusarium*). The sequences of plant PPOs were combined to the structure-based alignment with the same practice: mitochondrial PPO from *Arabidopsis thaliana* (AtPPO2) having amino acid sequence denoted by SEQ ID NO: 119, chloroplast PPO from *N. tabacum* (NtPPO1) having amino acid sequence denoted by SEQ ID NO: 120, *Arabidopsis thaliana* (AtPPO1) having amino acid sequence denoted by SEQ ID NO: 121 and Soybean (GmPPO1) having amino acid sequence denoted by SEQ ID NO: 102, were aligned with the sequence of mitochondrial PPO of *N. tabacum* (NtPPO2) having amino acid sequence denoted by SEQ ID NO: 103 with T-coffee server (Notredame, C., 2000). The alignment was combined to the structure-based alignment according to the sequence of NtPPO2.

Results:

Amino acid sequences of Fungal-PPO enzymes were analyzed and compared against those of plant PPO and human PPO, in order to identify putative Fungal motifs that may be responsible for the improved tolerance manifested by the transgenic plants.

According to some embodiments, ten motifs (motifs 1-10) were recognized in fungal-isolated PPO. The motifs are about 4 to about 30 amino acids in length. According to some embodiments, the motifs that were identified in fungal-isolated PPO advantageously share unique patterns of amino acid sequence and/or structure. According to some embodiments, motifs of fungal-derived PPO sequences may share more common amino acid sequences and/or structural features between enzymes of *Aspergillus, Fusarium, Rhizopus*, and *Penicillium*, than the corresponding sequences of the plant derived-PPO share between enzymes of *Arabidopsis, Tabacum*, and Soybean, for example, motifs 1, 2, 3, 4, 6, 7, and 10.

Advantageously, according to some embodiments, a total of 70 motif sequences identified in fungal-isolated PPO enzymes of the genera *Aspergillus* sp., *Fusarium* sp., *Rhizopus* sp., and *Penicillium* sp., were considered distinct and distinguishable with respect to their corresponding sequences in plants PPO enzyme.

According to some embodiments, the 70 motifs have an amino acid sequence as set forth in SEQ ID NO: 16-85.

Example 4—in Planta Screening of PPO Tolerance Genes, Identification of Fungal-Isolated PPO Tolerance, and Assessment of their Tolerance in Transgenic Plants In planta screening of PPO tolerance genes and identification of Fungal-isolated PPO tolerance genes—In addition to the PPO tolerant genes demonstrated in hereinabove Examples 1-2, other PPO genes were screened for tolerance.

PPO genes having amino acid sequences as denoted by any one of SEQ ID NOs: 86-100 were identified as Fungal-isolated PPO genes, by sequencing and annotation of their corresponding nucleic acid transgenes: after in planta screening was performed to identify potential PPO tolerance genes against PPO-type inhibitor herbicides, similarly to the hereinabove experiment described in Example 1.

The amino acid sequences of the isolated fungal PPO genes are set forth in:

SEQ ID NO: 86 (PPO from *Trichoderma* sp.);
SEQ ID NO: 87 (PPO from *Aspergillus* sp.);
SEQ ID NO: 88 (PPO from *Aspergillus* sp.);
SEQ ID NO: 89 (PPO from *Fusarium* sp.);
SEQ ID NO: 90 (PPO from *Fusarium* sp.);
SEQ ID NO: 91 (PPO from *Rhizopus* sp.);
SEQ ID NO: 92 (PPO from *Rhizopus* sp.).
SEQ ID NO: 93 (PPO from *Rhizopus* sp.).
SEQ ID NO: 94 (PPO from *Penicillium* sp.).
SEQ ID NO: 95 (PPO from *Penicillium* sp.);
SEQ ID NO: 96 (PPO from *Trichoderma* sp.);
SEQ ID NO: 97 (PPO from *Rhodotorula* sp.);
SEQ ID NO: 98 (PPO from *Hesseltinella* sp.);
SEQ ID NO: 99 (PPO from *Spizellomyces* sp.);
SEQ ID NO: 100 (PPO from *Rhizophagus* sp.);

Assessment of Fungal-Isolated PPO Gene Tolerance in Transgenic Plants—

Methods:

Cloning and transformation of fungal PPO genes—The nucleotide sequences encoding the PPO protein were cloned into a binary plant expression vector under the control of the 35S constitutive promoter and HSP terminator.

The vectors were used to transform *Arabidopsis* plants using *agrobacterium* according to the flower dipping method.

Generation of cTP chimeric PPO genes chloroplast transit peptide (cTP) (SEQ ID: 15) chimeric PPO genes having an amino acid sequence denoted as SEQ ID NOs: 104-118 (N-terminus amnio acid 1-38 is cTP from *Arabidopsis thaliana*) were generated from their respective fungal PPO tolerance genes denotated as SEQ ID NOs: 86-100, to enhance the performance of their polypeptides as PPO inhibitors resistant genes in following in-planta experiments, i.e., SEQ ID NO: 104 cloned from SEQ ID NO: 86, SEQ ID NO: 105 cloned from SEQ ID NO: 87, SEQ ID NO: 106 cloned from SEQ ID NO: 88, SEQ ID NO: 107 cloned from SEQ ID NO: 89, SEQ ID NO: 108 cloned from SEQ ID NO: 90, SEQ ID NO: 109 cloned from SEQ ID NO: 91, SEQ ID NO: 110 cloned from SEQ ID NO: 92, SEQ ID NO: 111 cloned from SEQ ID NO: 93, SEQ ID NO: 112 cloned from SEQ ID NO: 94, SEQ ID NO: 113 cloned from SEQ ID NO: 95, SEQ ID NO: 114 cloned from SEQ ID NO: 96, SEQ ID NO: 115 cloned from SEQ ID NO: 97, SEQ ID NO: 116 cloned from SEQ ID NO: 98, SEQ ID NO: 117 cloned from SEQ ID NO: 99, SEQ ID NO: 118 cloned from SEQ ID NO: 100.

Assessment of fungal-isolated PPO gene tolerance in transgenic plants—T2 generation transformed seeds were germinated on Basta selection (Bayer) according to manufacturer instructions (~30-35 plants per pot, four pots per gene). When reaching two rosette leaves, plants were treated with PPO-inhibitor group 14 herbicide by foliar application of Strike (Flumioxazin, Adama), Star (Oxadiazon, Tapazol), Goal (Oxyfluorfen, Corteva), or Aurora (Carfentrazone- Ethyl, FMC), were diluted in water and applied at concentrations also including 1.0 kg/hectare, 1.15 kg/hectare, 1.25 kg/hectare or 2.5 kg/hectare.

Results:

Assessment of PPO tolerance to PPO-herbicides (Group 14 herbicides) was performed in *Arabidopsis thaliana* in WT plants, transgenic plants transformed with "empty" vector, and transgenic plants expressing fungal-isolated PPO fused to the cTP (at the N-terminus of the proteins) as denoted in SEQ ID NOs: 8-14 and SEQ ID NOs: 104-118 and (FIG. 3A-3C).

For the evaluation of the relative survival/resilience exhibited by the transgenic plants in the experiments described hereinafter, a representative resilience scale, including 5 levels of resiliency/survival (score 1-5), where '1' represents highly damaged plants and '5' represents highly resistant plants, was used as a reference for scoring plants survival/resiliency, as can be seen in FIG. 3A.

First, as seen in FIG. 3B, all transgenic plants harboring/expressing fungal isolated-PPO gene having amino acid sequence as denoted in any one of SEQ ID NOs: 8-14 and SEQ ID NOs: 104-118 were assayed for tolerance against Strike at concentration of 2.5 kg/hectare.

Advantageously, transgenic plants corresponding to SEQ ID NOs: 8-14, 104, 106-107, and 109-117 (and their respective SEQ ID NOs: 1-7, 86, 88-89, 91-99) exhibited growth with some level of tolerance (corresponding to a resilience score of 2, 3, 4 or 5) in the presence the herbicide. This is compared to control plants (WT and plants transformed with empty vector) that exhibited an acute growth inhibition and leaf bleaching as indicative by their very low tolerance score of 1.

Transgenic plants corresponding to SEQ ID NOs: 8-12, 14, 109-111, 114-115 exhibited growth with a higher level of tolerance (corresponding to a resilience score of 3, 4 or 5) in the presence of the herbicide Strike at concentration of 2.5 kg/hectare.

Transgenic plants corresponding to SEQ ID NOs: 8-12, 14, 114-115 exhibited growth with even higher level of tolerance (corresponding to a resilience score of 4 or 5) in the presence of the herbicide Strike at concentration of 2.5 kg/hectare.

Next, PPO tolerance was evaluated in the presence of a wider array of PPO-herbicides of Group 14: Strike at concentration of 2.5 kg/hectare, Star at concentration of 1.25 kg/hectare, Goal at concentration of 1.15 kg/hectare, and Aurora at concentration of 1.0 kg/hectare.

The results of this survival assay performed in the presence of Strike, Star, Goal and Aurora, are presented in FIG. 3C presenting only those plants expressing fungal isolated-PPO gene exhibiting growth with some level of tolerance to all 4 herbicides tested (corresponding to a resilience score of 2, 3, 4 or 5), while control plants (WT and plants transformed with empty vector) exhibited an acute growth inhibition and leaf bleaching as indicative by their very low tolerance score of 1.

Advantageously, the best 5 fungal isolated-PPO having amino acid sequence are denoted by any one of SEQ ID NOs: 9, 112, 114-116 and belonging to the genus *Aspergillus, Penicillium, Trichoderma, Rhodotorula*, and *Hesseltinella*.

The top 3 fungal isolated-PPO genes that grow in the presence of Strike, Star, Goal and Aurora herbicides having amino acid sequence denoted by SEQ ID NOs: 9, 114 and 115, and belonging to the genus *Aspergillus, Trichoderma*, and *Rhodotorula*, respectively.

The top 2 fungal isolated-PPO gene that grow in the presence of Strike, Star, Goal and Aurora herbicides having amino acid sequence denoted by SEQ ID NOs: 9, and 115, and belonging to the genus *Aspergillus*, and *Rhodotorula*, respectively.

The best performing fungal isolated-PPO gene that grew in the presence of Strike, Star, Goal and Aurora herbicides having amino acid sequence denoted by SEQ ID NOs: 9, belonging to the genus *Aspergillus*.

Plants expressing the genes denoted by SEQ ID NO: 112 and 116 and belonging to genus *Penicillium* and *Hesseltinella*, respectively, showed tolerances against Goal and Star herbicides only (FIG. 3C).

To conclude, it is indicative by FIGS. 3B-3C that transgenic plants expressing fungal-isolated PPO genes belonging to any one of the fungal genus of *Aspergillus, Penicillium, Trichoderma, Rhodotorula*, and *Hesseltinella*, exhibit an advantageous improved growth across all range of concentration tested.

Example 5—Structural/Geometrical Analysis of Putative Amino Acid Positions in Fungal-Isolated PPO Tolerance Genes Methods:

The secondary and tertiary structures of the proteins denoted by SEQ ID Nos: 1-7 and SEQ ID NOs 86-100 were predicted as described in ColabFold V1.5.2 (Mirdita, M., Schutze, K., Moriwaki, Y. et al. ColabFold: making protein folding accessible to all. Nature Methods 19, 679-682 (2022). These structures were then compared to crystallized proteins as a reference including human protoporphyrinogen IX oxidase (PDB identifier: 4IVO)—SEQ ID NO: 101 that is crystalized with the herbicide Acifluorfen (5-[2-Chloro-4-(trifluoromethyl)phenoxy]-2-nitrobenzoic acid), and *Nicotiana tabacum* protoporphyrinogen IX oxidase (PDB identifier: 1SEZ)—SEQ ID NO: 103; in order to identify their relevant amino acids in the location/position of their domains and active sites.

Proteins were structurally aligned with Pymol (The PyMOL Molecular Graphics System, Version 2.0 Schrödinger, LLC.) using the 'superimpose' method. Structural similarity across proteins was computed using the RMSD (Root Mean Square Deviation) measurement and colored accordingly.

The active site and the binding sites for the herbicide Acifluorfen (5-[2-Chloro-4-(trifluoromethyl)phenoxy]-2-nitrobenzoic acid) and for FAD (Flavin Adenine Dinucleotide) were compared in sequence and structural composition for the novel fungal-isolated PPO genes discovered. Using the proteins found in PDB as reference for structural homology, the residues involved in substrate and FAD binding were identified, marked and compared.

Figure 4A:
FIG. 4A shows a ribbon diagram illustration of the 3D structure of *Glycine max* PPO (SEQ ID NO: 102)—a typical PPO protein—presenting the structural components (yellow) of the herbicide binding pocket. An alpha helix is positioned across several beta sheets (marked in yellow) that form the main contact point for herbicide molecules. Distally from the pocket opening, a small number of residues form a hydrophobic pocket which stabilizes the herbicide moiety (outlined by the red dots).
Figure 4B:
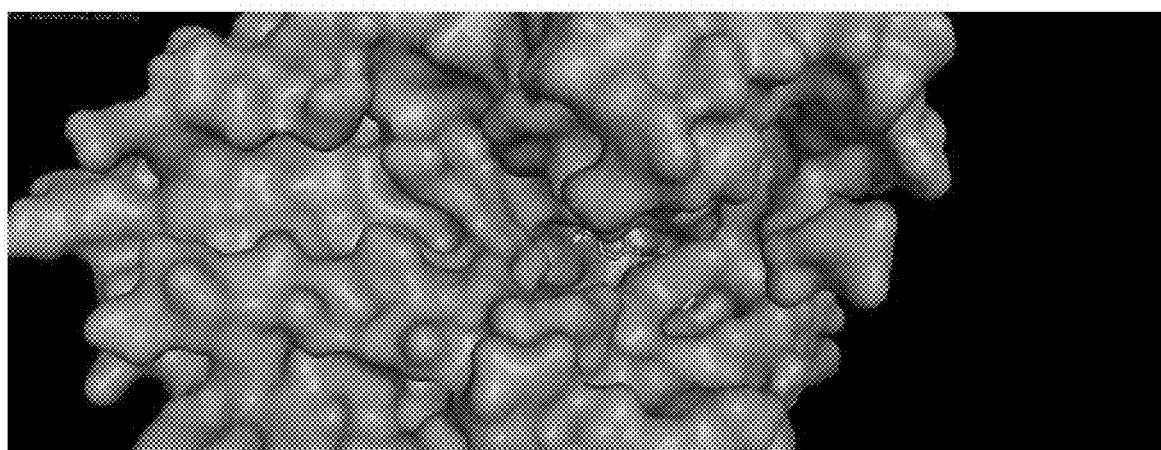
FIG. 4B shows a surface view illustration of the 3D structure of the human PPOX (SEQ ID NO: 101) presenting the opening to the pocket conformationally oriented towards the viewer. The herbicide acifluorfen in its bonded position is shown in purple.

Results:

3D structural features of *Glycine max* PPO (SEQ ID NO: 102) and of human PPOX (SEQ ID NO: 101) bound with the herbicide acifluorfen can be seen in FIG. 4A and FIG. 4B, respectively.

The active site for the substrate protoporphyrinogen IX and FAD binding site of the PPO proteins having amino acid sequence as denoted by SEQ ID NOs 1-7 (corresponding to SEQ ID NO: 8-14, respectively) and SEQ ID NOs 86-100 (corresponding to SEQ ID NO: 104-118, respectively) were found to be predominantly similar in structure and function. It was also observed that PPO protein having amino acid sequence as denoted by SEQ ID NO: 2 (corresponding to SEQ ID NO: 9) possesses the same pocket structure with the herbicide acifluorfen when superimposed on top of SEQ 101.

While the structure and sequence of the residues composing the herbicide pocket exhibit a high similarity, several key structural/geometrical differences were identified, which may explain the advantageous differences in herbicide tolerance activity of the fungal isolated proteins relative to human PPOX or plant PPO from *Glycine Max, Arabidopsis* or *tabacum. These include* 4 modes for the required resistance/tolerance:

(i) reduction in herbicide pocket opening size;
(ii) de-stabilizing hydrogen bonds at positions corresponding (by structural alignment) to human position Arg62 and Arg97;
(iii) steric hindrance at position corresponding (by structural alignment) to human position V347 affects the binding to the herbicide; and
(iv) de-stabilizing conformation at position corresponding (by structural alignment) to human position F331 that possibly affects binding to the herbicide;

1. Reduction in Herbicide Pocket Opening Size

As seen in FIG. 5A and FIG. 5B—illustration of human PPOX (SEQ JD NO: 101) structure and binding pocket—the size of the opening of the herbicide binding pocket was measured (distance is shown by a dashed yellow line).

The measurement of the size of the herbicide pocket opening was performed by measuring the distance from an alpha helix structure (shown in FIG. 5A (II) in yellow) to the widest point of the opening of the pocket, as shown by a dashed yellow line in FIG. 5B.

This distance was measured as 10.8 angstrom.

The alpha helix structure is positioned in an identical orientation in the human and plant PPOs having amino acid sequence denoted by SEQ ID NOs: 101-103 (sensitive for PPO-herbicides), as well as in the fungal PPOs having amino acid sequence as denoted by any one of SEQ ID NOs: 2, 94, 96-98 (show tolerance for PPO-herbicides) and is therefore used as a reference point for measuring and comparing the pocket opening size, as shown in FIG. 5B.

Figure 5C:
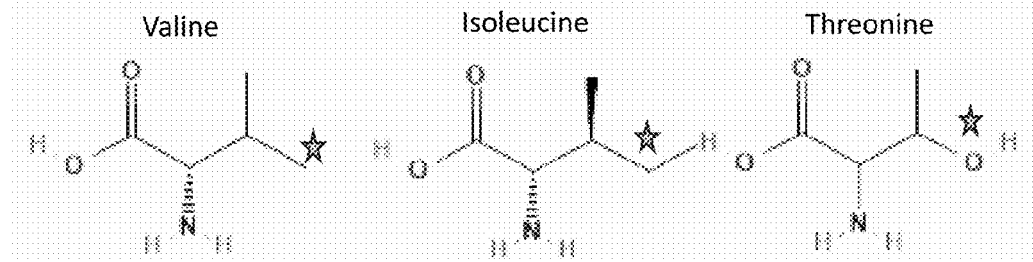
FIG. 5C shows a schematic illustration of 3 amino acids at a structurally corresponding position: Valine, Isoleucine and Threonine, involved in the measurement of the opening distance of the herbicide binding pocket, as they are located within the alpha helix. These 3 amino acids are either human V170 of the PPOs having amino acid sequence denoted by SEQ ID NO: 101, or amino acids at a structurally corresponding position in any one of the PPOs having amino acid sequence denoted by SEQ ID Nos: 102-103 and SEQ ID Nos: 2, 94, 96-98 (see FIG. 6B; Valine, Isoleucine or Threonine at structurally corresponding position to human V170 are marked in green). The specific atoms used for measuring the distance to same position on the alpha helix are marked by the gold star. In spite of differences in side chains, the three indicated atoms occupy the same structurally corresponding position in the three-dimensional space, therefore allowing measurements to be compared.

The pocket opening size was measured as the distance between the same position on the alpha helix which is occupied by a specific atom of human V170, or amino acid at a structurally corresponding position (Valine, Isoleucine or Threonine) (see FIG. 5C, for the specific atom) in plant and fungal PPOs, to the amino group of the side chain of human Arg62, or amino acid at a structurally corresponding position in plant and fungal PPOs representing the widest point of the opening of the pocket, as shown in FIG. 5B and FIG. 5C.

Whereas, in cases where the amino acid at a structurally corresponding position to human Arg62, in plant and fungal PPOs, is not arginine (i.e., see FIG. 6B: Q123 (SEQ ID NO: 102), T70 (SEQ ID NO: 103) or S102 (SEQ ID NO: 96)) distances were measured from the same position occupied by: the amino group at the end of the side chain of Glutamine in SEQ ID NO: 102, the methyl group at the end of the side chain of threonine in SEQ ID NO:103, and the hydroxyl group at the end of the side chain of serine in SEQ ID NO: 96. While these three amino acids have different chemical groups, structurally they occupy the same position and form the inner edge of the pocket opening so the distance measured was the smallest, so the specific atom was always located at the end of the side chain.

The sizes of the pocket opening of the aforementioned human, plant and fungal PPO is presented below in Table 1.

TABLE 1 sizes of the pocket opening of human, plant and fungal PPO

| SEQ ID | Pocket opening size (angstrom) | High concentration herbicide tolerance | Difference in Pocket opening size (angstrom) relative to SEQ ID NO: 101 |
|---|---|---|---|
| Seq ID NO: 101 | 10.8 | no | — |
| Seq ID NO: 102 | 11.1 | no | 0.3 |
| Seq ID NO: 103 | 10.8 | no | 0 |
| Seq ID NO: 2 | 6.8 | yes | 4 |
| Seq ID NO: 94 | 7.7 | yes | 3.1 |
| Seq ID NO: 96 | 8.7 | yes | 2.1 |
| Seq ID NO: 97 | 7.9 | yes | 2.9 |
| Seq ID NO: 98 | 5.3 | yes | 5.5 |

Advantageously and surprisingly, as can be seen from FIG. 5B and from the measured distances presented in Table 1, a significant difference was found to exists in the size of the opening of the herbicide binding pocket between the human and plant sensitive PPOs and the tolerant fungal PPOs.

PPO proteins of human (SEQ ID NO: 101), *Glycine max* (SEQ ID NO: 102) and *Nicotiana tabacum* (SEQ ID NO: 103) are sensitive to PPO herbicides/inhibitors of group 14 and have a larger pocket opening of at least 10.8 angstrom. Differently, the tolerant fungal isolated PPO proteins having amino acid sequence as denoted by any one of SEQ ID Nos: 2, 94, 96, 97, and 98 are characterized by a much smaller opening of not more than 8.7 angstrom for SEQ ID NO: 96.

The difference in the size of the opening of the herbicide binding pocket may explain the resistance of fungal isolated PPO having amino acid sequences denoted by any one of SEQ ID NOs: 2, 94, 96, 97, and 98 (or respective cTP fusions having amino acid sequences denoted by any one of SEQ ID NOs: 9, 112, 114-116), as a reduction in the measured distance in fungal PPO, relative to human or plant PPO may prevent/block/hinder the herbicide from entering into the binding pocket thereby conferring tolerance against the herbicide.

2. De-Stabilizing Hydrogen Bonds at Positions Structurally Corresponding to Human Position Arg62 and Arg97

Of particular importance is the geometrical orientation of amino acids at positions corresponding to two arginine residues: arginine at position 62 (Arg62) and arginine at position 97 (Arg97) located within the herbicide binding pocket of the human PPOX.

As seen in FIG. 6A that illustrate the hydrogen bonds formed between the guanidinium group of the two arginine residues, Arg97 (Distance 1) and Arg62 (Distance 2), located within the herbicide binding pocket of the human PPOX and the oxygen atom of the acifluorfen herbicide, either at the hydroxyl (Distance 1) or carbonyl groups (Distance 2) of C11, respectively.

Particularly advantageous and surprising, was the finding that at least one of the two Arginine residues identified in *Homo sapiens* PPOX (SEQ ID NO: 101) as Arg62 and Arg97, are conserved in each one of the fungal-isolated PPOs having an amino acid sequence denoted by any one of SEQ ID NOs: 2, 94, 96-98 (respective to cTP containing SEQ ID NOs: 9, 112, 114-116).

Both Arg62 and Arg97, are conserved in each one of the fungal-isolated PPOs having an amino acid sequence denoted by any one of SEQ ID NOs: 2, 94, 97-98 (respective to cTP containing SEQ ID NOs: 9, 112, 115-116); while only Arg97 is conserved in the fungal-isolated PPO having an amino acid sequence denoted by SEQ ID NO: 96 (respective to cTP containing SEQ ID NO: 114).

The conservation of the positions corresponding to human Arg62 and human Arg97 is presented in FIG. 6B showing amino acids residues, and positions thereof, that form the herbicide binding pocket, structurally aligned, and presented in a format of a table. SEQ ID:101 (*Homo sapiens* PPOX data is the crystallized form with acifluorfen) is the reference sequence for the structural alignment including Arg62 and Arg97, and together with SEQ ID:102 (GmPPO, from soybean *Glycine Max*) both are considered as PPO-herbicide susceptible/sensitive proteins.

However, even though fungal PPO positions corresponding to human Arg62 and human Arg97 are conserved (except for position S102 of SEQ ID NO: 96 or SEQ ID NO: 114 that corresponds to human Arg62 but which is not conserved) their conformational orientations are affected by the protein folding, likely diminishing the capacity of these amino acids to bind effectively to the herbicide, therefore promoting/inducing PPO-herbicide tolerance (residues contributing to tolerance are marked in red in FIG. 6B).

The distances measured in FIG. 6C and summarized in Table 2 below, are between the guanidinium group of the two arginine residues: human Arg62 and human Arg97, or residues at a structurally corresponding position in fungal PPO, located within the herbicide binding pocket of the human PPOX and the oxygen atom of the acifluorfen herbicide, either at the hydroxyl (Distance 1; d1) or carbonyl groups (Distance 2; d2) of C11, respectively.

As seen in FIG. 6C and summarized in Table 2 below, distance 1 (d1) and distance 2 (d2), as well as the sum of the distances, is larger in tolerant fungal PPO, having amino acid sequence as denoted by SEQ ID NOs: 2, 94, 96-98, relative to the sensitive human PPOX having amino acid sequence as denoted by SEQ ID NO: 100 or the sensitive plant PPO having amino acid sequence as denoted by SEQ ID NO: 101.

TABLE 2 measured distances between human Arg62 and human Arg97, or residues at structurally corresponding positions in fungal PPO, and the oxygen atom of the acifluorfen herbicide.

| Protein ID | Distance 1 (angstrom) | Distance 2 (angstrom) | Sum of the distances (angstrom) | Difference in sum distance relative to SEQ ID NO: 101 (angstrom) | Herbicide tolerance |
|---|---|---|---|---|---|
| Seq ID NO: 101 | 2.9 | 3.6 | 6.5 | | no |
| Seq ID NO: 100 | 5.5 | 4.6 | 10.1 | 3.6 | no |
| Seq ID NO: 98 | 7.4 | 6.4 | 13.8 | 7.3 | yes |
| Seq ID NO: 97 | 5.6 | 9.0 | 14.6 | 8.1 | yes |
| Seq ID NO: 2 | 6.2 | 9.1 | 15.3 | 8.8 | yes |

TABLE 2-continued

| | measured distances between human Arg62 and human Arg97, or residues at structurally corresponding positions in fungal PPO, and the oxygen atom of the acifluorfen herbicide. | | | | |
|---|---|---|---|---|---|
| Protein ID | Distance 1 (angstrom) | Distance 2 (angstrom) | Sum of the distances (angstrom) | Difference in sum distance relative to SEQ ID NO: 101 (angstrom) | Herbicide tolerance |
| Seq ID NO: 94 | 6.5 | 8.8 | 15.3 | 8.8 | yes |
| Seq ID NO: 96 | 6.5 | 9.4 | 15.9 | 9.4 | yes |

For Example, in tolerant fungal PPOs having amino acid sequence as denoted by any one of SEQ ID NOs: 2, 94, 96-98, the distance (d1) is more than 5.5 Angstrom, while in sensitive human PPOX having amino acid sequence as denoted by SEQ ID NO: 100 or the sensitive plant PPO having amino acid sequence denoted by SEQ ID NO: 101 d1 is no more than 5.5 angstrom. In addition, in tolerant fungal PPOs having amino acid sequence as denoted by any one of SEQ ID NOs: 2, 94, 96-98, the distance (d2) is at least 6.4 Angstrom, while in sensitive human PPOX denoted by SEQ ID NO: 100 or the sensitive plant PPO denoted by SEQ ID NO: 101 d1 is no more than 4.6 angstrom. Similarly, the sum of distances is at least 13.8 in the tolerant fungal PPOs and no more than 10.1 in the sensitive PPO.

3. Steric Hindrance at Position Structurally Corresponding to Human Position V347 Affects the Binding Pocket Size As seen in FIG. 7 a comparison was performed between the geometrical orientation of Valine V347 in the PPO binding pocket of the susceptible human PPOX denoted by SEQ ID NO: 101 and the corresponding (by structural alignment) phenylalanine F404 of the tolerant fungal PPO denoted by SEQ ID NO: 96 (see FIG. 6B). SEQ ID NO: 96 exhibits a phenylalanine in a position that most other proteins have a Valine or Isoleucine. The added aromatic compound is facing into the pocket and interfering with the intermolecular bridge linking the amino acid moieties of the herbicide.

4. De-Stabilizing Conformation at Position Structurally Corresponding to Human Position F331

As seen in FIG. 8 a comparison was performed between the geometrical orientation of phenylalanine F331 in the PPO binding pocket of the susceptible human PPOX denoted by SEQ ID NO: 101 and the corresponding (by structural alignment) phenylalanine F383 of the tolerant fungal PPO denoted by SEQ ID NO: 96 (see FIG. 6B). F331 together with Leucine at position 334 (not shown in FIG. 6B) stabilizes the herbicide molecule in the pocket of the human PPOX. Differently, SEQ ID NO:96 has Phenylalanine in a corresponding position F383, which is oriented perpendicular compared to the human PPOX, therefore the herbicide molecule is not stabilized inside the pocket, contributing to its tolerance.

In summary, even though the structure and sequence of the residues composing the herbicide pocket exhibit a high similarity, structural/geometrical differences were identified between sensitive/susceptible PPOs (i.e., human PPOX or plant PPO for example from *Glycine Max, Arabidopsis* or *tabacum*) and resistant/tolerant PPOs (i.e., fungal isolated). These advantageous and surprising differences/mechanism of tolerance are summarized in Table 3 below.

TABLE 3

| | summary of modes/mechanism of acquiring PPO-herbicide tolerance in fungal-isolated PPOs, | | | |
|---|---|---|---|---|
| | Mechanism of PPO herbicide resistance | | | |
| SEQ ID | Small Pocket opening | Loss of the stabilizing hydrogen bonds at R62 and R97 positions* | Stabilizing the herbicide at F331 position* | Reduction of the pocket size at V347 position* |
| SEQ ID NO: 98 | ✓✓ | ✓ | | |
| SEQ ID NO: 94 | ✓ | ✓ | | |
| SEQ ID NO: 97 | ✓ | ✓ | | |
| SEQ ID NO: 96 | ✓ | ✓ | ✓ | ✓ |
| SEQ ID NO: 2 | ✓✓ | ✓ | | |

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims which follow.

The invention claimed is:

1. A transgenic plant comprising a nucleic acid encoding an exogenous fungal-derived Protoporphyrinogen Oxidase (PPO) enzyme conferring resistance to at least one PPO-inhibitor herbicide, wherein the exogenous fungal-derived PPO enzyme comprises an amino acid sequence having at least 95% similarity to the amino acid sequence of any one of: SEQ ID NOs: 1-7, SEQ ID NO: 86, SEQ ID NOs: 88-89, or SEQ ID NOs: 91-99.

2. The transgenic plant of claim 1, wherein the fungal-derived PPO enzyme comprises an amino acid sequence having at least 98% identity to the one amino acid sequence of any one of SEQ ID NOs: 1-7, SEQ ID NO: 86, SEQ ID NOs: 88-89, or SEQ ID NOs: 91-99.

3. The transgenic plant of claim 1, wherein the fungal-derived PPO enzyme further comprises a plant chloroplast transit peptide.

4. The transgenic plant of claim 1, wherein the fungal-derived PPO is from a fungal species selected from *Aspergillus* sp., *Fusarium* sp., *Rhizopus* sp., *Penicillium* sp., *Trichoderma* sp., *Rhodotorula* sp., *Hesseltinella* sp., *Spizellomyces* sp. *Rhizophagus* sp., *Alternariav* sp., and *Cladosporium* sp.

5. The transgenic plant of claim 4, wherein the fungal-derived PPO enzyme is from a fungal species selected from the group consisting of *Aspergillus* sp., *Fusarium* sp., *Rhizopus* sp., *Penicillium* sp., and *Trichoderma* sp.

6. The transgenic plant of claim 4, wherein the fungal-derived PPO is from a fungal species selected from *Aspergillus* sp., *Penicillium* sp., *Trichoderma* sp., *Rhodotorula* sp., and *Hesseltinella* sp.

7. The transgenic plant of claim 1, wherein the fungal-derived PPO enzyme is from a fungal species of the clade leotiomyceta.

8. The transgenic plant of claim 1, wherein the plant is selected from the group consisting of maize, wheat, rice, barley, soybean, cowpea, chickpea, cotton, sorghum, beans, rapeseed/canola, alfalfa, flax, sunflower, safflower, millet, rye, sugarcane, sugar beet, cocoa, tea, *Brassica*, coffee, sweet potato, flax, peanut, clover, lettuce, tomato, cucurbits, cassava, potato, carrot, radish, pea, lentils, cabbage, cauliflower, broccoli, brussels sprouts, peppers, pineapple, citrus, apple, pear, peach, apricot, walnut, avocado, banana, palm, *eucalyptus*, poplar, pine, coconut, orchids, *petunia*, carnations, roses, switchgrass, prairie grasses, indian grasses, big bluestem grass, and camelina.

9. The transgenic plant of claim 8, wherein the plant is selected from the group consisting of maize, wheat, rice, soybean, cowpea, chickpea, cotton, sorghum, rapeseed/canola, alfalfa, sunflower, sugarcane, sugar beet and camelina.

10. The transgenic plant of claim 1, wherein the at least one PPO inhibitor is selected from the group consisting of herbicide families Phenylpyrazoles, Pyrimidindiones, Oxazolidinedione, Diphenylethers, Oxadiazoles, N-phenylphthalimides, Triazinone, Thiadiazoles, Triazolinones, and Triazolopyridinones.

11. The transgenic plant of claim 1, wherein the plant is a broad leaf plant.

12. The transgenic plant of claim 1, wherein the plant is a cereal plant.

13. A seed of the transgenic plant of claim 1, wherein the seed comprises said nucleic acid.

* * * * *